United States Patent
Yang et al.

(10) Patent No.: US 11,801,307 B2
(45) Date of Patent: Oct. 31, 2023

(54) ANTIBODY-POLYMER-DRUG CONJUGATES

(71) Applicant: UNIVERSITY OF UTAH RESEARCH FOUNDATION, Salt Lake City, UT (US)

(72) Inventors: Jiyuan Yang, Salt Lake City, UT (US); Jindrich Kopecek, Salt Lake City, UT (US); Libin Zhang, Salt Lake City, UT (US); Yixin Fang, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 484 days.

(21) Appl. No.: 16/334,301

(22) PCT Filed: Oct. 13, 2017

(86) PCT No.: PCT/US2017/056515
§ 371 (c)(1),
(2) Date: Mar. 18, 2019

(87) PCT Pub. No.: WO2018/071767
PCT Pub. Date: Apr. 19, 2018

(65) Prior Publication Data
US 2019/0216945 A1 Jul. 18, 2019

Related U.S. Application Data

(60) Provisional application No. 62/449,209, filed on Jan. 23, 2017, provisional application No. 62/408,512, filed on Oct. 14, 2016.

(51) Int. Cl.
| | | |
|---|---|---|
| *A61K 47/68* | (2017.01) | |
| *A61P 35/00* | (2006.01) | |
| *C07K 16/28* | (2006.01) | |
| *A61K 39/395* | (2006.01) | |
| *A61K 38/07* | (2006.01) | |
| *A61K 47/58* | (2017.01) | |
| *A61K 39/00* | (2006.01) | |
| *A61K 31/337* | (2006.01) | |
| *A61K 31/351* | (2006.01) | |

(52) U.S. Cl.
CPC .......... *A61K 47/6883* (2017.08); *A61K 38/07* (2013.01); *A61K 39/395* (2013.01); *A61K 47/58* (2017.08); *A61P 35/00* (2018.01); *C07K 16/2803* (2013.01); *C07K 16/2887* (2013.01); *A61K 31/337* (2013.01); *A61K 31/351* (2013.01); *A61K 2039/505* (2013.01); *C07K 2317/92* (2013.01); *C07K 2319/035* (2013.01)

(58) Field of Classification Search
CPC .. A61K 47/6883; A61K 39/395; A61K 38/07; A61K 47/58; A61K 2039/505; A61K 31/337; A61K 31/351; C07K 16/2803; C07K 16/2887; C07K 2317/92; C07K 2319/035; A61P 35/00

See application file for complete search history.

(56) References Cited

U.S. PATENT DOCUMENTS

| | | |
|---|---|---|
| 2006/0275250 A1 | 12/2006 | Suber et al. |
| 2007/0258891 A1 | 11/2007 | Patel |
| 2013/0101546 A1 | 4/2013 | Yurkovetskiy et al. |
| 2013/0156722 A1* | 6/2013 | Kopeckova et al. .. A61K 47/48 |
| 2015/0087788 A1 | 3/2015 | Vicent Docon et al. |
| 2016/0015732 A1* | 1/2016 | Kopecek et al. .... A61K 31/712 |

FOREIGN PATENT DOCUMENTS

| | | | |
|---|---|---|---|
| CN | 106512003 A * | 3/2017 | ......... A61K 41/0052 |
| EP | 17859454.5 | 5/2019 | |
| JP | 2019520110 | 4/2019 | |
| WO | WO2003/053473 | 7/2003 | |
| WO | WO-2011072627 A2 * | 6/2011 | ........... C08G 83/003 |
| WO | WO-2011/112482 | 9/2011 | |
| WO | WO-2014/164913 | 10/2014 | |
| WO | PCT/US2017/056515 | 10/2017 | |

OTHER PUBLICATIONS

Chytil P et al., N-(2-Hydroxypropyl)methacrylamide-based polymer conjugates with pH-controlled activation of doxorubicin for cell-specific or passive tumour targeting. Synthesis by RAFT polymerisation and physicochemical characterisation. Eur J Pharm Sci. Nov. 20, 2010;41(3-4):473-82. (Year: 2010).*

Boye J, Elter T, Engert A. An overview of the current clinical use of the anti-CD20 monoclonal antibody rituximab. Ann Oncol. Apr. 2003;14(4):520-35. doi: 10.1093/annonc/mdg175. Erratum in: Ann Oncol. Jun. 2003;14(6):967. PMID: 12649096. (Year: 2003).*

Basaran M, Bavbek E, Sakar B, et al.. Treatment of Aggressive Non-Hodgkin's Lymphoma With Dose-Intensified Epirubicin in Combination of Cyclophosphamide, Vincristine, and Prednisone (CEOP-100). American Journal of Clinical Oncology. 2001; 24 (6): 570-575. (Year: 2001).*

Kopecek J, Kopecková P. HPMA copolymers: origins, early developments, present, and future. Adv Drug Deliv Rev. Feb. 17, 2010; 62(2):122-49. doi: 10.1016/j.addr.2009.10.004. Epub Nov. 14, 2009. PMID: 19919846; PMCID: PMC2836498. (Year: 2009).*

(Continued)

*Primary Examiner* — Julie Wu
*Assistant Examiner* — John J Skoko, III
(74) *Attorney, Agent, or Firm* — BALLARD SPAHR LLP

(57) ABSTRACT

Disclosed herein, are antibody-polymer-drug conjugates. The conjugate comprises a targeting moiety, one or more polymers, and one or more therapeutic agents. Also described herein, are compositions comprising the conjugates, methods of their preparation, and methods of treating various disorders with the conjugates or their compositions. This abstract is intended as a scanning tool for purposes of searching in the particular art and is not intended to be limiting of the present invention.

12 Claims, 14 Drawing Sheets

Specification includes a Sequence Listing.

(56) References Cited

OTHER PUBLICATIONS

Espacenet translated CN106512003A Description (https://worldwide.espacenet.com/patent/search/family/058325875/publication/CN106512003A?q=CN106512003A) (Year: 2023).*

Zhang et al. "A new construct of antibody-drug conjugates for treatment of B-cell non-Hodgkin's lymphomas" Eur J Pharm Sci May 30, 2017;103:36-46. doi: 10.1016/j.ejps.2017.02.034. Epub Feb. 27, 2017.

Ulbrich et al. "Polymeric drugs on conjugates of synthetic and natural macromolecules; I. Synthesis and physico-chemical characterization", Journal of Controlled Release, 2000, vol. 64 pp. 63-79.

Zhang et al. "N-(2-Hydroxypropyl)methacrylamide Copolymer-Drug Conjugates for Combination Chemotherapy of Acute Myeloid Leukemia", Macromolecular Bioscience, 2016, vol. 16, pp. 121-128.

Zhang et al. "Indium-based and iodine-based labeling of HPMA copolymer-epirubicin conjugates: Impact of structure on the in vivo fate", J Control Release, Aug. 10, 2016, vol. 235, pp. 306-318.

International Search Report and Written Opinion were filed on Dec. 26, 2017 by the International Searching Authority for International Application No. PCT/US2017/056515, which was filed on Oct. 13, 2017, and published as WO 2018/071767, dated Apr. 19, 2018 (Applicant—University of Utah Research Foundation) (23 pages).

International Preliminary Report on Patentability was filed on Apr. 16, 2019 by the International Searching Authority for International Application No. PCT/US2017/056515, which was filed on Oct. 13, 2017, and published as WO 2018/071767, dated Apr. 19, 2018 (Applicant—University of Utah Research Foundation) (19 pages).

U.S. Appl. No. 62/408,512, filed Oct. 14, 2016, Jiyuan Yang.

U.S. Appl. No. 62/449,209, filed Jan. 23, 2017, Jiyuan Yang.

* cited by examiner

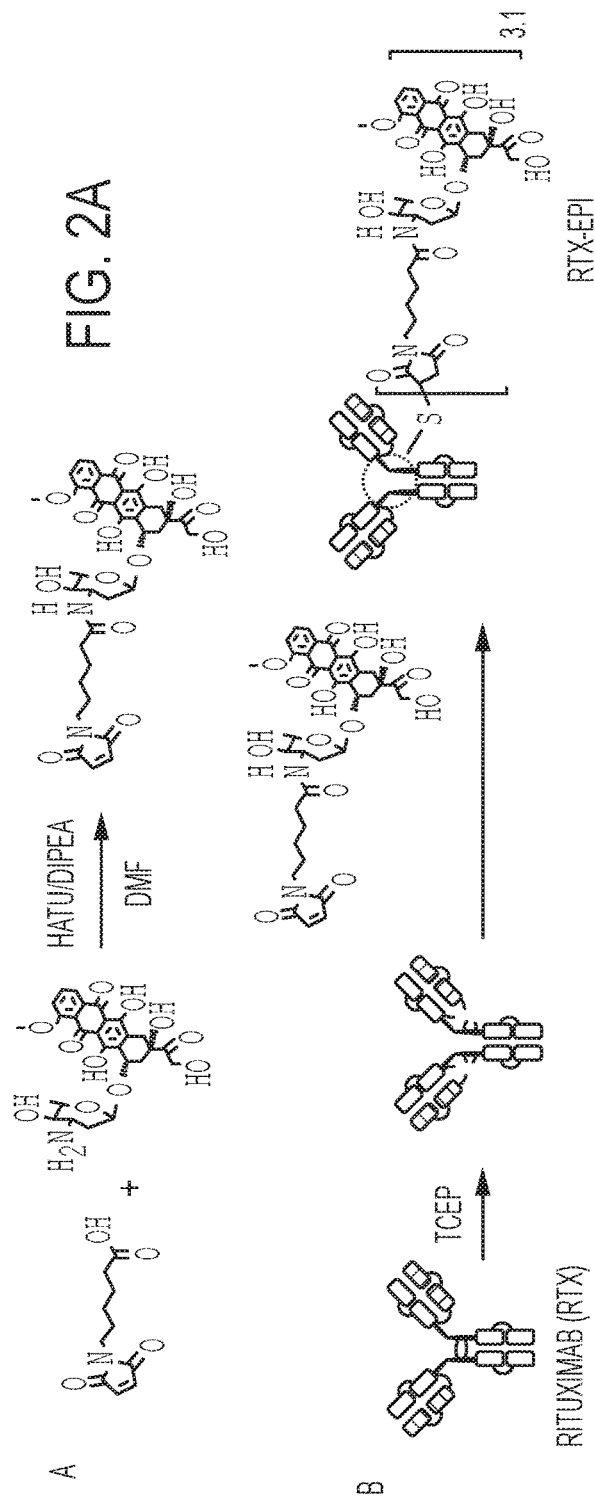
FIG. 2A
FIG. 2B
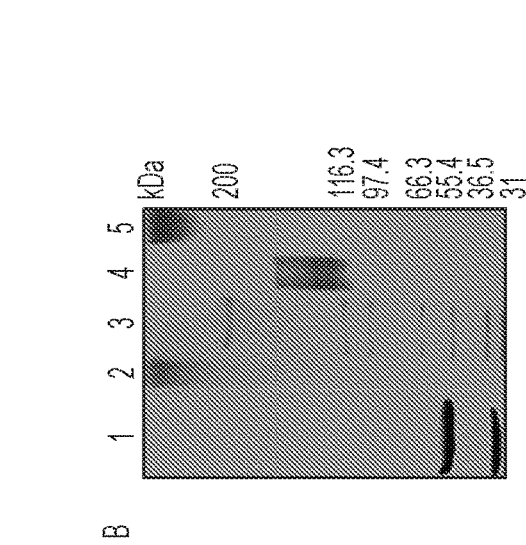
FIG. 3B
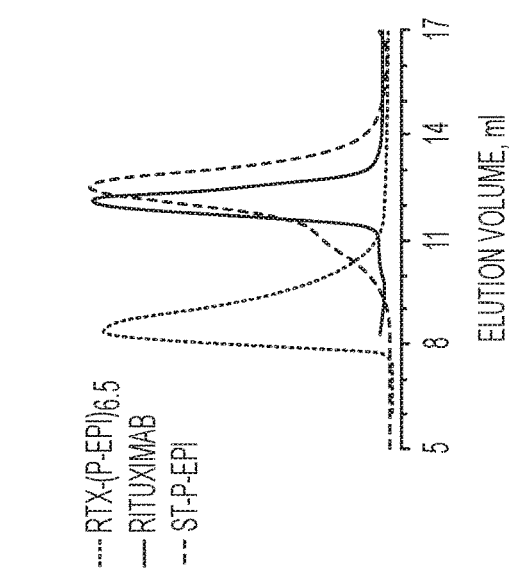
FIG. 3A

| THERAPEUTICS | DOSE (mg/kg) | |
|---|---|---|
| | RTX | EPI |
| RTX | 20 | - |
| RTX-P-EPI | 20 | 1.5 |
| RTX+P-EPI | 20 | 1.5 |
| RTX+EPI | 20 | 1.5 |
| RTX-EPI | 20 | 0.22 |
| IgG-P-EPI | 23[a] | 1.5 |

[a] IgG DOSE.

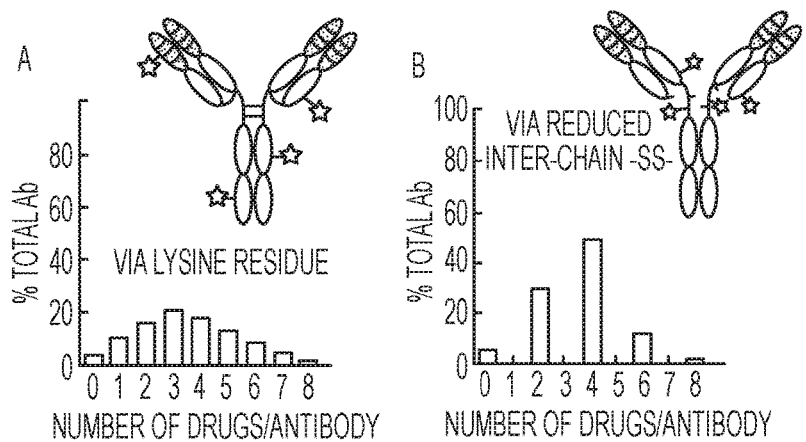
FIG. 16A  FIG. 16B
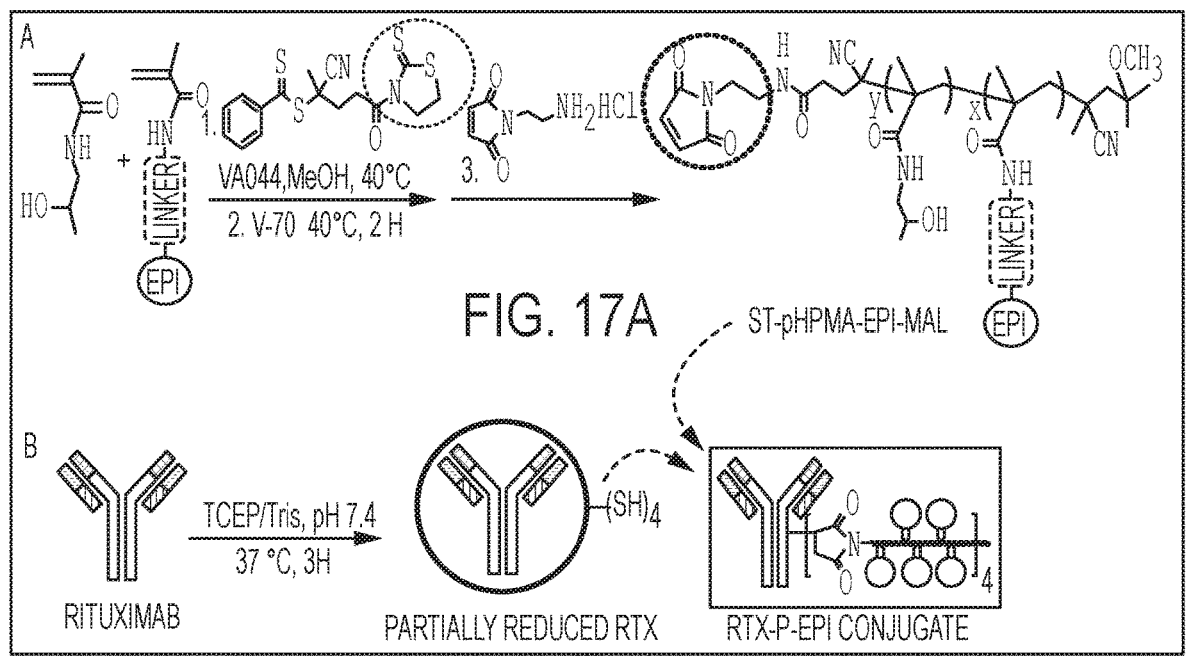
FIG. 17A
FIG. 17B

1:ST-P-PTX; 2:ST-P-FITC; 3:Ab-P-PTX;
4 Ab-P-FITC; 5: mAb-SH; 6: mAb; 7: MARKER.

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Synthetic construct

<400> SEQUENCE: 1

Gly Phe Leu Gly
```

```
<210> SEQ ID NO 2
<211> LENGTH: 4
<212> TYPE: PRT
<213> ORGANISM: Artificial Sequence
<220> FEATURE:
<223> OTHER INFORMATION: Synthetic construct

<400> SEQUENCE: 2

Gly Phe Phe Leu
1

<210> SEQ ID NO 3
<211> LENGTH: 4
<212> TYPE: PRT
<213> ORGANISM: Artificial Sequence
<220> FEATURE:
<223> OTHER INFORMATION: Synthetic construct

<400> SEQUENCE: 3

Gly Leu Leu Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthetic construct

<400> SEQUENCE: 4

Gly Phe Tyr Ala
1

<210> SEQ ID NO 5
<211> LENGTH: 4
<212> TYPE: PRT
<213> ORGANISM: Artificial Sequence
<220> FEATURE:
<223> OTHER INFORMATION: Synthetic construct

<400> SEQUENCE: 5

Gly Phe Gly Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic construct

<400> SEQUENCE: 6

Ala Gly Val Phe
1

<210> SEQ ID NO 7
<211> LENGTH: 4
<212> TYPE: PRT
<213> ORGANISM: Artificial Sequence
<220> FEATURE:
<223> OTHER INFORMATION: Synthetic construct

<400> SEQUENCE: 7

Gly Phe Phe Gly
1
```

```
<210> SEQ ID NO 8
<211> LENGTH: 5
<212> TYPE: PRT
<213> ORGANISM: Artificial Sequence
<220> FEATURE:
<223> OTHER INFORMATION: Synthetic construct

<400> SEQUENCE: 8

Gly Phe Leu Gly Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic construct

<400> SEQUENCE: 9

Gly Gly Phe Leu Gly Phe
1               5
```

ANTIBODY-POLYMER-DRUG CONJUGATES

CROSS-REFERENCE TO RELATED APPLICATIONS

This application is the National Stage Entry under 35 U.S.C. § 371 of International PCT Application No. PCT/US2017/056515, filed Oct. 13, 2017, which claims the benefit of the filing dates of U.S. Provisional Application Nos. 60/408,512, filed Oct. 14, 2016, and 62/449,209, filed Jan. 23, 2017. The content of these earlier filed applications are hereby incorporated by reference in its entirety.

STATEMENT REGARDING FEDERALLY FUNDED RESEARCH

This invention was made with government support under grant numbers GM095606 awarded by the National Institutes of Health. The government has certain rights in the invention.

REFERENCE TO SEQUENCE LISTING

The Sequence Listing submitted herewith as a text file named "21101_0355U2_Sequence_Listing.txt," created on Mar. 18, 2019, and having a size of 4,096 bytes is hereby incorporated by reference pursuant to 37 C.F.R. § 1.52(e)(5).

BACKGROUND

Cancer is one of the leading causes of death in the world. Targeted therapy is one treatment option available to patients involving the administration of drugs such as antibodies that are selective for cancer cells leaving normal cells relatively unharmed. Conventional antibody-drug conjugate technology for cancer is limited in large part because of the adverse effects associated with the use of toxic drugs. Alternative approaches are needed for improving the construction of antibody-drug complexes for targeted disease therapy.

SUMMARY

Disclosed herein are antibody-polymer-drug conjugates, comprising: a targeting antibody; a semitelechelic polymer bonded to the targeting antibody; and a therapeutic agent bonded to the semitelechelic polymer.

Disclosed herein are antibody-polymer-drug conjugates, comprising: a targeting antibody; a semitelechelic polymer bonded to the targeting antibody; and a therapeutic agent bonded to the semitelechelic polymer, wherein the targeting antibody is rituximab, the semitelechelic polymer is N-(2-hydroxypropyl) methacrylamide, and the therapeutic agent is epirubicin.

Disclosed herein are antibody-polymer-drug conjugates, comprising: a targeting antibody; a semitelechelic polymer bonded to the targeting antibody; and a therapeutic agent bonded to the semitelechelic polymer, wherein the targeting antibody is herceptin, the semitelechelic polymer is N-(2-hydroxypropyl) methacrylamide, and the therapeutic agent is epirubicin.

Disclosed herein are antibody-polymer-drug conjugates, comprising: a targeting antibody; a semitelechelic polymer bonded to the targeting antibody; and a therapeutic agent bonded to the semitelechelic polymer, wherein the targeting antibody is OV-TL16, the semitelechelic polymer is N-(2-hydroxypropyl) methacrylamide, and the therapeutic agent is epirubicin.

Disclosed herein are antibody-polymer-drug conjugates, comprising: a targeting antibody bonded to a polymer via a cysteine residue of the antibody; and a therapeutic agent bonded to the polymer via an oligopeptide stable under physiologic conditions and cleaved in lysosomal compartment.

Disclosed herein are pharmaceutical compositions, comprising a targeting antibody; a semitelechelic polymer bonded to the targeting antibody; and a therapeutic agent bonded to the semitelechelic polymer; and a pharmaceutically acceptable carrier.

Disclosed herein are methods of treating cancer in a subject, the method comprising: (a) identifying a patient in need of treatment; and (b) administering to the subject a therapeutically effective amount of the pharmaceutical composition comprising a targeting antibody; a semitelechelic polymer bonded to the targeting antibody; and a therapeutic agent bonded to the semitelechelic polymer; and a pharmaceutically acceptable carrier.

Disclosed herein are methods of making antibody-polymer-drug conjugates, the method comprising the step of reacting a free thiol of the antibody with an electrophilic group on a polymer-drug conjugate, thereby forming the antibody-polymer-drug conjugate.

Disclosed herein are antibody-polymer-drug conjugates, comprising: a targeting antibody bonded to a polymer via a cysteine residue of the antibody; and a therapeutic agent bonded to the polymer via an oligopeptide stable under physiologic conditions and cleaved in lysosomal compartment.

Disclosed herein are antibody-polymer-drug conjugates having the structure:

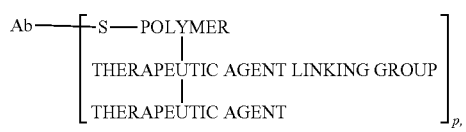

wherein Ab is a targeting antibody; and wherein p is the average number of polymers conjugated to the antibody.

Disclosed herein are antibody-polymer-drug conjugates having the structure:

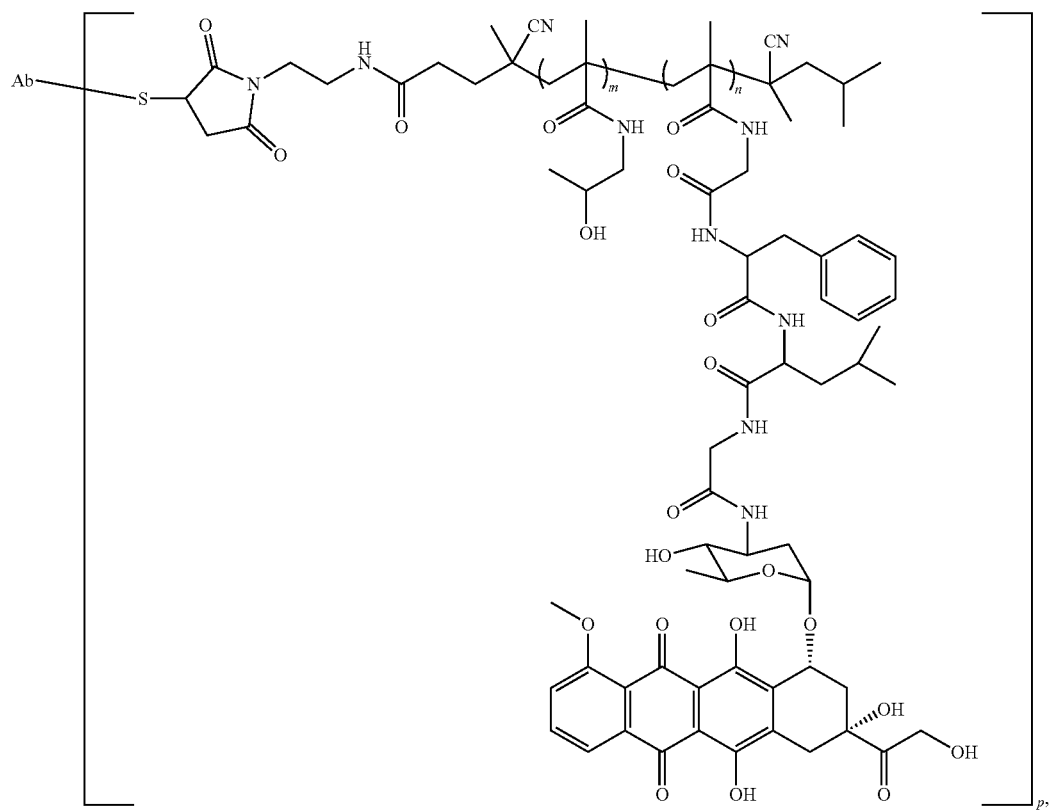

wherein Ab is a targeting antibody; wherein m is the average number of HPMA residues in the polymer; wherein n is the average number of MA-GFLG-EPI residues in the polymer; and wherein p is the average number of polymers conjugated to the antibody.

Disclosed herein are antibody-polymer-drug conjugates having the structure:

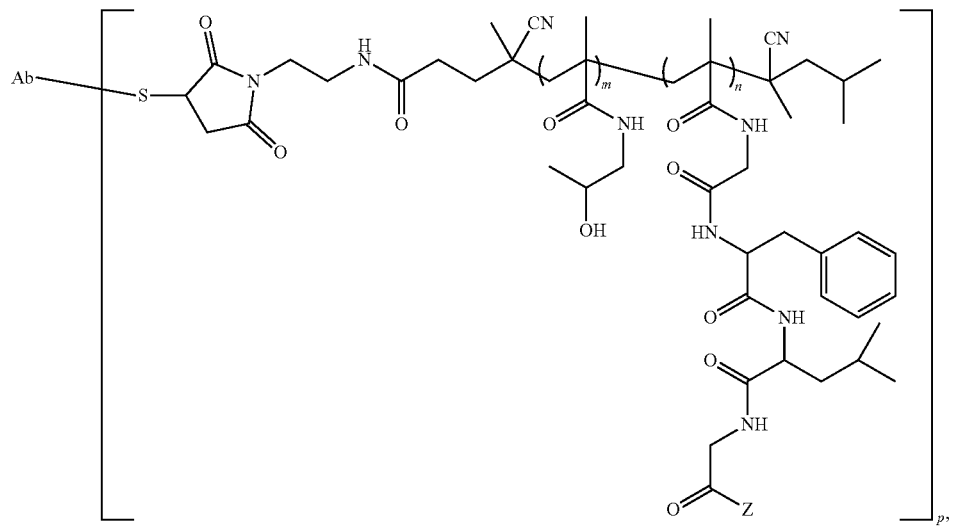

wherein Ab is a targeting antibody; wherein Z is the therapeutic agent; wherein m is the average number of HPMA residues in the polymer; wherein n is the average number of MA-GFLG (SEQ ID NO: 1)-therapeutic agent residues in the polymer; and wherein p is the average number of polymers conjugated to the antibody.

Disclosed herein are antibody-polymer-drug conjugates having the structure:

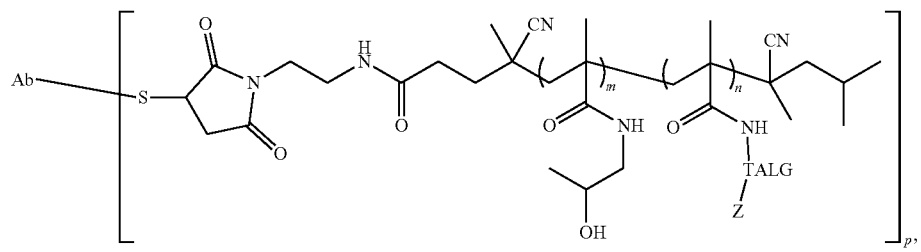

wherein Ab is a targeting antibody; wherein TALG is the therapeutic agent linking group; wherein Z is the therapeutic agent; wherein m is the average number of HPMA residues in the polymer; wherein n is the average number of therapeutic agent linking group-therapeutic agent residues in the polymer; and wherein p is the average number of polymers conjugated to the antibody.

Other features and advantages of the present compositions and methods are illustrated in the description below, the drawings, and the claims.

BRIEF DESCRIPTION OF THE DRAWINGS

FIG. 1A is a schematic showing the production of the chain transfer agent CTA-TT. GFLG corresponds to SEQ ID NO: 1. FIG. 1B illustrates the synthesis of semitelechelic maleimide-functionalized HPMA copolymer-epirubicin conjugate (ST-P-EPI-Mal) and its size exclusion chromatogram. FIG. 1C shows attachment of ST-P-EPI-Mal to a reduced rituximab.

FIGS. 2A-B shows the synthesis of maleimide-modified epirubicin (A) and attachment to rituximab via reduced thiol groups (B).

FIGS. 3A-B shows the SEC and SDS-PAGE analysis of the conjugates. FIG. 3A shows the SEC analysis of ST-P-EPI, RTX and RTX-(P-EPI)$_{6.5}$. FIG. 3B shows the SDS-PAGE analysis of the conjugates staining with Coomassie blue; Lane 1: RTX-EPI (DTT+); Lane 2: IgG-P-EPI; Lane 3: marker; Lane 4: IgG; and Lane 5: RTX-P-EPI.

FIG. 11B shows the biodistribution of $^{125}$I-labeled RTX-P-EPI in Ramos lymphoma-bearing NOD SCID mice at 72 h and 96 h after intravenous administration. Data obtained using the radioactivity count method was plotted as percentage of injected dose per gram of tissue (% ID/g). All data are expressed as mean±standard deviation (n=3).

FIGS. 16A-B shows the impact of the conjugation method on drug loading to an antibody via lysine residue(s) (A) and reduced interchain disulfide bonds (B). Adapted from S. Panowski, S. Bhakta, H. Raab, Paul Polakis and Jagath R Junutula, Site-specific Antibody Drug Conjugates for Cancer Therapy. MAbs. 6, 34-45 (2014).

FIGS. 17A-B show the synthesis of polyHPMA-based antibody-pHPMA-drug conjugates. FIG. 17A shows the synthesis of semitelechelic water-soluble HPMA copolymers (ST-P-EPI) terminated with maleimide at one chain end. FIG. 17B shows controllable reduction of rituximab with TCEP followed by conjugation of ST-P-EPI.

FIG. 22A shows the SEC profiles of OV-TL16 mAb, ST-P-FITC and their conjugates. FIG. 22B shows the SDS-PAGE gel of Ab-polymer conjugates. FIG. 22C shows the results of the flow cytometry analysis of the targeting effect in the SKOV-3 cells treated with FITC-labeled conjugates. FIG. 22D shows the flow cytometry analysis of the apoptosis induction in the SKOV-3 cells treated with PTX-loaded conjugates.

DETAILED DESCRIPTION

Figures 1A, 1B, 1C:
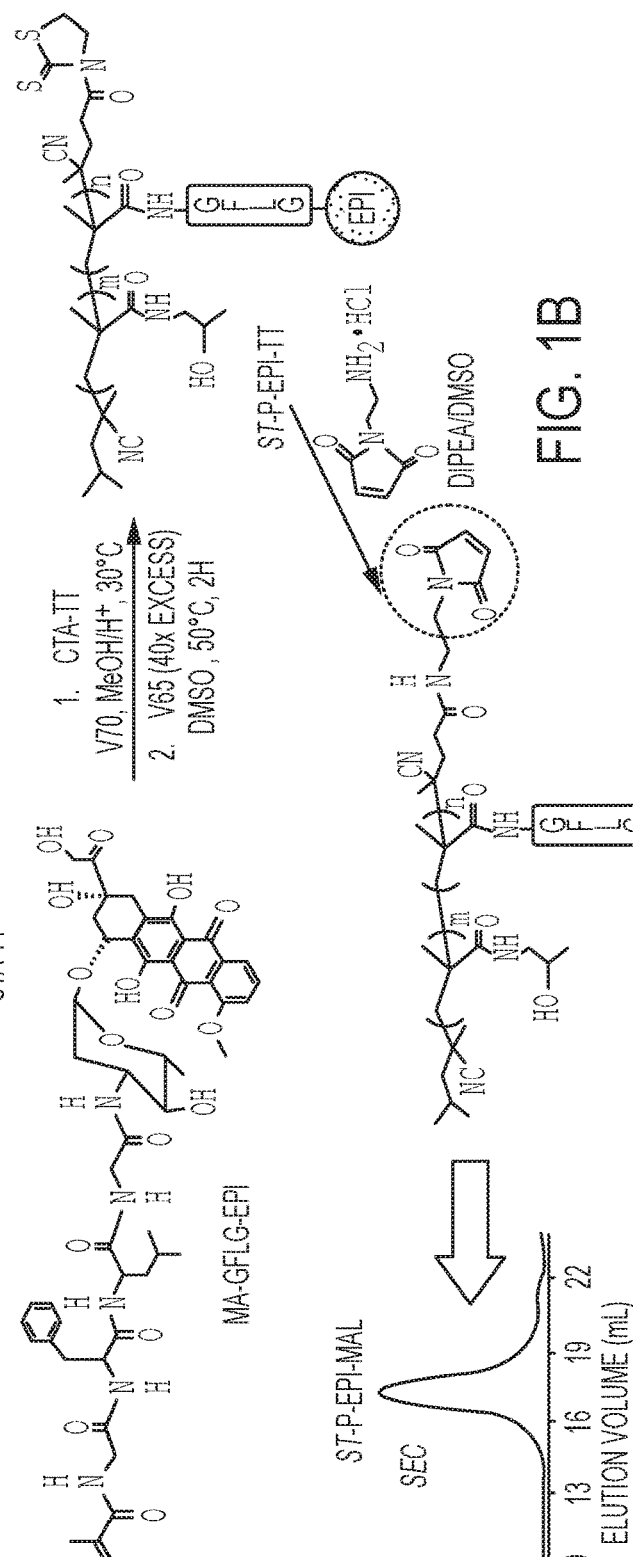
FIGS. 1A-C shows the synthesis of semitelechelic maleimide-functionalized HPMA copolymer-epirubicin conjugate (ST-P-EPI-Mal) and its attachment to rituximab via reduced thiol group.

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "at least one of" is intended to be synonymous with "one or more of" For example, "at least one of A, B and C" explicitly includes only A, only B, only C, and combinations of each.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

In various aspects, a polymer or copolymer can be described as the polymerization product of one or more monomers. For example, a copolymer can be described as the product of coplymerization of N-(2-hydroxypropyl) methacrylamide (HPMA) and 2-hydroxyethyl methacrylate (HEMA) in a 5:1 ratio. As would be readily understood by those of skill, the resultant copolymer would have, on average, 5 residues of HPMA for every 1 residue of HEMA. Again, unless specified to the contrary, the copolymer can be present as an alternating copolymer, a random copolymer, and/or a block copolymer.

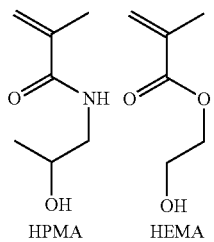

HPMA    HEMA

In various further aspects, a polymer or copolymer can be also described as comprising residues of one or more monomers. For example, a copolymer can be described as comprising residues of HPMA and HEMA in a 5:1 ratio. As would be readily understood by those of skill, m=5, and n=1. Again, unless specified to the contrary, the copolymer can be present as an alternating copolymer, a random copolymer, and/or a block copolymer.

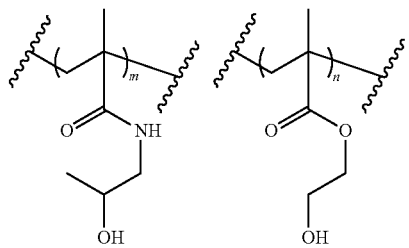

In still further aspects, a polymer or copolymer can be also described as a structure having residues of one or more monomers. For example, a copolymer can be described as a structure having residues of HPMA and HEMA in a 5:1 ratio. As would be readily understood by those of skill, m=5, and n=1.

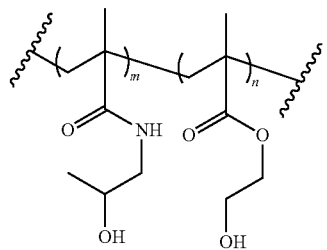

Even though the structure shows the HPMA residues grouped together and shows the HEMA residues grouped together, it would be readily understood by those of skill that the structure depicted is not necessarily a blocky copolymer. Again, unless specified to be a block copolymer, the copolymer can be present as an alternating copolymer, a random copolymer, and/or a block copolymer.

A specific example of a copolymer is shown below. In this example, the copolymer is the product of coplymerization of N-(2-hydroxypropyl)methacrylamide (HPMA) and MA-GFLG-EPI in a 10:1 ratio. As would be readily understood by those of skill, m=10, and n=1.

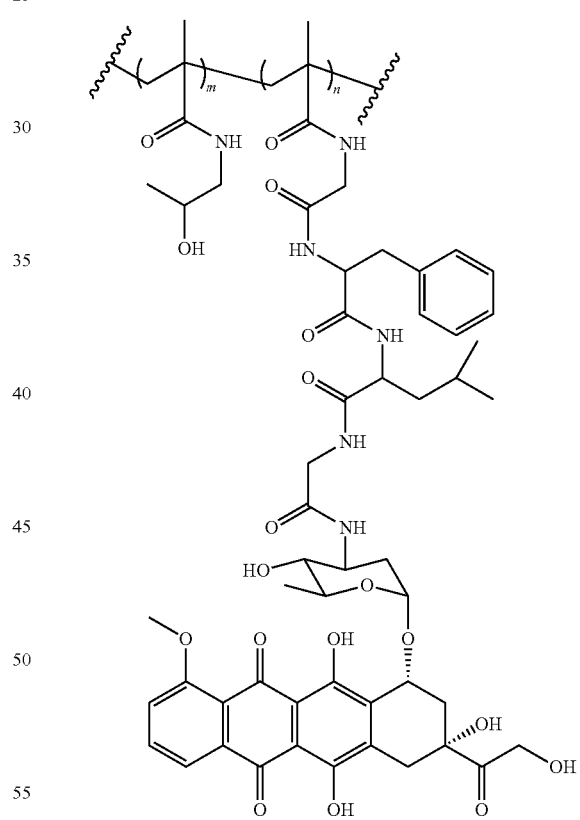

As used herein, the term "oligomer" refers to a relatively low molecular weight polymer in which the number of repeating units is between two and ten, for example, from two to eight, from two to six, or form two to four. In one aspect, a collection of oligomers can have an average number of repeating units of from about two to about ten, for example, from about two to about eight, from about two to about six, or form about two to about four.

As used herein, the term "number average molecular weight" ($M_n$) refers to the common, mean, average of the molecular weights of the individual polymers. $M_n$ can be determined by measuring the molecular weight of n polymer molecules, summing the weights, and dividing by n. $M_n$ is calculated by:

$$\overline{M}_n = \frac{\Sigma_i N_i M_i}{\Sigma_i N_i},$$

wherein $N_i$ is the number of molecules of molecular weight $M_i$. The number average molecular weight of a polymer can be determined by gel permeation chromatography, viscometry (Mark-Houwink equation), light scattering, analytical ultracentrifugation, vapor pressure osmometry, end-group titration, and colligative properties.

As used herein, the term "weight average molecular weight" ($M_w$) refers to an alternative measure of the molecular weight of a polymer. $M_w$ is calculated by:

$$\overline{M}_w = \frac{\Sigma_i N_i M_i^2}{\Sigma_i N_i M_i},$$

wherein $N_i$ is the number of molecules of molecular weight $M_i$. Intuitively, if the weight average molecular weight is w, and a random monomer is selected, then the polymer it belongs to will have a weight of w on average. The weight average molecular weight can be determined by light scattering, small angle neutron scattering (SANS), X-ray scattering, and sedimentation velocity.

As used herein, the terms "polydispersity" and "polydispersity index" (PDI) refer to the ratio of the weight average to the number average ($M_w/M_n$).

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like. The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

Antibody-Drug Conjugates

Non-Hodgkin lymphoma (NHL), a frequent hematologic malignancy, is the 6th most common cancer and the 9th leading cause of cancer death in the United States (Siegel et al., 2016). Treatment of NHL is challenging because the disease comprises over 35 different subtypes with the most prevalent types being diffuse large B cell lymphoma, follicular lymphoma and mantle cell lymphoma (Chu and Polson, 2013). Eighty-five percent of NHLs are of B-cell origin, and more than 95% of B-cell lymphomas bear the cell surface antigen CD20 (Cheson and Leonard, 2008). The discovery of Rituximab (RTX), the first FDA approved monoclonal antibody against CD20, initiated a new era for treatment of B-cell NHLs (Leget and Czuczman, 1998). Its combination with chemotherapy can further enhance the therapeutic activity and still serves as clinical golden standard (Zelenetz et al., 2014). With the development of new, more active modern chemotherapy protocols and targeted therapies, much progress has been made over the past two decades (Mehta and Forero-Torres, 2015; Richter et al., 2016; Seyfizadeh et al., 2016). Unfortunately, besides adverse side effects, relapsed or resistant disease remains a major cause of treatment failure. The nonresponsiveness and/or resistance have been attributed to the inability of immune effector cells to hypercrosslink ligated mAbs, and Fc receptor-mediated endocytosis or "trogocytosis" of CD20 antigens (Chu and Kopeček, 2015). Thus, the need for new therapeutic strategies that combine high levels of efficacy with improved tolerability is evident.

One strategy is the development of highly 'specific' drugs that accumulate in and kill tumor cells to achieve tumor eradication without systemic toxicity. Antibody-drug conjugates (ADCs) are such an approach that allows for targeted delivery of cytotoxic agents to antigen-expressing tumor cells (Chari et al., 2014; Jagadeesh and Smith, 2016). ADCs have three components: the antibody (Ab), linker and drug/toxin (Ducry and Stump, 2010). The concept of using Ab for drug delivery is not new, however, the design of an ADC remains challenging, as it involves multiple factors, for example, selection of an antibody, the stability of a linker, the payload and its cleavage kinetics, etc. Among them an important parameter is payload number on a single antibody (drug-antibody ratio or DAR), because over-attachment will disturb mAb immunoaffinity. Generally, a limited number of toxin moieties can be attached to one Ab molecule (usually DAR is 4-6). Consequently, extremely toxic agents such as calicheamycin or auristatin monomethyl ester (MMAE) with $IC_{50}$<1 nM have to be employed in order to obtain sufficient efficacy for target cell death (Casi and Neri, 2012; Wu and Senter, 2005). Therefore, even a little fraction off-target conjugate will result in serious adverse effects.

Development of ADCs for B-cell NHL is rational, because NHL has been treated clinically with either chemotherapy or immunotherapy (e.g., RTX), or their combination; it is thought that the tumor cells will be responsive to cytotoxic agents delivered by an ADC. Given the fact that RTX has been used in clinical practice for over two decades, the antibody and the target have been validated. Moreover, the efficacy of RTX has been increased when used in combination with chemotherapy, thus RTX-based ADCs may provide potential synergism. However, it has been reported that directly conjugated conventional chemotherapy drugs such as doxorubicin (DOX) to an Ab have failed due to lack of cytotoxic potency (Braslawsky et al, 1991; Tolcher et al., 1999). HPMA copolymer-DOX conjugates were attached to RTX but did not enhance treatment activity in vivo when compared to controls (Lidický et al., 2015).

From the structure-function point of view, antibody-drug conjugates belong to the "targeted chemotherapeutics" category of anti-cancer drugs. Historically, antibody and/or antibody Fab' fragment have been incorporated into water-soluble polymer-anticancer drug conjugates as targeting moieties to improve the therapeutic outcome and to reduce the toxicity of anticancer agents (Říhová et al., 1985, 1988, 2002; Pimm et al., 1993; Omelyanenko et al., 1996; Hongrapipat et al., 2008; Lu et al., 1999, 2003; Shiah et al., 2001; Jelínková et al., 1998; Kovář=et al., 2002; Chytil et al., 2010; Pola et al., 2013). For example, a comparison of the efficacy between non-targeted and OV-TL16 mAb fragment-targeted HPMA copolymer-mesochlorin $e_6$ conjugates (P-Mce$_6$ vs P-Fab'-Mce$_6$) for treatment of OVCAR-3 xenografts in nude mice has been performed. Results clearly indicate the advantage of targeted treatment (Lu, et al., 1999, 2003). Omelyanenko et al. (1996) performed detailed studies to investigate the impact of conjugation chemistry on binding affinity of modified antibody conjugates. Differences in Ka (affinity constant) suggested random modification of lysine residues via amide bond lead to conjugate heterogeneity and impaired antigen binding; site-specific modification results in superior property. However, unlike classic ADCs in which monoclonal antibody itself can induce cancer cell death, an antibody (or antibody fragment) in the aforementioned early studies served as targeting moiety, and did not have therapeutic function.

Despite a growing number of ADCs currently in clinical trials or preclinical development, there still remains space to explore new approaches for the treatment of hematologic malignancies. For example, a new therapy that combines high efficacy with enhanced tolerability is needed. Efficacy and safety are two major issues. Due to limited attachment sites, in current ADCs, more and more potent toxins ($IC_{50}$ from nmol to pmol) are being investigated to achieve DAR 2 (2 toxins conjugated to one mAb). Such strategy raises toxicity concerns. It was reported recently that six patients with acute myeloid leukemia (AML) have been identified with liver toxicities in clinical trials and four of them have died.

Antibody-Polymer-Drug Conjugates

Described herein, are methods to generate therapeutically efficient ADCs by using semitelechelic HPMA copolymer-epirubicin conjugates attached to RTX, resulting in multiple drugs or therapeutic agents bound to an Ab to enhance overall cytotoxicity and treatment efficacy of an ADC but without adding attachment sites. The antigen-targeting ability and pharmacokinetics of an antibody-polymer-drug conjugate (APDC), such as RTX-P-EPI, are preserved. The APDCs described herein possess the features of both antibody-drug conjugates with high specificity and advantages of macromolecular therapeutics. Described herein, is the therapeutic activity of the APDCs disclosed herein using in vitro and in vivo assays.

Semitelechelic (ST) polymers are linear macromolecules having a reactive functional group at one end of the polymer chain (Kamei and Kopeček, 1995). The single functional group provides the opportunity to conjugate or graft the macromolecule to other species or surfaces (Lu et al., 1998). ST-HPMA copolymers have been used in the synthesis of star copolymers, e.g., by attachment to amino groups of dendrimers (Wang et al., 2000) or for modification of antibodies. The chemistries used for the antibody modification can vary. The synthesis of antibody polymer conjugates by reaction with polymer precursors containing several attachment points, results in partially crosslinked conjugates containing antibody molecules and several polymer chains (Říhová and Kopeček, 1985; Tappertzhofen et al., 2013; Kovář et al. 2002). The use of ST-copolymers results in well-defined conjugates where one antibody molecule is decorated with several polymer chains (Kovář et al. 2002; Etrych et al., 2009; Tappertzhofen et al., 2014; Lidický et al., 2015). The attachment of polymer chains is performed either non-specifically by reaction of ST polymers with accessible amino groups of lysine (Kovář et al. 2002) or more specifically by reduction of the antibody disulfide bonds and attachment of ST copolymer via thiol-ene reaction (Etrych et al., 2009; Lidický et al., 2015). Alternatively, the amino groups of lysine may be modified (non-specifically) by 2-iminothiolane and the ST polymer attached via thiol-ene reaction (Etrych et al., 2007, 2009).

As disclosed herein, a new generation antibody-drug conjugates (ADCs) that integrated two traditional approaches (antibody targeting and polymer therapeutics) into one 'hybrid' product with the potential to enhance treatment efficacy and improve tolerability for patients, for example, patients with B-cell lymphomas. For example, a conventional cytotoxic agent epirubicin was incorporated onto HPMA polymer carrier by a controlled living polymerization technique, resulting in a well-defined semitelichelic maleimide functionalized polymer-drug conjugate. This precursor was attached to RTX, a chimeric anti-CD20 mAb, to generate a new type of ADC, RTX-P-EPI, termed APDC. Previously, RTX has been conjugated with both free drug doxorubicin (DOX) (Braslawsky et al, 1991), liposomal Dox (Sapra and Allen, 2002), and HPMA copolymer-DOX conjugates (Lidický et al., 2015). Unfortunately, these antibody-drug conjugates were found to possess no additive therapeutic effect. Initially, the failure was explained by the CD20 non-internalization property. However, Law et al. (2004) evaluated a RTX-based ADC using MMAE, whose $IC_{50}$ is 50-200 folds lower than that of DOX. Interestingly, internalization of the conjugate was demonstrated and the antitumor efficacy of the conjugate (RTX-vcMMAE) in a xenograft model of CD20-positive lymphoma was proved. Internalization of iron oxide nanoparticles targeted with CD20+ single chain variable fragment antibody-streptavidin fusion protein in the MC126 B lymphoma cell line was also observed (Wang et al., 2013). As disclosed herein, the internalization and antitumor efficacy of the conjugate, RTX-P-EPI, was established and is described in detail herein.

One of the barriers for RTX clinical application is the resistance. Rituximab resistance pathways remain uncertain. One of the key factors for resistance development is frequently repeated relatively high doses. The mechanistic factors involved are the altered signaling, resulting in the overexpression of anti-apoptotic proteins of the Bcl-2 family and leading to resistance to apoptosis. Disclosed herein are the results of comparing the mixture of RTX with the polymer-drug conjugate (P-EPI), in which the APDC, RTX-P-EPI, showed 1.5 times higher in vitro cytotoxicity and significantly delayed tumor growth. This higher in vitro cytotoxicity and in vivo anti-tumor efficacy indicated a synergistic effect. EPI is reported to up-regulate Bax and Bak (the pro-apoptotic Bcl-2 family proteins); this may re-sensitize resistant cells to rituximab-mediated apoptosis. Therefore, the results described herein suggest that APDC disclosed herein possesses synergistic potential of immunotherapy combined with established macromolecular therapy. Moreover, a conventional chemo-agent could be utilized to generate highly effective APDCs and concomitantly reduce the risk of off-target toxicity.

Compositions

Described herein are antibody-polymer-drug conjugates (APDCs). The antibody-polymer-drug conjugates can comprise a targeting antibody; one or more therapeutic agents; and one or more polymers. The one or more polymers can be one or more semitelechelic polymers. Each of the semitelechelic polymers can have an antibody-linking end group at a functional terminus such that one or more of the semitelechelic polymers can be linked, conjugated or bonded to the targeting antibody via the antibody-linking end group. The one or more therapeutic agents can be, conjugated, linked or bonded to each of the one or more of the semitelechelic polymers via a therapeutic agent linking group. In an aspect, the antibody-polymer-drug conjugates comprise a targeting antibody, a semitelechelic polymer, and a therapeutic agent. In an aspect, the semitelechelic polymer can be bonded to the targeting antibody. In an aspect, the therapeutic agent can be bonded to the semitelechelic polymer.

In certain aspects, an antibody-polymer-drug conjugate comprises a targeting antibody bonded to a polymer via a cysteine residue of the antibody; and a therapeutic agent bonded to the polymer via an oligopeptide stable under physiologic conditions and cleaved in lysosomal compartment. In one aspect, the antibody is bonded to the polymer via reaction of a free thiol with an electrophilic group on the polymer. In some aspects, the polymer is a copolymer of N-(2-hydroxypropyl)methacrylamide, 2-hydroxyethyl methacrylate, diethylene glycol monomethacrylate, triethylene glycol monomethacrylate, acrylonitrile, methacrylonitrile, acrylamide, methacrylamide, N-alkylmethacrylamide, N-alkylacrylamide, N,N-dialkylacrylamide, methacrylic acid, acrylic acid, esters of acrylic acid, esters of methacrylic acid, N,N-diethylaminoethyl methacrylate, N-vinylpyrrolidone, or norbornene, or combinations thereof. For example, the polymer can comprise residues of monomers of an acrylamide connected to the therapeutic agent via the oligopeptide (e.g., glycylphenylalanylleucylglycine).

In further aspects, the acrylamide connected to the therapeutic agent via the oligopeptide is MA-GFLG-EPI and has the structure:

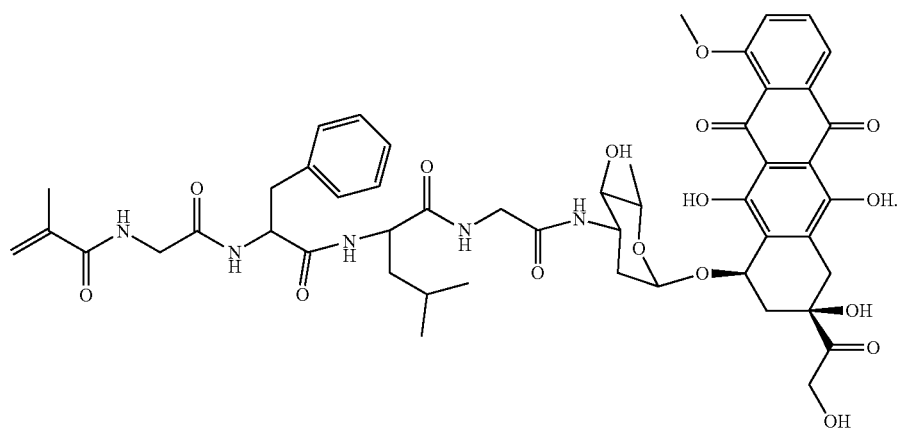

MA-GFLG-EPI

In still further aspects, the polymer has the structure:

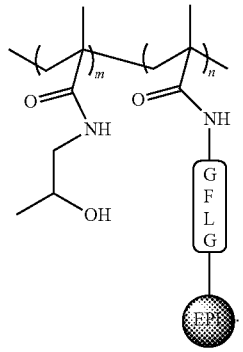

In an even further aspect, the conjugate has the structure:

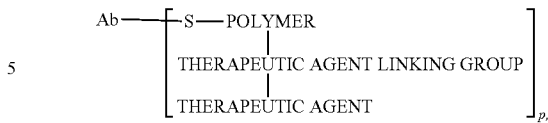

wherein Ab is a targeting antibody; and wherein p is the average number of polymers conjugated to the antibody. In some aspects, the polymer can comprise residues of monomers of an acrylamide connected to the therapeutic agent via the therapeutic agent linking group (e.g., an oligopeptide). In some aspects, the polymer comprises residues of N-(2-hydroxypropyl)methacrylamide (HPMA). In some aspects, the therapeutic agent is selected from epirubicin, doxorubicin, daunorubicin, idarubicin, paclitaxel, nab-paclitaxel, 10-deacetylbaccatin III, baccatin III, paclitaxel C, and 7-epi-paclitaxel.

In certain aspects, the conjugate has the structure:

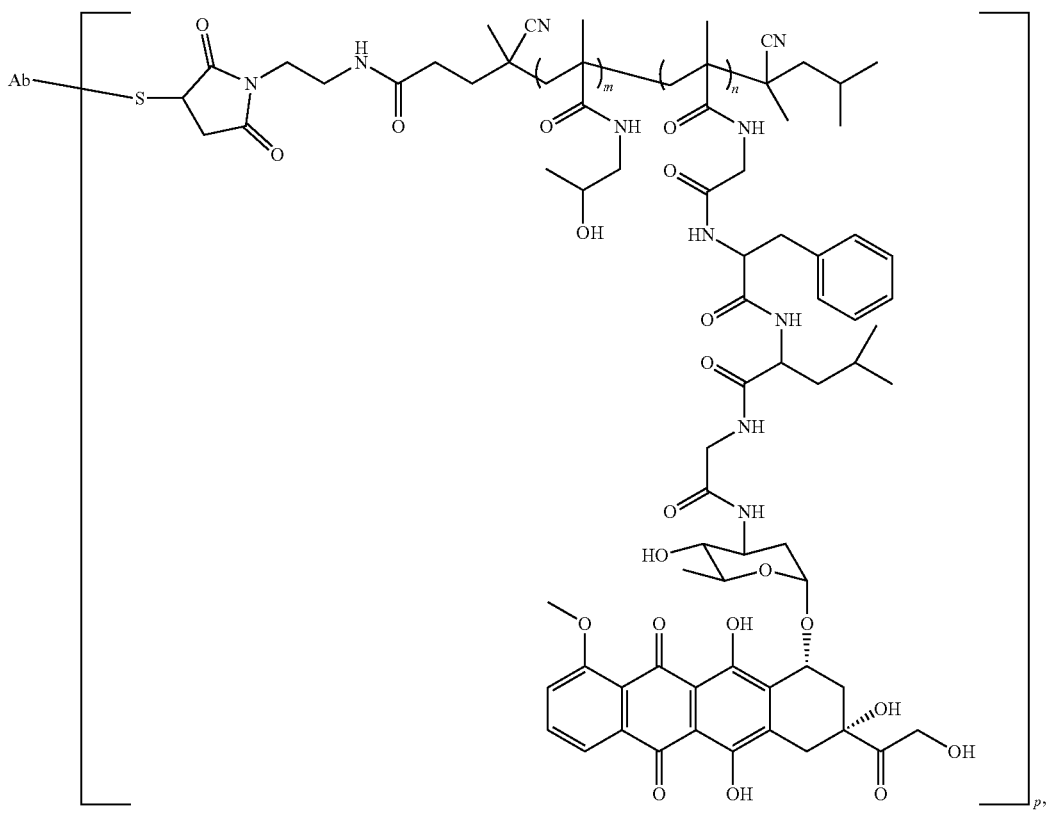

wherein Ab is a targeting antibody; wherein m is the average number of HPMA residues in the polymer; wherein n is the average number of MA-GFLG (SEQ ID NO: 1)-EPI residues in the polymer; and wherein p is the average number of polymers conjugated to the antibody.

In a further aspect, the conjugate has the structure:

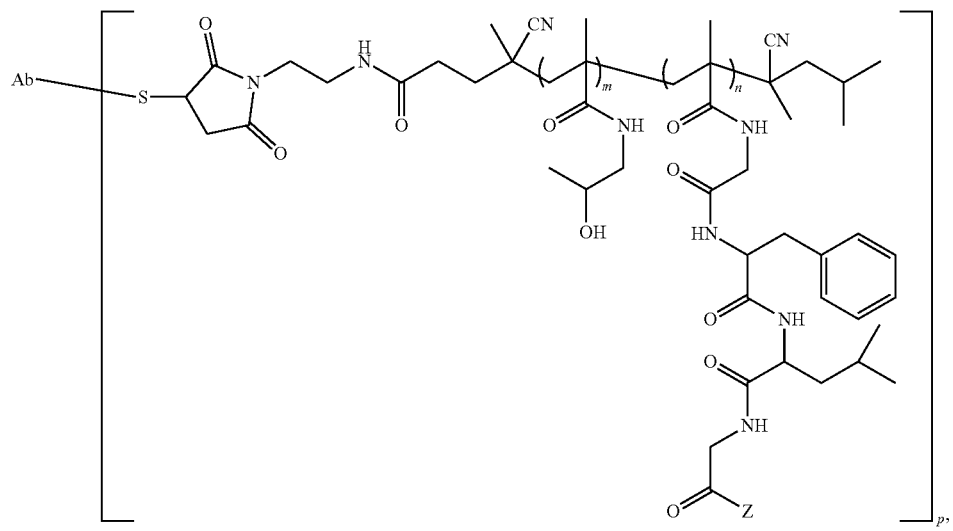

wherein Ab is a targeting antibody; wherein Z is the therapeutic agent; wherein m is the average number of HPMA residues in the polymer; wherein n is the average number of MA-GFLG (SEQ ID NO: 1)-therapeutic agent residues in the polymer; and wherein p is the average number of polymers conjugated to the antibody.

In a still further aspect, the conjugate has the structure:

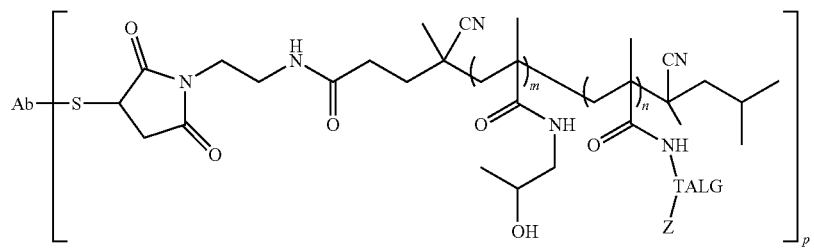

wherein Ab is a targeting antibody; wherein TALG is the therapeutic agent linking group; wherein Z is the therapeutic agent; wherein m is the average number of HPMA residues in the polymer; wherein n is the average number of therapeutic agent linking group-therapeutic agent residues in the polymer; and wherein p is the average number of polymers conjugated to the antibody.

Targeting Antibody.

In some aspects, the targeting antibody of the antibody-polymer-drug conjugate can be an antibody or a biologically active variant thereof. In some aspects, the targeting antibody can be any antibody having one or more interchain disulfide bonds. In some aspects, the targeting antibody can be any antibody comprising one or more interchain disulfide bonds in the antibody hinge region. One or more of the disulfide bonds can be reduced to sulfhydryl groups that can serve as a point of attachment for one or more polymers (e.g., semitelechelic). In some aspects, the attachment of the polymers (e.g., semitelechelic) described herein to the targeting antibody via the sulfhydryl groups can generate a relatively homogenous APDC.

In some aspects, the targeting antibody can have a molecular weight of greater than 100 kDa. In some aspects, the targeting antibody can have a weight average molecular weight (Mw) of from about 40,000 g/mol to about 160,000 g/mol. In other aspects, the targeting antibody can have an Mw of from about 140,000 g/mol to about 155,000 g/mol. In some aspects, the targeting antibody can have an Mw of from about 50,000 to 170,000 g/mol.

In some aspects, the targeting antibody can be a rabbit, mouse, a human, a chimeric, a humanized, fully human monoclonal antibody or a biologically active variant thereof. The antibody can be a naturally expressed antibody (e.g., a tetrameric antibody) or a biologically variant thereof. In some aspects, the targeting antibody can be a non-naturally occurring antibody (e.g., diabody) or a biologically active variant thereof. The antibody can also be further engineered.

In some aspects, the targeting antibody can be an IgG antibody. WO/2016/064749 discloses IgG antibodies that may useful as the targeting antibody of the present application. The content of WO/2016/064749 is hereby incorporated herein by reference for its teaching of IgG antibodies that can be used in the disclosed compositions. In an aspect, the targeting antibody can be an IgG1 isotype. In other aspects, the targeting antibody can be an IgG2, IgG3 or and IgG4 isotype.

In some aspects, the antibody-polymer-drug conjugates described herein comprise a targeting antibody, wherein the targeting antibody binds to a B-lymphocyte antigen. Accordingly, in some embodiments, the targeting antibody binds to the CD20 antigen. In an aspect, the targeting antibody can be an anti-CD20 monoclonal antibody. Examples of anti-CD20 monoclonal antibodies include, but are not limited to rituximab, ofatumumab, tositumomab, obinutuzumab, ibritumomab, or a biologically active variant thereof. In an aspect, the targeting antibody can be rituximab.

In some aspects, the antibody-polymer-drug conjugates described herein comprise a targeting antibody, wherein the targeting antibody binds to an epidermal growth factor receptor. Accordingly, in some embodiments, the targeting antibody binds to the HER2 (human epidermal growth factor receptor 2) receptor. In an aspect, the targeting antibody can be an anti-HER2 monoclonal antibody. Examples of anti-HER2 monoclonal antibodies include, but are not limited to trastuzumab or pertuzumab, or a biologically active variant thereof. In an aspect, the targeting antibody can be trastuzumab.

In some aspects, the antibody-polymer-drug conjugates described herein comprise a targeting antibody, wherein the targeting antibody binds to an OA-3 antigen. In an aspect, the targeting antibody can be an anti-OA-3 monoclonal antibody. Examples of anti-OA-3 monoclonal antibodies include, but are not limited to OVTL-16, or a biologically active variant thereof. In an aspect, the targeting antibody can be OVTL-16.

The targeting antibody can be selected to target or bind to an antigen that is present in a particular disease state or adverse health condition. As such, there are a number of suitable targeting antibodies that can be employed, depending on the condition for which a subject is to be treated. More generally, the targeting antibody can be a therapeutic agent, such as an anti-cancer agent. In some aspects, the targeting antibody can have a therapeutic effect.

In some aspects, the targeting antibody can be abciximab, adalimumab, alemtuzumab, basiliximab, belimumab, bevacizumab, brentuximab, canakinumab, cetuximab, daclizumab, efalizumab, gemtuzumab, golimumab, ibritumomab, infliximab, ipilimumab, motavizumab, obinutuzumab, ofatumumab, omalizumab, OV-TL-16, palivizumab, pertuzumab, ranibizumab, raxibacumab, rituximab, tociliuzmab, trastuzumab, or ustekinumab.

Polymers. Disclosed herein are antibody-polymer-drug conjugates comprising a targeting antibody, one or more therapeutic agents, and one or more polymers. A wide variety of polymers can be incorporated into the antibody-polymer-drug conjugate. In some aspects, the one or more polymers can be a semitelechelic polymer. Examples of semitelechelic polymers can include a monomer of N-(2-hydroxypropyl) methacrylamide, 2-hydroxyethyl methacrylate, diethylene glycol monomethacrylate, triethylene glycol monomethacrylate, acrylonitrile, methacrylonitrile, acrylamide, methacrylamide, N-alkylmethacrylamide, N-alkylacrylamide, N,N-dialkylacrylamide, methacrylic acid, acrylic acid, esters of acrylic acid, esters of methacrylic acid, N,N-diethylaminoethyl methacrylate, N-vinylpyrrolidone, norbornene, or combinations thereof (where alkyl groups can include from 1 to 6 carbon atoms and can optionally include from 1 to 3 OH-groups). In some additional examples, each of the plurality of semitelechelic polymers can include at least 45 mol % of a N-(2-hydroxypropyl) methacrylamide (HPMA) monomer, a monomer having a structure according to Formula I:

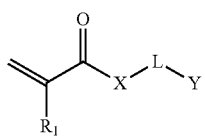

wherein $R_1$ is hydrogen or methyl, X is oxygen or $NR_1'$ (wherein $R_1'$ is hydrogen or an alkyl group), L is an alkyl group or an aryl group, and Y is a hydrophilic group (e.g., —OH, —$NHR_1'$, —$NH_2$, or —SH) or a combination of HPMA and a monomer having a structure according to Formula I. A variety of other monomers can also be used to prepare the semitelechelic polymers. In an aspect, the semitelechelic polymers can be N-(2-hydroxypropyl)methacrylamide (HPMA). In an aspect, each of the semitelechelic polymers comprises N-(2-hydroxypropyl)methacrylamide (HPMA).

The one or more polymers can each be one or more semitelechelic polymers. In an aspect, the one or more semitelechelic polymers can be connected to both the targeting antibody and to the one or more therapeutic agents. In an aspect, each of the one or more therapeutic agents can be independently connected to the targeting antibody via the one or more semitelechelic polymers.

In some aspects, each of the one or more of semitelechelic polymers can include an antibody-linking end group at the functional terminus. Of the two termini of a semitelechelic polymer, one can be functional. Thus, the antibody-linking end group can be attached at the sole functional terminus of the semitelechelic polymer. A variety of antibody-linking end groups can be used. Examples of the antibody-linking end group include but are not limited to

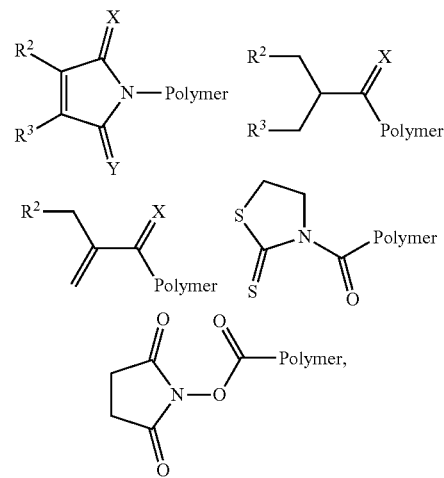

or combinations thereof, wherein $R^2$ and $R^3$ can be independently selected from H, I, Br, Cl, $C_6H_5S$, $CH_3C_6H_5S$, or Ts, X and Y can be independently selected from NH, O, S, or Se, Z can include N or C, and "Polymer" represents the semitelechelic polymer to which the antibody-linking end group can be linked, conjugated to or bonded. In an aspect, the antibody-linking end group can be maleimide.

As described above, the one or more of the disulfide bonds present on the targeting antibody can be reduced to sulfhydryl groups and serve as a point of attachment for the one or more polymers (e.g., semitelechelic). In some aspects, the targeting antibody can include, on average, from about 2 polymers to about 8 polymers. In some aspects, the targeting antibody can include, on average, from about 3 to about 7 polymers. In some aspects, the targeting antibody can include, on average, from about 2 to about 4, from about 3 to about 5, from about 4 to about 6, or from about 5 to about 7 polymers. In some aspects, each of the one or more polymers can be a semitelechilic polymer.

In some aspects, each of the one or more of the semitelechelic polymers can include one or more therapeutic agents. In an aspect, the one or more therapeutic agents can be connected, linked, conjugated or bonded to each of the one or more semitelechelic polymers via a therapeutic agent linking group. In some aspects, the one or more therapeutic agents can be linked via the therapeutic agent linking group to a therapeutic agent-bearing monomer that is incorporated into each of the one or more semitelechelic polymers via copolymerization. The therapeutic agent-bearing monomer can include a variety of suitable monomers, such as those described above. In an aspect, the therapeutic agent-bearing monomer can include methacrylamide or a derivative thereof (e.g. N-alkylmethacrylamide, etc.). Examples of therapeutic agent linking groups include but are not limited to Gly-Gly, Gly-Phe-Gly, Gly-Phe-Phe, Gly-Leu-Gly, Gly-Val-Ala, Gly-Val-Leu, Gly-Val-Phe, Gly-Phe-Ala, Gly-Leu-Phe, Gly-Leu-Ala, Gly-Ile-Ala, Ala-Val-Ala, Ala-Val-Phe, Ala-Phe-Val, Gly-Phe-Leu-Gly (SEQ ID NO: 1), Gly-Phe-Phe-Leu (SEQ ID NO: 2), Gly-Leu-Leu-Gly (SEQ ID NO: 3), Gly-Phe-Tyr-Ala (SEQ ID NO: 4), Gly-Phe-Gly-Phe (SEQ ID NO: 5), Ala-Gly-Val-Phe (SEQ ID NO: 6), Gly-Phe-Phe-Gly (SEQ ID NO: 7), Gly-Phe-Leu-Gly-Phe (SEQ ID NO: 8), Gly-Gly-Phe-Leu-Gly-Phe (SEQ ID NO: 9), N-aminocaproyl-Val-citruline, or combinations thereof.

In some aspects, each of the one or more of the semitelechelic polymers can include, on average, from 2 to 12 therapeutic agents. In some aspects, each of the one or more of the semitelechelic polymers can include, on average, from 4 to 8 therapeutic agents. In some aspects, each of the one or more of the semitelechelic polymers can include, on average, from 3 to 5, from 4 to 6, or from 5 to 7 therapeutic agents. In some aspects, each of the one or more of the semitelechelic polymers bonded or linked to the targeting antibody can include the same or different therapeutic agents. For example, a single targeting antibody can be bonded to a plurality (or one or more) semitelechelic polymers, wherein each of the semitelechelic polymers comprises the same or different therapeutic agents.

To further increase the homogeneity of the APDC described herein, the polymerization technique employed to prepare, for example, the semitelechelic polymer, can be one that will result in a uniform polymer product. Any polymerization technique that will produce a highly uniform or homogenous, for example, semitelechelic polymer, can be used and is considered within the scope of the present disclosure. In an aspect, a reversible addition-fragmentation chain transfer (RAFT) polymerization technique can be used to generate a uniform or homogenous semitelechelic polymer. In an aspect, atom transfer radical polymerization (ATRP) can be used to generate a uniform or homogenous semitelechelic polymer. In a further aspect, nitroxide-mediated polymerization (NMP) can be used to generate a uniform or homogenous semitelechelic polymer. These are living or controlled radical polymerization techniques and make use of a chain transfer agent to afford control over the generated molecular weight and polydispersity during a free-radical polymerization. In fact, these polymerizations can be performed under conditions to favor low dispersity (molecular weight distribution) and a pre-chosen molecular weight.

In some aspects, the semitelechelic polymer can have a number average molecular weight (Mn) of from about 25,000 g/mol to about 45,000 g/mol. In some aspects, the semitelechelic polymer can have an Mn of from about 30,000 g/mol to about 40,000 g/mol. In some aspects, each of the one or more semitelechelic polymers has a molecular weight ranging from about 2 kDa to about 40 kDa. In some aspects, each of the one or more semitelechelic polymers comprises N-(2-hydroxypropyl)methacrylamide (HPMA) having a molecular weight ranging from about 20 kDa to about 50 kDa. In some aspects, each of the one or more semitelechelic polymers has a molecular weight ranging from about 2 kDa to about 60 kDa.

Thus, by controlling the attachment cites for the semitelechelic polymer to the targeting antibody, and by controlling the polydispersity of the semitelechelic polymer itself, a homogenous APDC as described herein can be generated. In some aspects, the semitelechelic polymer can have a polydispersity of less than or equal to 1.45, 1.40, 1.35, 1.30, 1.25, 1.20, 1.19, 1.18, 1.17. 1.16, 1.15, or lower. In an aspect, the one or more semitelechelic polymers can have a polydispersity of less than or equal to 1.45. In some aspects, the APDC can have a polydispersity of less than or equal to 1.45, 1.40, 1.35, 1.30, 1.25, or lower. In an aspect, the antibody-polymer-drug conjugate can have a polydispersity of less than or equal to 1.45. In an aspect, the antibody-polymer-drug conjugate can have a polydispersity of less than or equal to 1.8. In an aspect, the one or more semitelechelic polymers can have a polydispersity of less than or equal to 1.45. In an aspect, the antibody-polymer-drug conjugate can have a polydispersity of between 1.10 and 1.45. In an aspect, the antibody-polymer-drug conjugate can have a polydispersity of between 1.10 and 1.8.

The disclosure further features antibody-polymer-drug conjugates as described herein comprising two or more polymers that are different (i.e., the polymers of a single antibody-polymer-drug conjugates can be a combination of more than one type of polymer). Such antibody-polymer-drug conjugates, comprising more than one type of polymer, can capture different types of therapeutic agents in a single formulation, and thus, can deliver different therapeutic agents. In some aspects, the two or more of the polymers can be the same but have different therapeutic agent linking groups so as to bind to different therapeutic agents. Also, the antibody-polymer-drug conjugates described herein can comprise two or more polymers that are the same but can be bound to different therapeutic agents. In some aspects, the antibody-polymer-drug conjugates described herein can comprise two or more polymers that are different but can be bound to the same or different therapeutic agents. Regardless of the polymer selected, each of the polymers of a single antibody-polymer-drug conjugate can have the same or different therapeutic agent linking groups that can be used to bind to the same or different therapeutic agents.

Therapeutic Agents.

A wide variety of therapeutic agents or cytotoxic agents can be incorporated into the antibody-polymer-drug conjugate. Typically any bioactive agent that can be covalently bound to water-soluble polymeric carrier can be used. The therapeutic agents or cytotoxic agents can be a chemical compound (e.g., peptide) or a protein. In some aspects, one or more of the therapeutic agents can be an anti-cancer agent. The anti-cancer agent can be an agent or drug that has anti-cancer properties. In some embodiments, the anti-cancer agent can be a taxane, a chemotherapeutic agent, a tubulin polymerization inhibitor, topoisomerase inhibitor analogs thereof or a combination thereof. In some aspects, each occurrence of the one or more therapeutic agents independently can be an anti-cancer agent one or more of taxanes, anthracyclines, chemotherapeutic agents, tubulin polymerization inhibitors, topoisomerase inhibitors, analogs thereof or combinations thereof.

Examples of a taxane include but are not limited to paclitaxel and docetaxel, any analogues thereof and any combinations thereof. Examples of anthracyclines include but are not limited to daunorubicin, doxorubicin, epirubicin, idarubicin, mitoxantrone, and valrubicin, any analogues thereof, and any combinations thereof. Examples of chemotherapeutic agents include but are not limited to methotrexate, doxorubicin, epirubicin, prednisolone, vincristine, procarbazine, bleomycin, vinblastine, etoposide, capecitabine, folinic acid, paclitaxel, gemcitabine, melphalan, cytarabine, cyclocytidine, actinomycin daunorubicin, harringtonine, corticosteroids, any analogous thereof, or any combinations thereof. Additional therapeutic agents can also include tubulin polymerization inhibitors, topoisomerase inhibitors, any analogous thereof or any combinations thereof. Various other therapeutic agents, as will be recognized by one skilled in the art, can also be employed in the present APDCs.

In an aspect, the therapeutic agent can be epirubicin. In an aspect, the therapeutic agent can be paclitaxel.

Methods of Making Antibody-Polymer-Drug Conjugates

In certain aspects, the disclosed antibody-polymer-drug conjugates can be provided by a method comprising the step of reacting a free thiol of the antibody with an electrophilic group on a polymer-drug conjugate, thereby forming the antibody-polymer-drug conjugate. Such a free thiol can, for example, be provided by treatment of the antibody with a reducing agent prior to the reacting step. Reduction of disulfide linkages in the antibody provides free thiols that can act as nucleophiles in subsequent reaction with electrophilic functionalities (e.g., a maleimide functionality) in the disclosed polymer-drug conjugates. Such polymer-drug conjugates can comprise a therapeutic agent connected to a semitelechelic polymer via a therapeutic agent linking group.

In some aspects, the semitelechelic polymer is a copolymer of N-(2-hydroxypropyl)methacrylamide, 2-hydroxyethyl methacrylate, diethylene glycol monomethacrylate, triethylene glycol monomethacrylate, acrylonitrile, methacrylonitrile, acrylamide, methacrylamide, N-alkylmethacrylamide, N-alkylacrylamide, N,N-dialkylacrylamide, methacrylic acid, acrylic acid, esters of acrylic acid, esters of methacrylic acid, N,N-diethylaminoethyl methacrylate, N-vinylpyrrolidone, or norbornene, or combinations thereof. In further aspects, the semitelechelic polymer comprises residues of monomers of an acrylamide connected to a therapeutic agent via a therapeutic agent linking group.

In some aspects, the therapeutic agent linking group is an oligopeptide, for example, lycylphenylalanylleucylglycine. In certain aspects, the therapeutic agent linking group is stable under physiologic conditions and cleaved in lysosomal compartment.

In one aspect, the acrylamide connected to a therapeutic agent via a therapeutic agent linking group is MA-GFLG-EPI and has the structure:

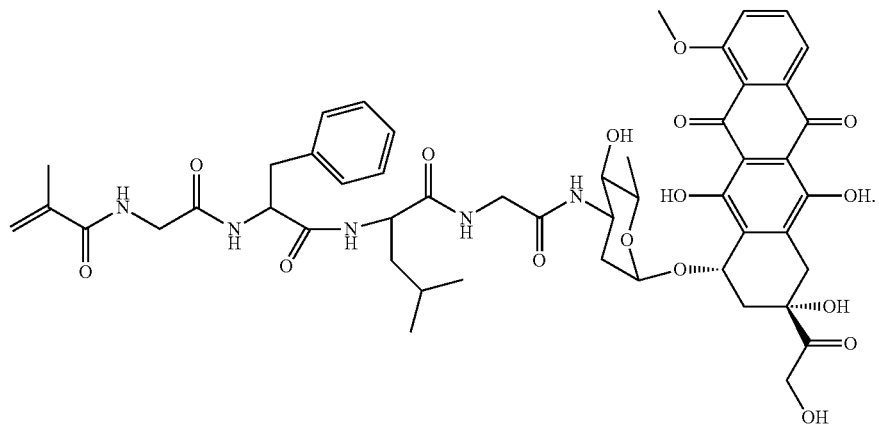

MA-GFLG-EPI

In certain aspects, the semitelechelic polymer is produced by Reversible addition-fragmentation chain transfer polymerization (RAFT) or Atom transfer radical polymerization (ATRP). In an aspect, the semitelechelic polymer has the structure:

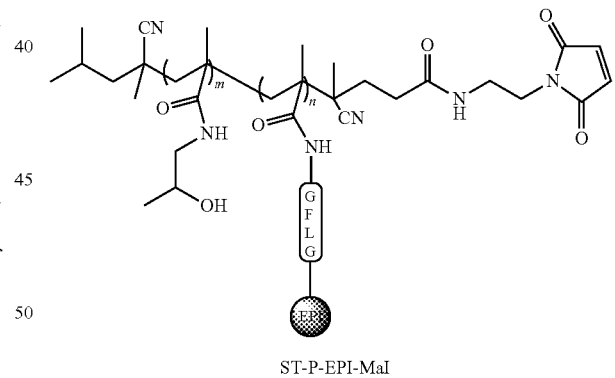

ST-P-EPI-MaI

In one aspect, the therapeutic agent is a residue of an amine-bearing drug. In a further aspect, the therapeutic agent is a residue of a hydroxy-bearing drug.

In certain aspects, the disclosed semitelechelic polymers can be provided by a method comprising the step of functionalizing a polymer-drug conjugate with an electrophilic group, for example, a Michael acceptor such as a maleimide. The semitelechelic polymer can be provided by functionalizing a polymer with a N-(aminoalkyl)maleimide.

In certain aspects, the polymer-drug conjugate is a copolymer of N-(2-hydroxypropyl)methacrylamide (HPMA) monomers and monomers of an acrylamide connected to a therapeutic agent via a therapeutic agent linking group, for example, an oligopeptide (e.g., glycylphenylalanyl-leucylglycine), which is stable under physiologic conditions and cleaved in lysosomal compartment Antibodies.

As noted above, the antibody-polymer-drug molecules as disclosed herein can include an antibody or a biologically active variant thereof. As is well known in the art, monoclonal antibodies can be made by recombinant DNA. DNA encoding monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody.

Methods for humanizing non-human antibodies are well known in the art. For example, humanized antibodies can be generated by substituting rodent CDRs or CDR sequences for the corresponding sequences of a human antibody. Methods that can be used to produce humanized antibodies are also well known in the art.

Labels.

The compositions as described herein can also include a detectable label. For example, disclosed herein are molecular probes, comprising an antibody-polymer-conjugate or an antibody-polymer-drug conjugate. The phrase "detection label" as used herein refers to any molecule that can be associated with the compositions described herein, directly or indirectly, and which results in a measurable, detectable signal, either directly or indirectly. For instance, the label can be attached to one or more of the therapeutic agents. In an aspect, the label can be attached to the targeting antibody. In an aspect, a molecular probe comprising a composition described herein, further comprises a detectable label.

Examples of detectable labels include fluorescent, radioactive isotopes, fluorescent molecules, phosphorescent molecules, enzymes, antibodies, and ligands. Examples of fluorescent labels include, but are not limited to SYBR Green I (Invitrogen), fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenoboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC. Fluorescent labels can be obtained from a variety of commercial sources, including Invitrogen, Carlsbad, Calif.; Amersham Pharmacia Biotech, Piscataway, N.J.; Molecular Probes, Eugene, Oreg.; and Research Organics, Cleveland, Ohio.

Assessment.

The antibody-polymer-drug conjugates themselves or parts of the antibody-polymer-drug conjugates can be assessed in any number of ways. For example, the binding of the therapeutic agent with the polymer can be confirmed (by using a magnetic bead-based pull down assay); cellular or kinetic uptake of the therapeutic agent can be evaluated (using fluorescence techniques); levels of the unbound antibody and low levels of free drug can be confirmed (by gel separation and Western blotting), function of the therapeutic agent as an inducer of apoptosis (by performing live/dead assay using FACS); and for stability and tissue distribution in vivo (e.g., by measuring plasma levels over time and tissue distribution by imaging assays).

Configurations.

Each part of a given antibody-polymer-drug conjugate, including the targeting antibody, one or more polymers and one or more therapeutic agents, can be selected independently. One of ordinary skill in the art would understand that the component parts need to be associated in a compatible manner. The antibody-polymer-drug conjugate can be used to deliver antibody moieties and therapeutic agents to a patient for the treatment of cancer. The targeting antibody can be referred to as a "first agent," the one or more polymers called the "second agent" and the one or more therapeutic agents, referred to as a "third agent." And, thus, the antibody-polymer-drug conjugate can be a combination therapy for a disease (e.g., a cancer). Different polymers and/or different therapeutic agent linking groups can carry different therapeutic agents. Thus, an antibody-polymer-drug conjugate can deliver two or more different therapeutic agents. With the inclusion of a detectable marker, the antibody-polymer-drug conjugate or antibody-polymer conjugate as described herein can also be used to map the distribution of targets to which the targeting antibodies bind. The number of therapeutic agents per antibody-polymer-drug conjugate can be controlled by adding, for example, more polymers, and/or more therapeutic agent linking groups.

Accordingly, in some aspects, the therapeutic agent(s) to targeting antibody can be present in a ratio of, for example, 5 to 1. The therapeutic agent(s) to targeting antibody can also be 1:1, 2:1, 3:1, 4:1, 5:1, 10:1, 15:1, 20:1, 30:1, 40:1, 50:1, 100:1 or any number in between. The therapeutic agent to polymer ratio can be present in a ratio of, for example, 8 to 1. The therapeutic agent to polymer ratio can also be 2:1, 3:1, 4:1, 5:1, 6:1, 7:1, 8:1, 9:1, 10:1, 11:1, 12:1, 13:1, 14:1, 15:1 or any number in between. In some aspects, the antibody-polymer-drug conjugates described herein can comprise about from 1 to 8 polymers. In some aspects, the antibody-drug conjugates described herein can comprise about from 1-10 therapeutic agents per polymer.

In certain aspects, this ratio is the same as the average number of therapeutic agents conjugated to the antibody, which can be equal to the product of the average number of MA-GFLG-EPI residues in the polymer ("n") and the average number of polymers conjugated to the antibody ("p").

In some aspects, m can be from about 0 to about 100. It is appreciated that m is an interger with respect to a specific polymer, but can be expressed as a non-interger for the average over a collection of polymers (e.g., all of the polymers attached to a specific antibody or within a composition comprising the described conjugates). For example, m can be from about 0 to about 5, from about 0 to about 10, from about 0 to about 20, from about 0 to about 50, from about 1 to about 5, from about 1 to about 10, from about 1 to about 20, or from about 1 to about 50.

In some aspects, n can be from about 1 to about 10. It is appreciated that n is an interger with respect to a specific polymer, but can be expressed as a non-interger for the average over a collection of polymers (e.g., all of the polymers attached to a specific antibody or within a composition comprising the described conjugates). For example, n can be from about 1 to about 10, from about 1 to about 8, from about 1 to about 6, from about 1 to about 4, from about 1 to about 3, from about 1 to about 2, from about 2 to about 5, or from about 2 to about 8.

In some aspects, p can be from about 1 to about 8. It is appreciated that p is an interger with respect to a specific antibody, but can be expressed as a non-interger for the average over a collection of antibodies (e.g., within a composition comprising the described conjugates). For example, p can be from about 1 to about 8, from about 1 to about 6, from about 1 to about 4, from about 1 to about 3, from about 1 to about 2, from about 2 to about 5, or from about 2 to about 8.

Thus, in certain aspects, the antibody-drug conjugates described herein can comprise about from about 1 to about 80 therapeutic agents per targeting antibody.

The methods disclosed herein related to the process of producing the antibody-polymer-drug conjugates as disclosed can be readily modified to produce a pharmaceutically acceptable salt of the antibody-polymer-drug conjugates. Pharmaceutical compositions including such salts and methods of administering them are accordingly within the scope of the present disclosure.

Pharmaceutical Compositions

As disclosed herein, are pharmaceutical compositions, comprising the antibody-polymer-drug conjugate and a pharmaceutical acceptable carrier described above. In some aspects, the therapeutic agent can be an anti-cancer agent and the pharmaceutical composition can be formulated for intravenous administration. In some aspects, the pharmaceutical composition can be formulated for intravenous administration or intratumor injection. The compositions of the present disclosure also contain a therapeutically effective amount of an antibody-polymer-drug conjugate as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the antibody-polymer-drug conjugates. Thus, compositions can be prepared for parenteral administration that includes antibody-polymer-drug conjugates dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein, are methods of treating a subject with cancer, the method comprising: (a) identifying a patient in need of treatment; and (b) administering to the subject a therapeutically effective amount of the pharmaceutical composition comprising antibody-polymer-drug conjugates comprising a targeting antibody, one or more polymers (e.g., semitelechelic), and one or more therapeutic agents, and a pharmaceutically acceptable carrier. In some aspects, there can be two or more, three or more or four or more polymers (e.g., semitelechelic). In some aspects there can be two or more, three or more or four or more therapeutic agents.

In some aspects, the one or more therapeutic agents can be locally delivered to a target cell to which the targeting antibody can bind or is capable of binding. In some aspects, the one or more therapeutic agents can be released in a lysosome of a target cell.

The pharmaceutical compositions described above can be formulated to include a therapeutically effective amount of an antibody-polymer-drug conjugate. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of cancer.

The pharmaceutical compositions described herein can be administered to the subject (e.g., a human patient) in an amount sufficient to delay, reduce, or preferably prevent the onset of clinical disease. Accordingly, in some aspects, the subject can be a human subject. In therapeutic applications, compositions can be administered to a subject (e.g., a human patient) already with or diagnosed with cancer in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cancer is delayed, hindered, or prevented, or the cancer or a symptom of the cancer is ameliorated. One or more of the symptoms can be less severe. Recovery can be accelerated in an individual who has been treated.

In some aspects, the cancer can be a primary or secondary tumor, refractory or relapsing tumor. In other aspects, the primary or secondary tumor or refractory or relapsing tumor can be within the patient's breast, lymphatic system, bladder, stomach, lung(s), uterus, gall bladder or one or more ovaries. In some aspects, the primary or secondary tumor or refractory or relapsing tumor can be a blood cell tumor. In an aspect, the blood cell tumor can be lymphoma. In an aspect, the lymphoma can be non-Hodgkin's lymphoma. In some aspects, the non-Hodgkin's lymphoma can be follicular lymphoma, mantle cell lymphoma, marginal zone cell lymphoma, diffuse large-B-cell lymphoma or Burkitt lymphoma. In yet other aspects, the cancer can be associated with the expression of HER2, CD20 or OA-3. In some aspects, the cancer can be associated with the expression of an epidermal growth factor receptor (e.g., HER2). In some aspects, the cancer can be associated with the expression of a B lymphocyte associated antigen (e.g., CD20). In some aspects, the cancer can be associated with the expression of an ovarian cancer antigen (e.g., OA-3). In an aspect, the cancer can be associated with the expression (or overexpression) of HER2. In an aspect, the cancer can be associated with the expression (or overexpression) of CD20. In an aspect, the cancer can be associated with the expression (or overexpression) of OA-3.

Disclosed herein, are methods of treating a subject or patient with cancer. The cancer can be any cancer. In some aspects, the cancer can be breast cancer, bladder cancer, gastric cancer, stomach cancer, lung cancer, non-small cell lung cancer, uterine cancer, endometrial cancer, gall bladder, ovarian cancer, or lymphoma. In some aspects, the cancer affects the blood, bone marrow, lymph or lymphatic system. Tumors of the blood can also affect the circulatory system and/or the immune system. Blood cancers can also be referred to as liquid cancers and can affect red blood cells, white blood cells or a combination of both. Cancers of the blood can also be called hematological malignancies and can be further classified as leukemias, lymphomas and myelomas. Examples of lymphomas include Hodgkin's lymphoma and non-Hodgkin's lymphomas. Classical Hodgkin lymphoma can be further classified into the following subtypes: nodular sclerosing Hodgkin lymphoma, mixed-cellularity, lymphocyte-rich or lymphocytic predominance and lymphocyte depleted. Nodular lymphocyte predominant Hodgkin's lymphoma may express CD20. Non-Hodgkin lymphomas include all subtypes of lymphoma except Hodgkin's lymphoma. Hodgkin lymphoma cells express CD30. B cell non-Hodgkin lymphomas express CD20. Examples of B cell non-Hodgkin lymphomas include B-cell chronic lymphocytic leukemia/small lymphocytic lymphoma, B-cell prolymphocytic leukemia, lymphoplasmacytic lymphoma, splenic marginal zone B-cell lymphoma (±villous lymphocytes), hairy cell leukemia, plasma cell myeloma/plasmacytoma, extranodal marginal zone B-cell lymphoma of the MALT type, nodal marginal zone B-cell lymphoma (±monocytoid B cells), follicular lymphoma, mantle cell lymphoma, marginal zone cell lymphoma, diffuse large B-cell lymphomas (including mediastinal large B-cell lymphoma and primary effusion lymphoma) and Burkitt lymphoma. In an aspect, the blood cell tumor can be lymphoma. In an aspect, the lymphoma can be a non-Hodgkin's lymphoma.

The methods of treatment disclosed herein can also include a step of killing a specific cell type (e.g., a B cell expressing CD20, a cell expressing HER2, or a cell expressing OA-3). The methods of treatment can further include a step of contacting a cell with the compositions and/or APDCs described herein.

In an aspect, the methods disclosed herein can include selecting herceptin as the targeting antibody to treat a subject having, predisposed to having, or suspected of having breast, bladder, gall bladder and/or ovarian cancer. In an aspect, the methods disclosed herein can include selecting OV-TL16 as the targeting antibody to treat a subject having, predisposed to having, or suspected of having ovarian cancer.

In an aspect, the methods of treatment disclosed herein can also include the administration of a therapeutically effective amount of radiation therapy, immunotherapy, chemotherapy, stem cell transplantation or a combination thereof.

Amounts effective for this use can depend on the severity of the cancer and the weight and general state and health of the subject. Suitable regimes for initial administration and booster administrations are typified by an initial administration followed by repeated doses at one or more hourly, daily, weekly, or monthly intervals by a subsequent administration. For example, a subject can receive one or more dose of an antibody-polymer-drug conjugate one or more times per week (e.g., 2, 3, 4, 5, 6, or 7 or more times per week).

The total effective amount of an antibody-polymer-drug conjugate in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of the one or more of the therapeutic agents present within the compositions described herein and used in the methods as disclosed herein applied to mammals (e.g., humans) can be determined by one of ordinary skill in the art with consideration of individual differences in age, weight, and other general conditions (as mentioned above). Because the antibody-polymer-drug conjugates of the present disclosure can be stable in serum and the bloodstream and in some cases more specific, the dosage of the an antibody-polymer-drug conjugates including any individual component can be lower (or higher) than an effective dose of any of the individual components when unbound. Accordingly, in some aspects, the anticancer agent administered has increased efficacy or reduced side effects when administered as part of an antibody-polymer-drug conjugate as compared to when the anticancer agent is administered alone or not as part of an antibody-polymer-drug conjugate.

Kits

The kits can include a composition comprising a targeting antibody, one or more polymers (e.g., semitelechelic) and one or more therapeutic agents; and suitable instructions (e.g., written and/or audio-, visual-, or audiovisual material). In an aspect, kit can further include one or more linking groups disclosed herein. The composition can further comprise a pharmaceutically acceptable carrier. In an aspect, the kit includes a pharmaceutical composition as described herein that is packaged together with instructions for use. The kits can also include one or more of the following: diluents, sterile fluid, syringes, a sterile container, gloves, vials or other containers, pipettes, needles and the like.

EXAMPLES

The binding affinity of RTX to Ramos cells before and after conjugation was analyzed using flow cytometry. The antitumor efficacy of the new ADC-RTX-P-EPI was evaluated on male NOD SCID mice bearing subcutaneous Ramos B-cell lymphoma tumors.

Materials and Methods

Chemicals.

All solvents were purchased with the highest grade from Fisher Scientific (Pittsburgh, Pa.) and used as received. Dicyclohexylcarbodiimide (DCC), 4-(dimethylamino)pyridine (DMAP), and HATU (1-[bis(dimethylamino)methylene]-1H-1,2,3-triazolo[4,5-b]pyridinium 3-oxid hexafluorophosphate) were purchased from AAPPTEC (Louisville, Ky.). Iodine-125 [$^{125}$I] was from Perkin-Elmer. Bicinchoninic acid (BCA) protein assay kit and tris(2-carboxyethyl)phosphine (TCEP) were from Thermo Scientific Pierce (Rockford, Ill.). Thiazolidine-2-thione (TT), N-2-aminoethylmaleimide trifluoroacetate and diisopropylethylamine (DIPEA) were purchased from Sigma-Aldrich (St. Louis, Mo.). Cy5-NHS ester was from Lumiprobe (Hallandale Beach, Fla.). 2,2'-Azobis(2,4-dimethylvaleronitrile) (V65), 2,2'-azobis(4-methoxy-2,4-dimethylvaleronitrile) (V70) were from Wako USA (Richmond, Va.). Epirubicin hydrochloride was purchased from DKY Technology (Wuhan, China). N-(2-Hydroxypropyl)methacrylamide (HPMA) (Kopeček and Bažová, 1973), N-methacryloylglycylphenylalanylleucylglycine (MA-GFLG-OH) (Ulbrich, et al., 2000), N-methacryloylglycylphenylalanylleucylglycine-epirubicin (MA-GFLG-EPI) (Yang, et al., 2015), and 4-cyanopentanoic acid dithiobenzoate (CPDB) (Mitsukami et al., 2001) were synthesized according to literatures.

Cells and Reagents.

Ramos and Raji Burkitt's lymphoma cell lines were from American Type Culture Collection (ATCC) (Manassas, Va.) and maintained at 37° C. in a humidified atmosphere containing 5% $CO_2$ in RPMI-1640 medium (Gibco) supplemented with 10% FBS and a mixture of antibiotics (100 units/ml penicillin, 0.1 mg/ml streptomycin). Rituximab (Genentech) was obtained from Hunstman Cancer Hospital, University of Utah at a stock concentration of 10 mg/ml. Human IgG was from Sigma (St. Louis, Mo.). Alexa Fluor® 488 Goat anti-Human IgG (H+L) was from Thermo Fisher Scientific (Waltham, Mass.). Cell Counting Kit-8 (CCK-8) was from Dojindo (Rockville, Md.). Annexin V-FITC Apoptosis Kit was purchased from Clontech (Mountain View, Calif.).

Animals.

About 7-9 week-old male NODSCID mice (25-30 g) were bred in-house (originally purchased from Jackson Laboratories (Bar Harbor, Me.)). Animals were housed in the Animal Facility of the Comparative Medicine Center at the University of Utah under standard conditions. Procedures involving animals and their care were conducted following approved Institutional Animal Care and Use Committee (IACUC) protocols.

Statistics.

All experiments in this study were at least triplicated. Quantified analyses were presented as mean±standard deviation (SD). One-way analysis of variance (ANOVA)

coupled with Tukey's post hoc analysis was used to compare three or more groups (with p value <0.05 indicating statistically significant difference).

Example 1: Synthesis of Antibody-Drug Conjugates

Synthesis of 2-cyano-5-oxo-5-(2-thioxothiazolidin-3-yl)pental-2-yl benzodithioate (CTA-TT)

CTA-TT was synthesized as previously described (Tao et al., 2009). In brief, 0.84 g CPDB, 0.36 g TT and 0.025 g DMAP were dissolved in 10 ml dichloromethane (DCM) and precooled with ice bath. DCC in 10 ml DCM was added dropwise to the flask within 30 min, then stirring continued for 6 h in dark at room temperature (r.t.). After working up, filtration (to remove precipitated salts) gave rise to a red filtrate. The solution was concentrated by rotary-evaporator. CTA-TT is purified via silica gel column chromatography (70-230 mesh, 60 Å) using gradient ethylacetate/hexane (step gradient 1:3 to 1:1, v/v) as eluent. The fraction was evaporated under reduced pressure. The CTA-TT agent was obtained as red oil. $^1$H NMR CDCl$_3$ (ppm): 7.60-7.30 (benzene), 4.60-4.50 (NCH$_2$CH$_2$), 3.40-3.20 (SCH$_2$CH$_2$), 2.70-2.60 (CCH$_2$CH$_2$), 2.60-2.50 (CCH$_2$CH$_2$), 2.20-2.10 (CCH$_2$CH$_2$), 2.00-1.90 (CH$_3$).

Synthesis of Semitelechelic Maleimide Functionalized HPMA Copolymer-Epirubicin Conjugate (ST-P-EPI-Mal)

Semitelechelic (ST) HPMA copolymers terminated with maleimide group were prepared by RAFT copolymerization followed by two-step end modification. A typical polymerization process is briefly summarized as follows: An ampoule containing HPMA (139 mg, 0.97 mmol) and MA-GFLG-EPI (30 mg, 0.03 mmol) were attached to the Schlenk-line. After three vacuum-nitrogen cycles to remove oxygen, CTA-TT (4 mg/ml×170 in degassed MeOH/H$^+$ 0.3% acetic acid) and V70 (1 mg/ml×184 in degassed MeOH/H$^+$0.3% acetic acid) were added via syringe under magnetic stirring and bubbled with N$_2$ for 10 min in ice bath. The ampoule was sealed, and polymerization was performed at 30° C. for 22 h. The copolymer was obtained by precipitation into acetone/ethyl ether and purified by redissolving in methanol and precipitation in acetone/ethyl ether two more times. The copolymer was isolated as red powder and dried under vacuum. The average molecular weight (Mw) and the polydispersity (PDI) of the conjugates were determined using size-exclusion chromatography (SEC) on an ÄKTA FPLC system equipped with a UV detector (GE Healthcare), mini DAWN TREOS, and OptilabrEX (refractive index) detector (Wyatt Technology) using a Superose 6 HR10/30 column with sodium acetate buffer containing 30% acetonitrile (pH 6.5) as mobile phase. The dithiobenzoate group was removed by further reaction with 40-times excess V-65 in 0.3 ml MeOH/H$^+$ at 55° C. for 2 h, and precipitation into acetone/ethyl ether twice, resulting in ST-P-EPI-TT (70 mg, 41%). The content of EPI in copolymer was determined spectrophotometrically ($\lambda_{max}$=495 nm) by dissolving ST-P-EPI-TT in methanol (~2 mg/10 ml) and calculated according to EPI standard curve in methanol.

The end-chain reactive maleimide (mal) group was incorporated by the reaction of TT group with N-(2-aminoethyl) maleimide. For example, 18 mg ST-P-EPI-TT was dissolved in 500 µl DMSO, then the solution was added into 0.1 ml DMSO containing 10 µl DIPEA and 5 mg N-(2-aminoethyl) maleimide trifluoroacetate. After stirring at room temperature for 24 h, the polymer was isolated by precipitation in acetone/ether three times to yield 16.5 mg ST-P-EPI-mal. The presence of maleimide group was confirmed by modified Ellman assay.

Synthesis of Antibody-Polymer-EPI Conjugates

Thirteen mg Rituximab was buffer changed with Tris-HCl buffer (20 mM, 5 mM EDTA, pH 7.4) to final volume 2.5 ml and mixed with TCEP (100 mM×300 µl, 80 times excess in Tris-HCl buffer, pH 7.4). After incubation at 37° C. for 3 h, the excess TCEP was removed by ultrafiltration (EMD Millipore Amicon™, MWCO 30,000) four times with Tris buffer to yield RTX-SH. ST-P-EPI-Mal (16.5 mg, in 400 µl Tris.HCl buffer) was added into RTX-SH solution, and incubated at 37° C. for 6 h. After working up, the conjugate was purified using SEC on ÄKTA FPLC system (GE Healthcare, Piscataway, N.J.) equipped with Sephacryl S-100 HR16/60 column eluted with PBS (pH 7.2) to remove free, unconjugated ST-P-EPI.

Following the same procedure, non-specific IgG-P-EPI was prepared. The protein concentration (RTX or IgG) in final solution was determined with BCA protein assay, whereas the polymer content was evaluated using UV-Vis spectroscopy based on EPI content. Consequently, the substitution degree (P-EPI/mAb) and drug-to-antibody ratio (DAR) were calculated.

Synthesis of RTX-EPI Conjugate

To synthesize maleimide modified epirubicin, 6-(2,5-dioxo-2,5-dihydro-1H-pyrrol-1-yl)hexanoic acid (12 mg, 0.06 mmol) was dissolved in 200 µl DMF, HATU (0.05 mmol) and DIPEA (20 µl) was added and stirred at room temperature for 30 min. The mixture was transferred into EPI (27 mg, 0.05 mmol) solution with 15 µl DIPEA in 100 µl DMF. The reaction mixture was stirred at room temperature overnight to yield EPI-mal. The product was purified by HPLC (Agilent ZORBAX, 5 µm, 300SB-C18 column 9.4× 250 mm, using flow rate 2.5 ml/min and gradient elution from 2% to 90% of buffer B within 30 min. Buffer A: DI H$_2$O, Buffer B: acetonitrile). The structure and purity of the product were confirmed by MALDI-TOF-MS and HPLC analysis. MS (MALDI-TOF) m/z: 759.21 [M+Na]+, 775.18 [M+K]+.

RTX-SH was prepared as described above. EPI-mal (10 mM×35 µl in DMSO) was added into RTX-SH solution, and incubated at room temperature for 2 h and purified by ultrafiltration (30,000 Da cut-off) four times with PBS. The molar ratio of EPI/RTX was calculated by UV-vis absorbance as 3.1.

RTX Labeled with Cy5.

Rituximab (10 mg/ml×300 µl) in PBS was buffer changed with added PBS buffer (pH 8.0) three times. Cy5-NHS (5 mg/ml×8 µl, in DMSO, RTX: Cy5=1:3) was added and incubated at room temperature for 2 h to yield RTX-Cy5. The free Cy5-NHS was removed by PD-10 column and ultrafiltration (30,000 Da cut-off) three times. The RTX concentration in the final RTX-Cy5 solution was determined by BCA assay, and the Cy5 content was determined by UV-visible spectroscopy (molar extinction coefficient: 125,000 M$^{-1}$ cm$^{-1}$ at 645 nm in PBS). The ratio of Cy5/RTX was 0.8.

Sodium Dodecyl Sulfate Polyacrylamide Gel Electrophoresis (SDS-PAGE).

Samples were prepared in SDS-PAGE loading buffer. The samples were loaded onto (6-10%) acrylamide gel run at 110

V and 30 mA for 1.5 h in 1×running buffer (25 mM Tris-HCl, 250 mM glycine, and 0.1% SDS) on a Bio-Rad Mini-PROTEAN gel apparatus.

Design, Preparation and Characterization of Antibody-Drug Conjugate RTX-P-EPI.

Conjugation of drugs to an antibody usually takes place at a solvent accessible lysine or cysteine. A human IgG comprises about 100 lysine residues. About half of them, located at both heavy chains and light chains, are accessible and could be modified, resulting in a heterogeneous mixture of conjugates with DAR being 0 to 8. This implicates that a wide range of in vivo pharmacokinetic properties will be generated with this unspecific approach. Cysteine conjugation occurs after reduction of four interchain disulfide bonds that yields ≤8 of exposed sulfhydryl groups. Consequently, the resulting ADCs have a lower degree of heterogeneity. Therefore, conjugation via cysteine residue was selected, and the designed synthetic approach is depicted in FIG. 1: Maleimide-modified semitelechelic HPMA copolymer-epirubicin conjugate was first prepared, then attached to RTX via thioether bonds as a result of thiol-ene reaction.

The copolymer precursor was prepared by RAFT copolymerization of HPMA with MA-GFLG-EPI. The use of chain transfer agent CTA-TT enables preparation of copolymers with a reactive TT group at one chain (macromolecule) end. To ensure the polymer carrier eventual elimination, the average molecular weight of a polymer precursor was controlled to be below the renal threshold (<~50 kDa). ST-P-EPI-TT contained 0.89 end TT groups at the end of polymer (determined by UV spectrophotometry using molar extinction coefficient of monomer 10 800 L·mol$^{-1}$ cm$^{-1}$ in MeOH at 305 nm, UV spectrophotometry of EPI at 305 nm as base line). ST-P-EPI-mal contained 0.86 maleimide groups per polymer, which was determined by modified Ellman's assay (Gergel and Cederbaum, 1996). EPI precursors were synthesized following the same procedure. Their characterization is summarized in Table 1.

TABLE 1

Characterization of ST-P-EPI.

| Polymer precursor | Mn (kDa) | Mw/Mn | EPI wt % | EPI/polymer chain |
|---|---|---|---|---|
| ST-P-EPI-1 | 37.9 | 1.17 | 9.4 | 6.6 |
| ST-P-EPI-2 | 32.9 | 1.11 | 8.0 | 4.7 |

Figure 12:
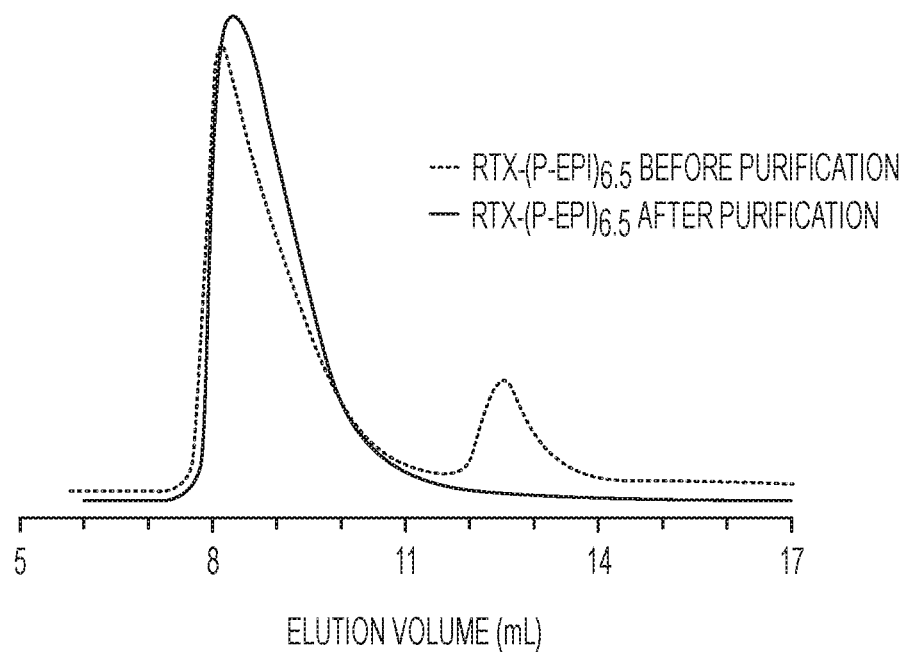
FIG. 12 shows the fast protein liquid chromatography (FPLC) analysis of RTX-(P-EPI)$_{6.5}$ before and after purification.

To attach the active copolymer precursors to RTX, RTX was treated with TCEP in Tris.HCl buffer (pH 7.4). Under such mild condition, the solvent-accessible four inter-chain disulfide bonds were reduced into thiol groups (RTX-SH). Ellman assay (Gergel and Cederbaum, 1996) showed that the thiol/mAb ratio of RTX-SH was 7.9. SEC analysis showed the same elution volume with RTX, which is coincident with a previous report (Zhang et al., 2015) and indicated the same molecular weight with RTX. RTX-SH was reacted with excess of ST-P-EPI in Tris-HCl buffer. SEC analysis showed that after attachment, the peak corresponding to RTX completely disappeared, accompanied by a new peak corresponding to the conjugate RTX-P-EPI (FIG. 12). The SEC profiles of pure RTX-P-EPI, RTX and polymer precursor ST-P-EPI are shown in FIG. 3A.

As control (for biological evaluation), non-specific human IgG-P-EPI and a conjugate RTX-EPI, in which EPI was directly attached to RTX were also prepared (FIG. 2).

Sodium dodecyl sulfate polyacrylamide gel electrophoresis (SDS-PAGE) analysis further confirmed the successful synthesis of RTX-P-EPI: non-denatured product (FIG. 3B Lane 5) validated the disappearance of the free antibody band, accompanied by the emergence of smears with higher apparent molecular weights corresponding to the conjugate RTX-P-EPI.

To elucidate the relationship between substitution degree of ST-P-EPI and retained RTX binding ability, four RTX-P-EPI conjugates with various DARs were prepared by changing the feed ratio of [ST-P-EPI-mal]/[RTX-SH] and reaction time. Their characterization is summarized in Table 2.

TABLE 2

Characterization of RTX-(P-EPI)x and control conjugates.

| No. | Conjugate | Polymer-precursor | P/Ab ratio | EPI/antibody (DAR) |
|---|---|---|---|---|
| 1 | RTX-EPI | — | — | 3.1 |
| 2 | RTX-(P-EPI)$_{3.1}$ | ST-P-EPI-1 | 3.1 | 20.6 |
| 3 | RTX-(P-EPI)$_{4.4}$ | ST-P-EPI-2 | 4.4 | 20.7 |
| 4 | RTX-(P-EPI)$_{5.6}$ | ST-P-EPI-2 | 5.6 | 26.3 |
| 5 | RTX-(P-EPI)$_{6.5}$ | ST-P-EPI-1 | 6.5 | 42.9 |
| 6 | IgG-(P-EPI)$_{3.6}$ | ST-P-EPI-2 | 3.6 | 16.9 |

Figure 4:
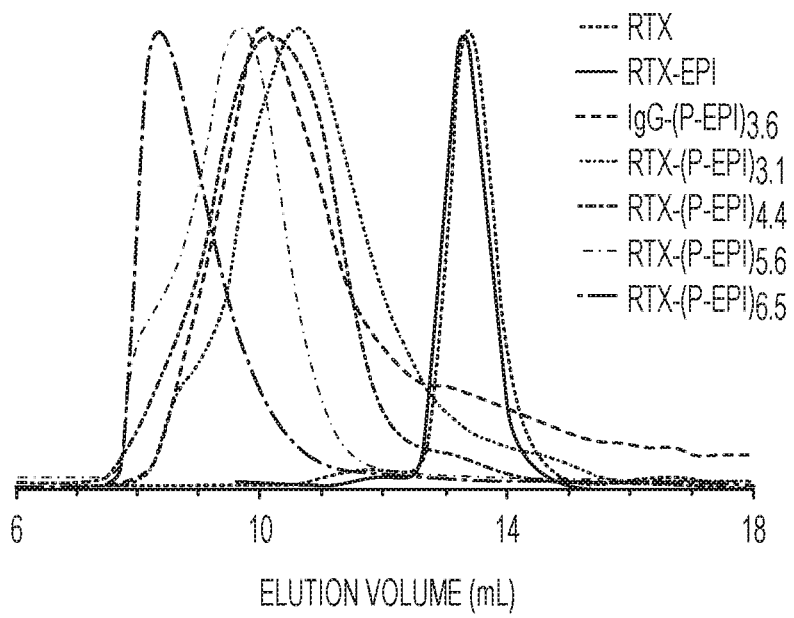
FIG. 4 shows the SEC analysis of antibody-drug conjugates with different substitutions.

Unlike classic ADCs in which higher payload causes association and impairs solubility, in the system described herein, even when the DAR reaches over 40 (No. 5 RTX-(P-EPI)$_{6.5}$), the conjugate was still water-soluble, and there was no aggregation detectable (FIG. 4).

Example 2: Binding Affinity Evaluation

To evaluate cell binding of antibody and antibody-polymer-drug conjugate, Ramos cell line with high CD20 expression was selected as target. Cells (2×10$^5$ in 400 µl medium) were centrifuged by 2000 RPM for 5 min, the supernatant was removed and the final volume was about 50 µl. Conjugates with increasing concentration (0.04, 0.2 or 1 µg in 20 µl PBS) were added. IgG-P-EPI and RTX were used for comparison. Cells were incubated at 4° C. for 20 min and washed with medium twice to remove unbound conjugates. Cells were then stained with 100 µl secondary antibody (Alexa Fluor® 488 goat-anti human IgG (H+L), 1:200 diluted) and incubated at 4° C. for another 20 min. After washing by PBS twice, labeled cells were analyzed by flow cytometry.

Binding Affinity of Various Conjugates to Ramos B-Cells.

Figure 13:
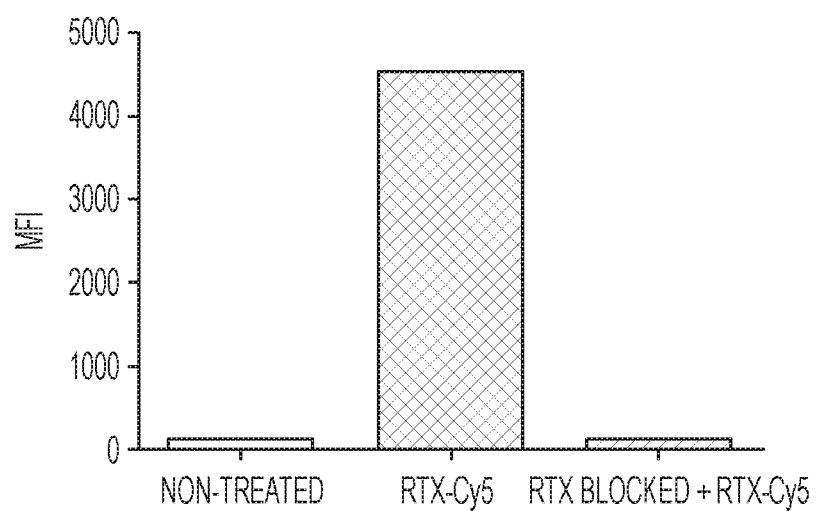
FIG. 13 shows RTX-Cy5 binding on the surface of Ramos cells. Non-treated, cells in culture medium; RTX-Cy5, Ramos cells ($2\times10^5$) were treated with 1 μg RTX-Cy5 at 4° C. for 30 min; RTX Blocked+RTX-Cy5, after pre-blocking by 10 μg RTX at 4° C. for 30 min, 1 μg RTX-Cy5 was added and incubated at 4° C. for 30 min. The cells were analyzed by flow cytometry. Data are reported as MFI, mean fluorescence intensity.

To ensure CD-20 antigen expression on the surface of the Ramos cells used, the Ramos cells were exposed to RTX labeled with Cy5 (RTX-Cy5). Flow cytometry analysis showed a high Cy5 signal of incubated Ramos cells. Nevertheless, if CD20 receptors were blocked with an oversaturation dose of RTX, there was no Cy5 signal detectable following incubation of cells with RTX-Cy5 (FIG. 13). This confirmed the expression of CD20 on the surface of the Ramos cells, and their specific binding affinity to RTX.

To evaluate the binding characteristics of antibody-drug conjugates, Ramos cells were treated with three different amounts of RTX or equivalent RTX-drug conjugates, incubated at 4° C. to block antigen modulation, and washed to remove unbound material. Goat antihuman IgG fluorescently labeled secondary antibody was used to determine mean fluorescence intensity (MFI) of each conjugate sample. Higher MFI indicates more bound conjugates. More specifically, 2×10$^5$ Ramos cells in 50 µl medium was mixed with different samples (1, 0.2 or 0.04 µg in 20 µl PBS) and incubated at 4° C. for 30 min. The mixture was washed by medium twice to remove unbound sample. 100 µl second antibody (GAH-488, 1:200 diluted) was added and incubated at 4° C. for 30 min. After washing by PBS, the cells were analyzed by flow cytometry. All data are presented as mean±SD (n=3).

Figure 5:
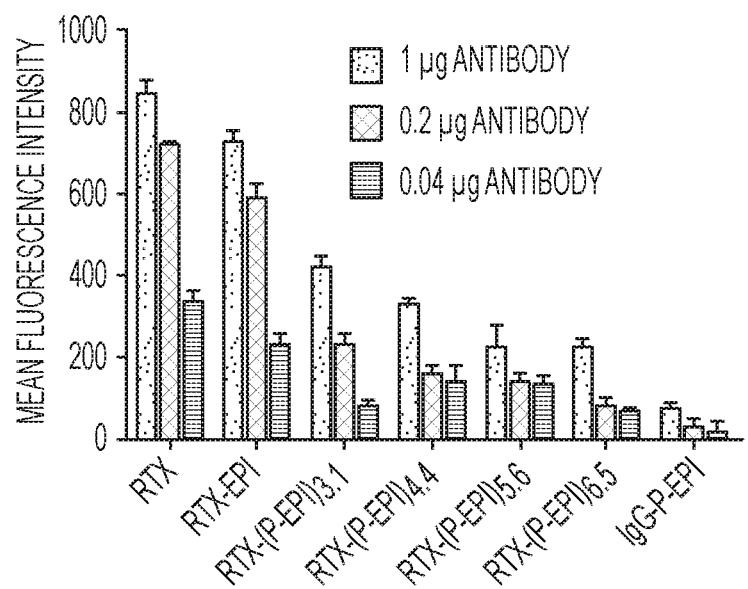
FIG. 5 shows the mean fluorescence intensity of Ramos cells following exposure to different amounts of RTX alone or antibody-drug conjugates. $2\times10^5$ Ramos cells in 50 μl medium was mixed with different samples (1, 0.2 or 0.04 μg in 20 μl PBS) and incubated at 4° C. for 30 min. The mixture was washed by medium twice to remove unbound sample. 100 μl second antibody (GAH-488, 1:200 diluted) was added and incubated at 4° C. for 30 min. After washing by PBS, the cells were analyzed by flow cytometry. All data are presented as mean±SD (n=3).

FIG. 5 shows the binding affinity was influenced by the ratio of polymer to antibody in all three concentrations used. As expected, IgG-P-EPI barely bound to Ramos cells; modification of RTX with P-EPI partially decreased the binding affinity in a 'valency' dependent manner; the higher the attachment of polymer-precursor, the higher the decrease of conjugate binding. At given concentration (1 µg Ab), when 3 polymer chains were attached at the inter chain disulfide-binding sites of RTX, the conjugate (RTX-(P-EPI)$_{3.1}$) showed over 50% binding affinity retention compared with unconjugated RTX, whereas conjugates with 4.5 and 5.6 polymer chains (RTX-(P-EPI)$_{4.5}$, RTX-(P-EPI)$_{5.6}$) showed about 40% and 30% binding affinity retention, respectively. RTX-(P-EPI)$_{6.5}$ showed similar binding affinity with RTX-(P-EPI)$_{5.6}$. Therefore, for further in vitro cytotoxicity and in vivo efficacy evaluation, the conjugate RTX-(P-EPI)$_{3.1}$ was used, and simply denoted as RTX-P-EPI.

Example 3: In Vitro Cell Growth Inhibition and Apoptosis

Cell Growth Inhibition.
The cytotoxicity of antibody and antibody-polymer-drug conjugates against Ramos cells was measured by CCK-8 assay (Dojindo). The cells were seeded in 96-well plates at the density of 10,000 cells (200 µl) per well in RMPI-1640 media containing 10% FBS. After 24 h, RTX, RTX-EPI RTX-P-EPI, mixture of RTX with P-EPI and IgG-P-EPI (0.3 mg/ml×15 µl for antibody) in medium was added and incubated at 37° C. for 48 h. The number of viable cells was estimated using CCK-8 kit according to the manufacturer's protocol. In brief, 50 µl 5× diluted CCK-8 solution was added and incubated at 37° C., 5% $CO_2$ for 4 h, the absorbance was measured using a microplate reader at 450 nm (630 nm as reference). Untreated control cells were set as 100% viable.

Apoptosis.
Annexin V-FITC and PI staining were performed following the RAPID™ protocol provided by the manufacturer. 2×10$^5$ Ramos cells were suspended in 0.4 ml fresh growth medium containing 0.2 µM (antibody) RTX, RTX-EPI, RTX-P-EPI, IgG-P-EPI or mixture of RTX and P-EPI (the concentration of P-EPI was equal to the content of RTX-P-EPI). The cell suspension was incubated for 48 h. All experiments were carried out in triplicate.

Figure 6:
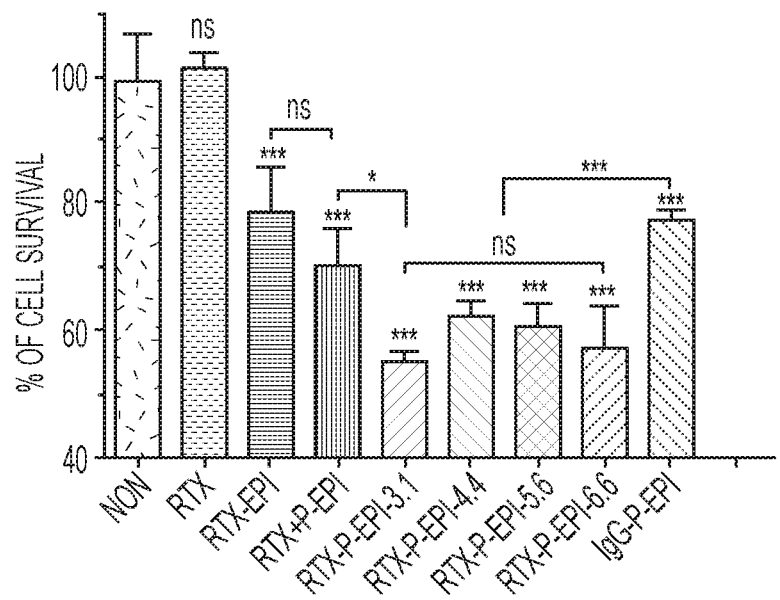
FIG. 6 shows in vitro cytotoxicity of RTX-P-EPI toward Ramos cells.

In Vitro Toxicity of Antibody-Polymer-Drug Conjugates.
The cytotoxicity of RTX-P-EPI against Ramos cells was first evaluated at the concentration of 0.15 µM (related to RTX). Unconjugated RTX, non-specific conjugate IgG-P-EPI and directly conjugated with free drug (RTX-EPI) were used as controls. The Ramos cells were incubated with the samples for 48 h and evaluated by CCK-8 assay (FIG. 6). Under the given condition, the new design conjugates RTX-(P-EPI)x (x=3.1, 4.4, 5.6, 6.5) exhibited remarkable ability to inhibit proliferation of Ramos cells (about 40% kill) regardless of the variable substitution degrees, whereas the cytotoxicity of RTX alone was nearly undetectable. Especially, the advantage of antibody-polymer-drug conjugates was demonstrated in comparison with the classic antibody-drug conjugate RTX-EPI (18% kill) and the mixture of RTX and P-EPI (the equal concentration of RTX and EPI with RTX-(P-EPI)$_{3.1}$, 30% kill). Non-specific conjugate IgG-P-EPI (22% kill) showed moderate cytotoxicity. These results implicate the potential clinical application of RTX-P-EPI, an antibody conjugated with conventional chemotherapeutics.

RTX, RTX-EPI, RTX+P-EPI and IgG-P-EPI were used as references. 10$^4$ Ramos cells were seeded in each well of 96-well plates in 200 µl RPMI-1640 media containing 10% FBS. Different samples (0.3 mg/ml×15 µl) were added and incubated at 37° C. in a humidified atmosphere of 5% $CO_2$ (v/v). After 48 h, the number of viable cells was estimated using CCK-8 kit at 450 nm (630 nm as reference). Non-treated cells were set as 100% viable. All data are presented as mean±SD (n=3). Statistical analysis was performed by one-way analysis of variance (ANOVA) to compare three or more groups (with p value <0.05 indicating statistically significant difference; *<0.05, ***<0.0001).

To further investigate the antitumor activity of the conjugate RTX-P-EPI, Ramos and Raji cells were used to detect the apoptosis level induced by the conjugate. Cells (2×10$^5$/well) were incubated at concentration of 0.2 µM RTX equivalent for 48 h (for Ramos) or 24 h (for Raji). Apoptosis induction of cells was analyzed using Annexin V/PI staining. For control samples, IgG-P-EPI had minimal cytotoxicity, while RTX-EPI or RTX+P-EPI had similar cytotoxicity as RTX alone. By contrast, RTX-P-EPI had markedly increased cytotoxicity compared with all three RTX-containing groups (FIG. 7). The superiority of RTX-P-EPI was also observed in Raji cells. When cells were treated with RTX alone, increase of antibody concentration from 0.2 µM to 2 µM did not significantly enhance the apoptosis level, suggesting that antibody binding to the cells may have reached saturation. However, when cells were first treated with a high concentration of RTX (2 µM) followed 1 h later by exposure to 0.2 µM equivalent RTX-P-EPI, the percentage of apoptotic cells almost doubled, which indicates that RTX-P-EPI could be active against RTX-pretreated cells. This raises the likelihood that this system may be efficient in the 1 h treatment of RTX-resistant disease.

Apoptosis induction in Ramos and Raji cells was analyzed by Annexin V/PI binding assay. Incubation time was 48 h. The following indications apply to the FIG. 7: Non-treated, cells in culture medium; RTX, rituximab (0.2 µM); RTX+P-EPI, mixture of rituximab and P-EPI (0.2 µM based on rituximab, the concentration of P-EPI was equal to the content of RTX-P-EPI); RTX-EPI, rituximab-EPI conjugate (0.2 µM based on rituximab);

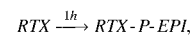

$$RTX \xrightarrow{1h} RTX\text{-}P\text{-}EPI,$$

cells were preblocked by rituximab (2 µM), followed (1 h later) by RTX-P-EPI conjugate (0.2 µM); RTX-P-EPI, RTX-P-EPI conjugate (0.2 µM based on rituximab); IgG-P-EPI, IgG-P-EPI conjugate (0.2 µM based on IgG). Percentage of apoptotic cells was quantified by flow cytometry. All data are presented as mean±SD (n=3). Statistical analysis was performed by one-way analysis of variance (ANOVA) to compare three or more groups (with p value <0.05 indicating statistically significant difference; *<0.05, ***<0.0001, n.s.: no significant difference).

Example 4: Internalization

Confocal Fluorescence Microscopy.
Ramos cells at a density of 2×10$^5$ in 100 µl were incubated with RTX-Cy5 or RTX-P-EPI (3 mg/ml×25 µl) in culture medium at 37° C. for 3 h; then the cells were washed twice with PBS to remove unbound conjugates and plated onto sterile 35-mm glass bottom dishes with 14-mmmicrowells (MatTek Corporation, Ashland, Mass.) for imaging, using Olympus laser scanning confocal microscope (FV 1000).

Flow Cytometry.

$10^6$ Ramos cells in 100 μl in culture medium mixed with RTX-P-EPI (6 mg/ml×5 μl) and incubated at 4° C. for 30 min. Unbound conjugates were removed by washing cells in medium to final volume 500 μl. Cells were incubated at either at 37° C. in medium or 4° C. with $NaN_3$ (0.1%). At indicated time points, 100 μl of cells was removed from culture, then stained with 100 μl secondary antibody (Alexa Fluor® 488 goat-anti human IgG (H+L), 1:200 diluted) and incubated at 4° C. for another 20 min. After washing by PBS twice, labeled cells were analyzed by flow cytometry.

Internalization of Antibody-Polymer-Drug Conjugate.

Figure 8A:
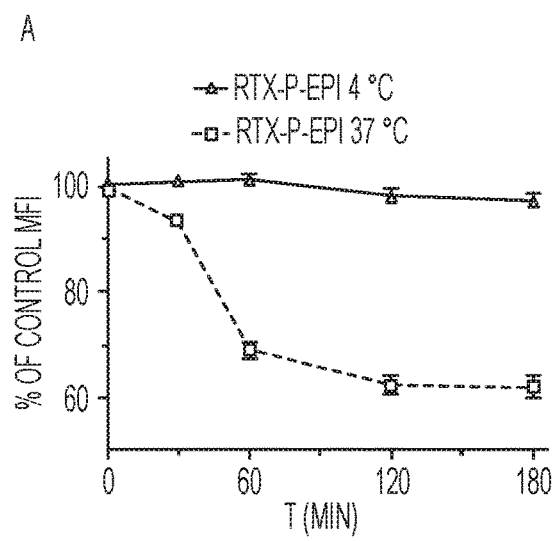
FIGS. 8A-B show the internalization of antibody-polymer-drug conjugate into Ramos cells using flow cytometry (A) and confocal microscopy (B) analysis.
Figure 8B:
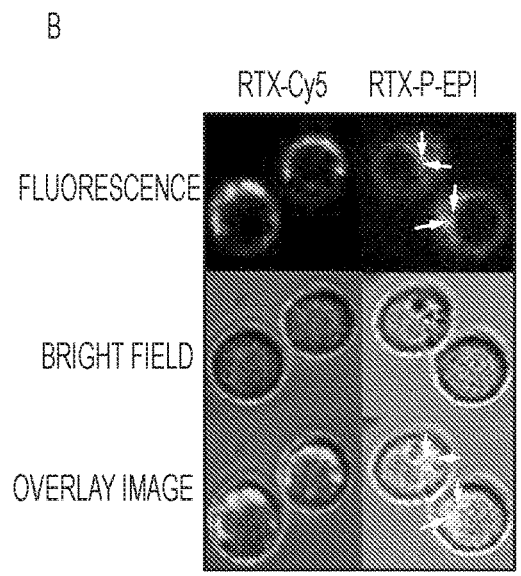

CD20 is a non- or slowly internalizing antigen that remains on the cell surface when bound to a complementary antibody, e.g., RTX (Press, et al., 1989; Law, et al., 2004). To examine whether conjugation of P-EPI to RTX will enhance the internalization of RTX-P-EPI, Ramos cells were incubated in RTX-P-EPI with over-saturating level at 4° C. for 30 min. Cells were washed at 4° C., and then kept at both 37° C. and 4° C. (in the presence of $NaN_3$), permissive and nonpermissive (+ inhibitor) temperature for endocytosis, respectively. At 0, 30 min, 1, 2, and 3 h, cells were stained with Alexa Fluor-488 goat anti-human IgG secondary antibody. Flow cytometry was used to analyze the remaining surface RTX-P-EPI. FIG. 8A shows no detectable change over the 3 h course for the Ramos cells that kept at 4° C. In contrast, surface levels of RTX-P-EPI decreased significantly when the cells were kept at 37° C. Within 3 h, about 40% of RTX-P-EPI was lost from the cell surface, suggesting the conjugate RTX-P-EPI was internalized by the cells. This observation is coincident with a previous report by Law et al. that conjugation of monomethyl auristatin E (MMAE) to RTX resulted in internalization of RTX-vcMMAE (Law, et al., 2004). Furthermore, confocal microscopy images (FIG. 8B) confirmed the internalization of RTX-P-EPI. After incubation at 37° C. for 3 h, fluorescence signals were detected on the surface (like RTX-Cy5) as well as in the cytoplasm of Ramos cells, which indicated that RTX-P-EPI was internalized by the cells.

Example 5: In Vivo Evaluation of Antitumor Efficacy

Localized xenograft model of human B-lymphoma was used to evaluate the efficacy of RTX-P-EPI. Ramos cells ($5×10^6$) in 200 μl of PBS were subcutaneously inoculated in the right flank of 7- to 9-wk-old male NOD SCID mice. Tumor size was measured with a caliper, and tumor volume was calculated according to the formula: Tumor volume ($mm^3$)=½×length×(width), where the length (mm) is the longest and the width (mm) is the shortest dimension of the tumor. When the average tumor size reached 150±50 $mm^3$, treatment was initiated (n=4-5). Mice were intravenously (i.v.) administered via tail vein (on days 11, 14, 17, and 20 after tumor implantation) with RTX-P-EPI and a series of references including unconjugated RTX, non-specific IgG-P-EPI, free EPI directly conjugated RTX-EPI, and combination of RTX with EPI or P-EPI. Body weight variation was computed by the equation: variation=$(W_{Day n}-W_{Day 0})/W_{Day 0}×100\%$. Four doses with 20 mg/kg for RTX (1.5 mg/kg equivalent EPI in 20 mg/kg RTX-P-EPI) on days 11, 14, 17, and 20 (FIG. 9, arrows) were administered via tail vein. Saline was used as non-treated control. RTX, RTX-EPI, mixture of RTX+P-EPI, mixture of RTX+EPI and IgG-P-EPI were also evaluated. The data are presented as mean±SD (n=4-5).

In Vivo Anti-Tumor Efficacy of RTX-P-EPI.

Figure 9:
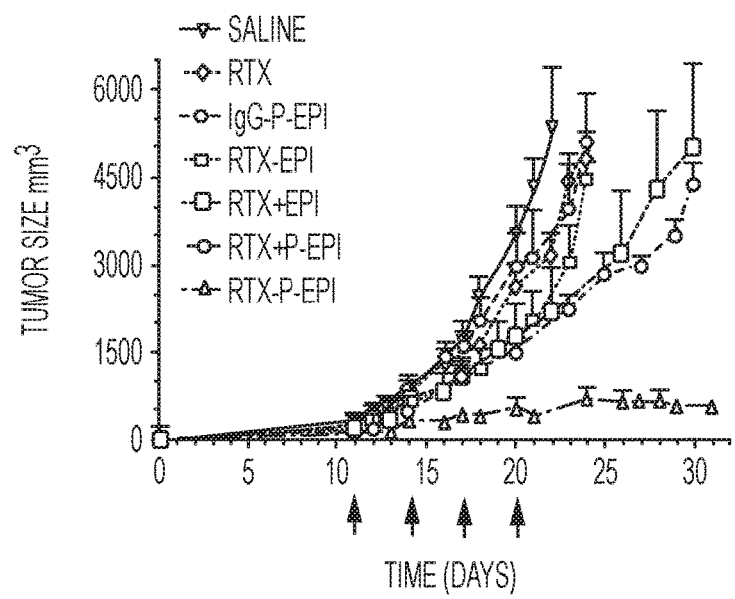
FIG. 9 shows antitumor activity of RTX-P-EPI in a B-cell lymphoma model.

The therapeutic potential of RTX-P-EPI was evaluated in male NOD SCID mice bearing human lymphoma xenografts. NOD SCID mice were subcutaneously implanted with Ramos cells ($5×10^6$ cells/200 μl saline) into the right flank. When tumors reached 100-200 $mm^3$, mice were treated intravenously with 20 mg/kg of RTX or RTX-equivalent dose of RTX-P-EPI (that dose led to an EPI dose of 1.5 mg/kg). Saline was injected as control. For comparison, RTX-EPI, RTX+EPI, RTX+P-EPI and IgG-P-EPI were also administered. Mice were treated with 4 doses at 3-day intervals. There are no significant differences until Day 21 among various treatment groups except saline, which was found the statistical significant difference (the post hoc test P value between RTX-P-EPI versus saline is smaller than 0.05). However, RTX alone, RTX-EPI and the non-specific conjugate IgG-P-EPI showed marginal effects. Mice treated with these regimens were soon killed due to rapidly tumor development. By Day 30, significant differences were found in the remaining three treatments. The P value of ANOVA is 0.0116, and both of the post hoc test P values of RTX-P-EPI versus RTX+P-EPI and versus RTX+EPI are less than 0.05 (FIG. 9).

The targeting effect was clearly demonstrated by comparison of RTX-P-EPI with a non-specific conjugate IgG-P-EPI, as both conjugates have similar Mw, thus the enhanced permeability and retention (EPR) effect could be ruled out. Importantly, by comparing RTX-P-EPI with equivalent RTX+EPI and RTX+P-EPI, the conjugate RTX-P-EPI demonstrated structural synergistic effect.

Figure 14:
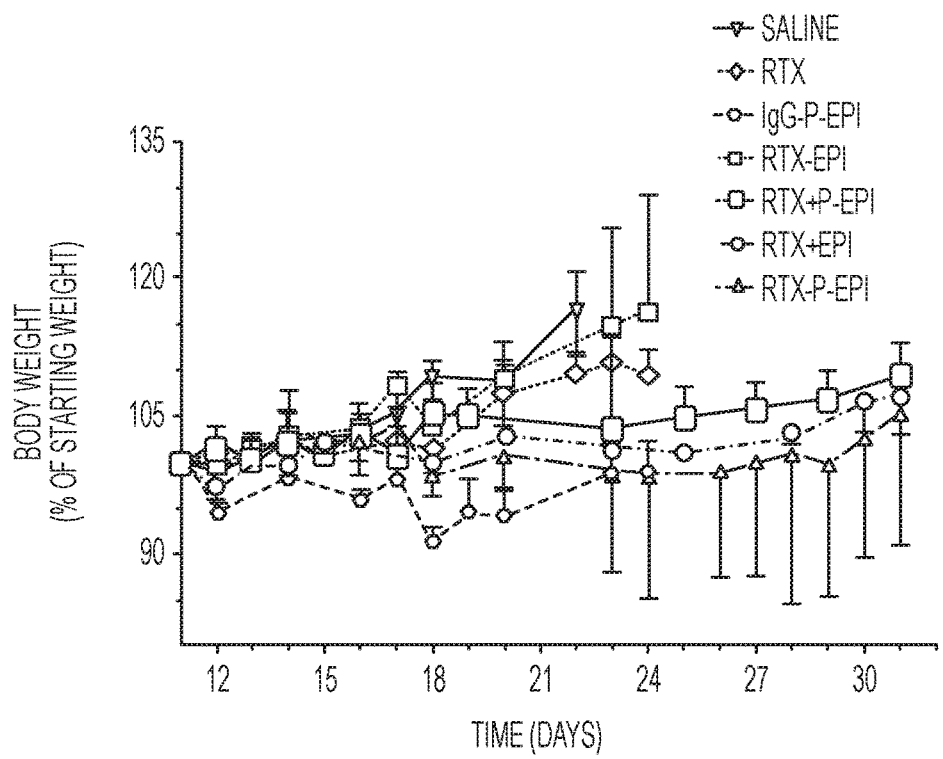
FIG. 14 shows a body weight chart of NOD/SCID mice subcutaneously implanted with Ramos B-cells in the right flank and exposed to different treatments. Body weight is presented as mean±SD (n=4-5).

These results convincingly demonstrated that RTX-P-EPI is more effective in vivo than RTX-EPI, an ADC with a traditional design. In addition, body weight of the mice was closely recorded during and after treatment. The body weight loss of the mice treated with RTX-P-EPI was within acceptable limits and remained stable after withdrawal; there was no observed evidence of increased toxicity of RTX-P-EPI compared to controls (FIG. 14). Four-doses were administered on days 11, 14, 17 and 20.

Example 6: Pharmacokinetics and Biodistribution

The conjugates were radioiodinated by the Iodogen method as previously described (Liu et al., 2009). 7-9 week-old healthy male NOD/SCID mice (n=3) were intravenously injected with $^{125}I$ labeled RTX, RTX-P-EPI or IgG-P-EPI conjugates (0.1 mg, 20 μCi per mouse), respectively. At predetermined intervals, blood samples (10 μl) were taken from the tail vein, and the radioactivity of each sample was measured with Gamma Counter (Packard).

For biodistribution study, 7-9 week-old male NOD SCID mice bearing s.c. Ramos tumors received intravenous injection of $^{125}I$ labeled RTX, RTX-P-EPI, or IgG-P-EPI (0.1 mg, 20 μCi per mouse). At 72 and 96 h after administration, the mice were sacrificed. Various tissues (heart, liver, spleen, lung, kidney, stomach, intestine, muscle, bone, brain and tumor) were harvested, weighed, and counted for radioactivity with Gamma Counter (Packard). Uptake of the conjugate was calculated as the percentage of the injected dose per gram of tissue (% ID/g). Data are presented as mean±standard deviation (n=3).

Pharmacokinetics and Biodistribution of $^{125}$I Labeled Antibody-Polymer-Drug Conjugates.

Figure 10:
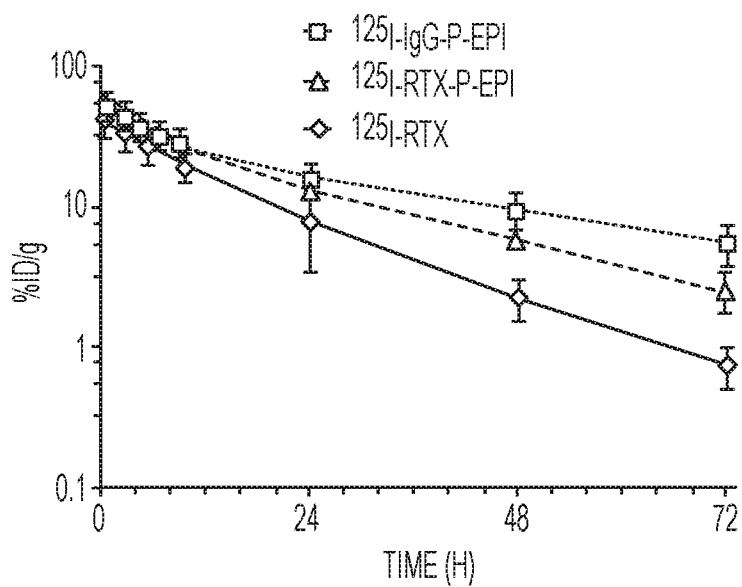
FIG. 10 shows the pharmacokinetic profiles of $^{125}$I-labeled conjugates IgG-P-EPI, RTX and RTX-P-EPI in male NOD SCID mice. Data obtained using the radioactivity count method was plotted as percentage of injected dose per gram of tissue (% ID/g). All data are expressed as mean±standard deviation (n=3).

The pharmacokinetic properties of $^{125}$I labeled RTX, RTX-P-EPI and IgG-P-EPI were evaluated in male NOD SCID mice. Antibody was radiolabeled by $^{125}$I and i.v. injected at 3.5 mg/kg (based on antibody for RTX, RTX-P-EPI, and IgG-P-EPI) single dose. The blood radioactivity time profiles of $^{125}$I-labeled RTX-P-EPI and of RTX demonstrate the following: a) Conjugation of over 20 epirubicin molecules (via multiple linear polymer carriers) to RTX did not accelerate its clearance; and b) Reduction of RTX for conjugation of polymer-precursor did not destabilize the RTX structure via binding to critical disulfide bonds when exposed to sheer stress in vivo (FIG. 10). These results strongly suggest that APDC design described herein will not compromise the pharmacokinetic properties of the antibody (Table 3).

TABLE 3

Pharmacokinetic parameters of $^{125}$I labeled RTX-P-EPI and controls in SCID mice.

|  | RTX-P-EPI | RTX | IgG-P-EPI |
| --- | --- | --- | --- |
| $T_{1/2, \alpha}$ (h) | 2.45 ± 3.99 | 0.78 ± 0.55 | 2.59 ± 1.35 |
| $T_{1/2, \beta}$ (h) | 21.47 ± 3.55 | 15.06 ± 0.10 | 27.35 ± 5.93 |
| AUC (% ID h/mL) | 1160.80 ± 141.55 | 716.46 ± 66.64 | 1315.89 ± 255.06 |
| CL (mL/h) | 0.09 ± 0.01 | 0.14 ± 0.01 | 0.08 ± 0.01 |
| MRT (h) | 27.62 ± 1.95 | 20.37 ± 1.22 | 36.81 ± 7.05 |
| Vss (mL) | 2.41 ± 0.41 | 2.85 ± 0.09 | 2.81 ± 0.38 |

$T_{1/2,\alpha}$ = initial half-life;
$T_{1/2,\beta}$ = terminal half-life;
AUC = total area under the blood concentration versus time curve;
% ID = percentage of injected dose;
CL = total body clearance;
MRT = mean residence time;
Vss = steady-state volume of distribution;
1F5 = murine anti-CD20 IgG2a antibody (control).
Data are presented as mean ± standard deviation (n = 3).
The blood pharmacokinetic parameters for the radiotracer were analyzed using a two compartmental model with PKSolver.

Figure 11A:
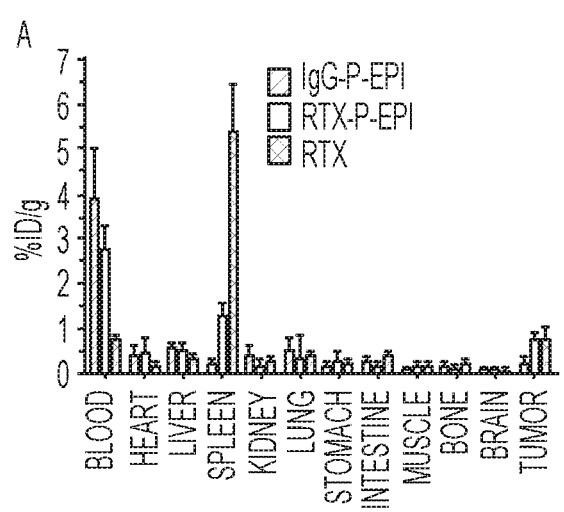
FIGS. 11A-B show the biodistribution of $^{125}$I-labeled RTX, RTX-P-EPI, and non-specific IgG-P-EPI in Ramos lymphoma-bearing NOD SCID mice at 72 h after intravenous administration (A).
Figure 11B:
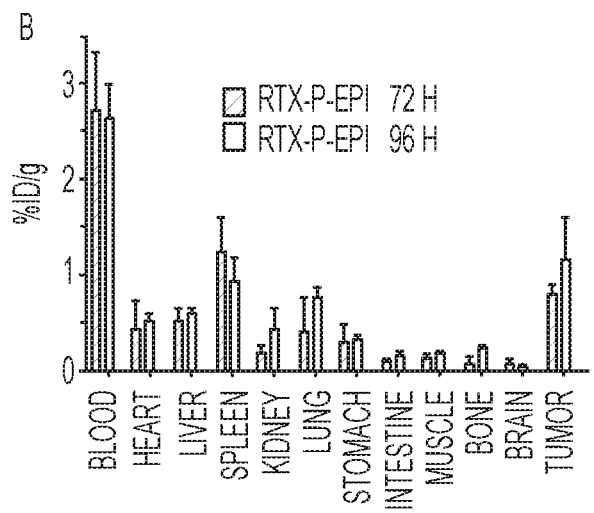

The biodistribution of RTX, RTX-P-EPI and IgG-P-EPI labeled by $^{125}$I in male NOD SCID mice bearing s.c. xenograft tumor model was also compared. At 72 h after intravenous injection, tumor uptake of $^{125}$I-RTX-P-EPI was higher than that in major organs except spleen. Particularly, the level of targeted antibody-polymer-drug conjugate in the tumor ($^{125}$I-RTX-P-EPI, 0.75% ID/g tissue), which was comparable to that of RTX (0.71% ID/g tissue), was 3-fold higher than the non-targeted conjugate ($^{125}$I-IgG-P-EPI, 0.25% ID/g tissue) (FIG. 11). These results suggest that although attachment of polymer-drug precursors to RTX results in partial loss of binding affinity, long-circulation property of RTX-P-EPI enables to achieve comparable tumor uptake as RTX in the antibody-polymer-drug conjugate model disclosed herein.

References

Alley, S. C., Okeley, N. M., Senter, P. D., 2010. Antibody-drug conjugates: targeted drug delivery for cancer. Curr. Opin. Chem. Biol. 14 (4), 529-537

Braslawsky G R, Kadow K, Knipe J, McGoff, K., Edson, M., Kaneko, T., Greenfield, R. S., 1991. Adriamycin (hydrazone)-antibody conjugates require internalization and intracellular acid hydrolysis for antitumor activity. Cancer Immunol. Immunother. 33, 367-374.

Casi, G., Neri, D., 2012. Antibody-drug conjugates: Basic concepts, examples and future perspectives. J. Controlled Release 161, 422-428.

Chari, R. V., Miller, M. L., Widdison, W. C., 2014. Antibody-drug conjugates: An emerging concept in cancer therapy. Angew. Chem. Int. Ed. 53, 3796-3827.

Cheson, B. D., Leonard, J. P., 2008. Monoclonal antibody therapy for B-cell non-Hodgkin's lymphoma. New Engl. J. Med. 359, 613-626.

Chu, T.-W., Kopeček, J., 2015. Drug-free macromolecular therapeutics—a new paradigm in polymeric nanomedicines. Biomaterials Sci. 3, 908-922.

Chu, Y. W., Polson, A., 2013. Antibody-drug conjugates for the treatment of B-cell non-Hodgkin's lymphoma and leukemia. Future Oncol. 9, 355-368.

Chytil, P., Etrych, T., Kříž, J., Šubr. V., Ulbrich, K., 2010. N-(2-Hydroxypropyl)methacrylamide-based polymer conjugates with pH-controlled activation of doxorubicin for cell-specific or passive tumour targeting. Synthesis by RAFT polymerisation and physicochemical characterisation. J. Controlled Release 41, 473-482.

Ducry, L., Stump, B., 2010. Antibody-drug conjugates: Linking cytotoxic payloads to monoclonal antibodies. Bioconjugate Chem. 21, 5-13.

Etrych, T., Mrkvan, T., Říhová, B., Ulbrich, K., 2007. Star-shaped immunoglobulin-containing HPMA-based conjugates with doxorubicin for cancer therapy. J. Controlled Release 122, 31-38.

Etrych, T., Strohalm, J., Kovář, L., Kabešová, M., Říhová, B., Ulbrich, K., 2009. HPMA copolymer conjugates with reduced anti-CD20 antibody for cell-specific drug targeting. I. Synthesis and in vitro evaluation of binding efficacy and cytostatic activity. J. Controlled Release 140, 18-26.

Gergel, D., Cederbaum, A.-I., 1996. Inhibition of the catalytic activity of alcohol dehydrogenase by nitric oxide is associated with S nitrosylation and the release of zinc. Biochemistry 35, 16186-16194.

Hongrapipat, J., Kopečková, P., Liu, J., Prakongpan, S., Kopeček, J., 2008. Combination chemotherapy and photodynamic therapy with Fab' fragment targeted HPMA copolymer conjugates in human ovarian carcinoma cells. Mol. Pharmaceutics 5, 696-709.

Jagadeesh, D., Smith, M. R., 2016. Antibody drug conjugates (ADCs): Changing the treatment landscape of lymphoma. Curr. Treat. Options Oncol. 17, 55. Doi: 10.1007/s11864-016-0428-y.

Jelínková, M., Strohalm, J., Plocová, D., Šubr. V., Šťastný, M., Ulbrich, K., Říhová, B., 1998. Targeting of human and mouse T-lymphocytes by monoclonal antibody-HPMA copolymer-doxorubicin conjugates directed against different T-cell surface antigens. J. Controlled Release 52, 253-270.

Kamei, S., Kopeček, J., 1995. Prolonged blood circulation in rats of nanospheres surface-modified with semitelechelic poly[N-(2-hydroxypropyl)methacrylamide]. Pharmaceutical Res. 12, 663-668.

Kopeček, J., Bažilová, H., 1973. Poly[N-(2-hydroxypropyl)methacrylamide]. 1. Radical polymerization and copolymerization. Eur. Polym. J. 9, 7-14.

Kovář, M., Strohalm, J., Etrych, T., Ulbrich, K., Říhová, B., 2002. Star structure of antibody-targeted HPMA copolymer-bound doxorubicin: A novel type of polymeric conjugate for targeted drug delivery with potent antitumor effect. Bioconjugate Chem. 13, 206-215.

Law, C.-L., Cerveny, C. G., Gordon, K. A., Klussman, K., Mixan, B. J., Chace, D. F., Meyer, D. L., Doronina, S. O., Siegall, C. B., Francisco, J. A., Senter, P. D., Wahl, A. F., 2004. Efficient elimination of B-lineage lymphomas by anti-CD20—auristatin conjugates. Clin. Cancer Res. 10, 7842-7851.

Lidický, O., Janoušková, O., Strohalm. J., Alam, M., Klener, P., Etrych, T., 2015. Anti-lymphoma efficacy comparison of anti-CD20 monoclonal antibody-targeted and non-targeted star-shaped polymer-prodrug conjugates. Molecules 20, 19849-19864.

Liu, J., Kopečková, P., Baler, P., Wolf, P., Pan, H., Bauer, H., Elsässer-Beile, U., Kopeček, J., 2009. Biorecognition and subcellular trafficking of HPMA copolymer—anti-PSMA antibody conjugates by prostate cancer cells. Mol. Pharmaceutics 6, 959-970.

Leget, G. A., Czuczman, M. S., 1998. Use of rituximab, the new FDA-approved antibody. Curr. Opin. Oncol. 10, 548-551.

Lu, Z.-R., Kopečková, P., Wu, Z., Kopeček, J., 1998. Functionalized semitelechelic poly[N-(2-hydroxypropyl)methacrylamide] for protein modification. Bioconjugate Chem. 9, 793-804.

Lu, Z.-R., Kopečková, P., Kopeček, J., 1999. Polymerizable Fab' antibody fragments for targeting of anticancer drugs. Nature Biotechnol. 17, 1101-1104.

Lu, Z.-R., Shiah, J.-G., Kopečková, P., Kopeček, J., 2003. Polymerizable Fab' antibody fragment targeted photodynamic cancer therapy in nude mice. STP Pharma Sci. 13, 69-75.

Mehta, A., Forero-Torres, A., 2015. Development and integration of antibody-drug conjugate in non-Hodgkin lymphoma. Curr. Oncol, Rep. 17(9): 41. Doi: 10.1007/s11912-015-0466-9.

Mitsukami, Y., Donovan, M. S., Lowe, A. B., McCormick, C. L., 2001. Water-soluble polymers. 81. Direct synthesis of hydrophilic styrenic-based homopolymers and block copolymers in aqueous solution via RAFT. Macromolecules 34, 2248-2256.

Omelyanenko, V., Kopečková, P., Gentry, C., Shiah, J.-G., Kopeček, J., 1996. HPMA copolymer—anticancer drug—OV-TL16 antibody conjugates. 1. Influence of the method of synthesis on the binding affinity to OVCAR-3 ovarian carcinoma cells in vitro. J. Drug Targeting 3, 357-373.

Pimm, M. V., Perkins, A. C., Duncan, R., Ulbrich, K, 1993. Targeting of N-(2 hydroxypropyl)methacrylamide copolymer-doxorubicin conjugate to the hepatocyte galactose receptor in mice: visualisation and quantification by gamma scintigraphy as a basis for clinical targeting studies. *J. Drug Target.* 1, 125-131.

Pola, R., Laga, R., Ulbrich, K., Sieglová, I., Král, V., Fábry, M., Kabešová, M., Kovář, M., Pechar, M., 2013. Polymer therapeutics with a coiled coil motif targeted against murine BCL1 leukemia. Biomacromolecules 14, 881-889.

Press, O. W., Farr, A. G., Borroz, K. I., Anderson, S. K., Martin, P. J., 1989. Endocytosis and degradation of monoclonal antibodies targeting human B-cell malignancies. Cancer Res. 49, 4906-4912.

Richter, M., Yumul, R., Saydaminova, K., Wang, H., Gough, M., Baldessari, A., Cattaneo, R., Lee, F., Wang, C. H., Jang, H., Astier, A., Gopal, A., Carter, D., Lieber, A., 2016. Preclinical safety, pharmacokinetics, pharmacodynamics, and biodistribution studies with Ad35K++ protein: a novel rituximab cotherapeutic. Mol. Ther. Methods Clin. Dev. 5, 16013.

Říhová, B., Kopeček, J., 1985. Biological properties of targetable poly[N-(2-hydroxypropyl)methacrylamide]—antibody conjugates. J. Controlled Release 2, 289-310.

Říhová, B., Kopečková, P., Strohalm, J., Rossmann, P., Větvička, V., Kopeček, J., 1988. Antibody directed affinity therapy applied to the immune system: in vivo effectiveness and limited toxicity of daunomycin conjugates to hpma copolymers and targeting antibody. Clin. Immunol. Immunopathol. 46, 100-114.

Říhová, B., Strohalm, J., Kubáčková, K., Jelínková, M., Hovorka, O., Kovář, M., Plocová, D., Šírová, M., Šťastný, M., Rozprimová, L., Ulbrich, K., 2002. Acquired and specific immunological mechanisms co-responsible for efficacy of polymer-bound drugs. J. Controlled Release 78, 97-114.

Sapra, P., Allen, T. M., 2002. Internalizing antibodies are necessary for improved therapeutic efficacy of antibody targeted liposomal drugs. Cancer Res. 62, 7190-7194.

Seyfizadeh, N., Seyfizadeh, N., Hasenkamp, J., Huerta-Yepez, S., 2016. A molecular perspective on rituximab: A monoclonal antibody for B cell non-Hodgkin lymphoma and other affections. Crit. Rev. Oncol. Hematol. 97, 275-290.

Shiah, J.-G., Sun, Y., Kopečková, P., Peterson, C. M., Straight, R. C., Kopeček, J., 2001. Combination chemotherapy and photodynamic therapy of targetable N-(2-hydroxypropyl)methacrylamide copolymer—doxorubicin/mesochlorin $e_6$-OV-TL16 antibody immunoconjugates. J. Controlled Release 74, 249-253.

Siegel, R., Miller, K. D., Jemal, A., 2016. Cancer Statistics, 2016. *CA Cancer J. Clin.* 66, 7-30

Tao, L., Liu, J., Xu, J., Davis, T P., 2009. Synthesis and bioactivity of poly(HPMA)-lysozyme conjugates: The use of novel thiazolidine-2-thione coupling chemistry, *Org. Biomol. Chem.* 7, 3481-3485

Tappertzhofen, K., Metz, V. V., Hubo, M., Barz, M., Postina, R., Jonuleft, H., Zentel, R., 2013. Synthesis of maleimide-functionalized HPMA copolymers and in vitro characterization of the aRAGE- and human immunoglobulin (huIgG)-polymer conjugates. Macromol. Biosci. 13, 203-214.

Tappertzhofen, K., Bednarczyk, M., Koynov, K., Bros, M., Grabbe, S., Zentel, R., 2014. Toward anticancer immunotherapeutics: Well-defined polymer-antibody conjugates for selective dendritic cell targeting. Macromol. Biosci. 14, 1444-1457.

Tolcher, A. W., Sugarman, S., Gelmon, K. A., 1999. Randoomized phase II study of BR96-doxorubicin conjugate in patients with metastatic breast cancer. J. Clin Oncol. 17, 478-484.

Ulbrich, K., Šubr. V., Strohalm, J., Plocová, D., Jelínková, M., Říhová, B., 2000. Polymeric drugs based on conjugates of synthetic and natural macromolecules. I. Synthesis and physico-chemical characterisation. J. Controlled Release 64, 63-79.

Wang, D., Kopečková, P., Minko, T., Nanayakkara, V., Kopeček, J., 2000. Synthesis of star-like N-(2-hydroxypropyl)methacrylamide copolymers—potential drug carriers. Biomacromolecules 1, 313-319.

Wang, T., Kievit, F. M., Veiseh, O., Arami, H., Stephen, Z. R., Fang, C., Liu, Y., Ellenbogen, R. G., Zhang, M., 2013. Targeted cell uptake of noninternalizing antibody through conjugation to iron oxide nanoparticles in primary central nervous system lymphoma. World Neurosurg. 80, 134-141.

Wu, A. M., Senter, P. D., 2005. Arming antibodies: prospects and challenges for immunoconjugates. Nat. Biotechnol. 23, 1137-1146

Yang, J., Zhang, R., Radford, D. C., Kopeček, J., 2015. FRET-trackable biodegradable HPMA copolymer-epirubicin conjugates for ovarian carcinoma therapy. J. Controlled Release 218, 36-44 (2015).

Yang, J., Kopeček, J., 2016. Design of smart HPMA copolymer-based nanomedicines. J. Controlled Release 240, 9-23.

Zelenetz, A. D., Gordon L. I., Wierda, W. G., Abramson, J. S., Advani, R. H., Andreadis, C. B., Bartlett, N., Byrd, J. C., Czuczman, M. S., Fayad, L. E., Fisher, R I., Glenn, M. J., Harris, N. L., Hoppe, R. T., Horwitz, S. M., Kelsey, C. R., Kim, Y. H., Krivacic, S., LaCasce, A. S., Nademanee, A., Porcu, P., Press, O., Rabinovitch, R., Reddy, N., Reid, T., Saad, A. A., Sokol, L., Swinnen, L. J., Tsien, C., Vose, J. M., Yahalom, J., Zafar, N., Dwyer, M., Sundar, H., 2014. Non-Hodgkin's lymphomas, version 4.2014. National comprehensive cancer network, 12, 1282-1303.

Zhang, L.-B., Zhao, W.-G., Liu, X.-Y., Wang, G.-L., Wang, Y., Li, D., Xie, L.-Z., Gao, Y., Deng, H.-T., Gao, W.-P., 2015. Site-selective in situ growth of fluorescent polymer-antibody conjugates with enhanced antigen detection by signal amplification. Biomaterials 64, 2-9.

Figure 15A:
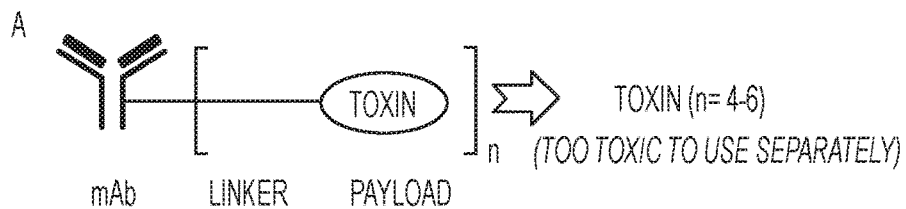
FIGS. 15A-B is a schematic illustration of a comparison of existing antibody-drug conjugates (A) and the antibody-polymer-drug conjugates (B).
Figure 15B:
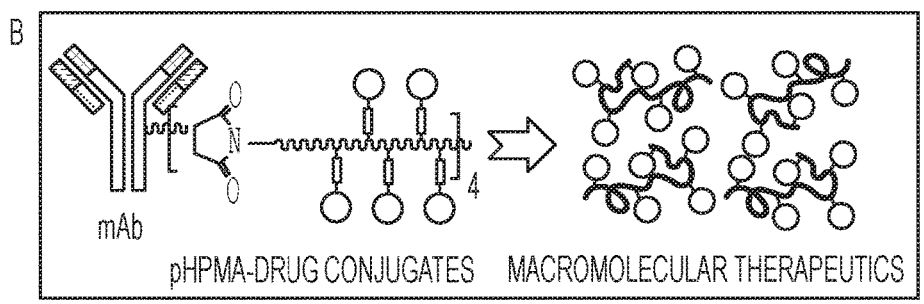

Example 7: Antibody-Polymer-Drug Conjugates for Treatment of B-Cell Non-Hodgkin's Lymphomas The goal of the experiments disclosed herein is to develop a new class of antibody-drug conjugate with improved treatment outcomes in patients with lymphomas. An example of new design is shown in FIG. 15: Linear water-soluble N-(2-hydroxypropyl)methacrylamide (HPMA) polymer-drug conjugates terminated with maleimide group can be selectively attached to Rituximab, a first FDA approved mAb for treatment of lymphomas. Compared with current antibody-drug conjugates, the distinct features of the new design includes, but are not limited to: 1) increasing payload but without changing number of binding sites; 2) synergistic potential of immunotherapy combined with established macromolecular therapy; 3) improved pharmacokinetics and immunogenicity; 4) Lower risk of off-target toxicity through the use of a cytotoxic agent with a favorable therapeutic index; and 5) low risk but high value for clinical development.

The significance of the antibody-polymer-drug conjugates is the development of an efficacious and safe therapeutic agent for the improvement in the treatment efficacy of lymphomas, and cancer.

It is estimated by the American Cancer Society that approximately 81,080 new cases of lymphoma will be diagnosed in the United States in 2016, 72,580 of which are Non-Hodgkin lymphoma (NHL), the most common hematologic malignancy. NHL is the $6^{th}$ most common cancer and the $9^{th}$ leading cause of cancer death [2]. Treatment of NHL is challenging because the disease comprises over 35 different subtypes with the most prevalent types being diffuse large B cell lymphoma (DLBL), follicular lymphoma (FL) and mantle cell lymphoma (ML) [3]. Eighty-five percent of NHLs are of B-cell origin [4].

Conventional chemotherapy and radiotherapy are associated with significant adverse effects; the most significant of which are cytopenias leading to increased risks of infections and bleeding. More than 95% of B-cell lymphomas bear the cell surface antigen CD20 [4]. The anti-CD20 monoclonal antibody Rituximab is the first FDA approved monoclonal antibody for treatment of B-cell NHLs [5]. With the development of modern chemotherapy protocols and targeted therapies, much progress has been made over the past 2 decades. Rituximab in combination with chemotherapy still remains standard in the treatment of NHL [6]. Options for treating NHL include chemotherapy, radiation, biotherapy and stem cell transplant [5]. Unfortunately, besides the severe side effects, relapsed or resistant disease remains a major cause of treatment failure. Thus, the need for new, improved therapeutic strategies is evident.

Rituximab and Rituximab Combined Chemotherapy.

Rituximab (RTX) is a mouse/human chimeric monoclonal antibody targeting CD20. RTX induces cell killing through complement-dependent cytotoxicity (CDC), antibody dependent cell cytotoxicity (ADCC), antibody-dependent cell-mediated phagocytosis, and direct cell apoptosis. It is effective as a single agent and in combination with chemotherapy in the treatment of CD20-postive B-cell malignancies, including NHL and chronic lymphocytic leukemia (CLL). RTX has also been used for the treatment of some autoimmune diseases including rheumatoid arthritis [7].

While active in the first-line setting, RTX is less effective in patients with relapsed lymphoma. For example, 40% of the patients with low-grade NHL responded to RTX re-treatment upon disease progression or relapse if they had received RTX before. Consequently, these patients often require alternative treatments [8].

Addition of RTX to the standard first line combination of cyclophosphamide, doxorubicin (DOX), vincristine and prednisone (R-CHOP) results in significantly better outcomes compared to CHOP alone but without increased toxicity. Numerous in vitro and in vivo data show that RTX synergizes with chemotherapy by sensitizing chemoresistant tumor cells to cytotoxic drugs, including purine nucleoside analogs (fludarabine, cladribine and pentostatin), pyrimidine nucleoside analog (gemcitabine), DNA-damaging agents (cisplatin, DOX), microtubule poisons (paclitaxel, vincristine), acadesine, dexamethasone, and retinoids [9].

Rituximab Chimeric Structure.

Binding regions from original murine anti-human CD20, consisting of variable regions of immunoglobulin heavy and light chains, are fused to human IgG1 heavy-chain and human kappa light-chain constant regions. Fc portion from human IgG1 was selected for its ability to fix complement and activate antibody-dependent cellular cytotoxicity [8].

Epirubicin is the 4'-epimer of DOX, the most commonly used anthracycline for the treatment of NHL. DOX inhibits DNA replication, transcription and repair by binding to the nucleic acids [10]. Epirubicin is considered one of the most active cancer chemotherapeutic drugs, particularly in the setting of metastatic disease. It has shown equivalent cytotoxicity to DOX in human ovarian cancer cells, but lower cardiotoxicity and myelotoxicity at equimolar doses. Thus, epirubicin has a better therapeutic index than DOX and therefore is an excellent candidate for the treatment of NHL [11,12].

Antibody-drug conjugates (ADCs) constitute one of the most promising class of targeted therapy for cancer [1,13-16]. These prodrugs consist of monoclonal antibodies (mAbs) linked to drugs or toxins. They selectively deliver toxic moieties to tumor cells. As such, they greatly improve the therapeutic index compared to traditional chemotherapeutic agents. However, the therapeutic efficacy and safety of ADCs are highly dependent on linker stability and payload toxicity. A critical parameter is payload number on a single antibody (drug antibody ratio or DAR), as over-attachment will disturb mAb immunoaffinity [17,18]. Generally, a limited number of toxin moieties can be attached to one Ab molecule (usually DAR 4-6). Consequently, extremely toxic agents such as calicheamycin or auristatin monomethyl ester (MMAE) with $IC_{50}<1$ nM have to be employed in order to obtain sufficient efficacy for target cell death. Such ADCs have shown very promising results in the clinic. However, free mAb are still present due to the inherent heterogeneous properties of ADCs, and over-labeling of ADCs occurs with resultant lack of efficacy and increased toxicities. This was the major problem with the anti-CD33 antibody-calicheamycin conjugate (Gemtuzumab, Ozogamycin or Mylotarg), the first FDA approved ADC for the treatment of acute myeloid leukemia (AML). It was withdrawn from the market in 2010 [19,20]. Currently, over 30 ADCs are in clinical trials [16], but two ADCs, Brentuximab vedotin (Adcetris®) [21] and Trastuzumab emtansine (Kadcyla®) [22], are approved on the market.

As mentioned above, conjugation of drugs to an antibody potentially impacts efficacy, toxicity and stability of the resulting products [23]. Typically, conjugation takes place at a solvent accessible lysine or cysteine. A human IgG comprises about 100 lysine residues, half of them located at both heavy chain and light chain, and potentially can be modified, resulting in 0-8 DAR as shown in FIG. 16A. This implicates that a wide range of in vivo pharmacokinetic properties will be generated with this unspecific approach. Cysteine conjugation occurs after reduction of four interchain disulfide bonds that yields ≤8 exposed sulfhydryl groups. The resulting ADCs have a lower degree of heterogeneity (FIG. 16B) [24]. Two FDA-approved ADC therapeutics, brentuximab vedotin (Adcetris®) and ado-trastuzumab emtansine (Kadcyla®), are produced by lysine and cysteine conjugations, respectively.

Polymer-Drug Conjugates and Polymer-Based Antibody-Drug Conjugates Passive & Active Targeting.

The concept of polymer-drug conjugates was developed to address sub-optimal bioactivity and non-specificity of low-molecular weight drugs. Attachment of drugs to polymer carrier improves pharmacokinetics and accumulation of drugs in solid tumors through the enhanced permeability and retention (EPR) effect (also called passive targeting), resulting in enhanced therapeutic efficacy and reduced adverse side effects [25]. Moreover, it is well known that polymer-drug conjugates have different cell-entry mechanism compared to free drug. Consequently, they have the potential to overcome multidrug resistance (MDR) caused by exclusion of free drugs by the ATP driven P-glycoprotein and similar efflux pumps [26].

The use of polymeric drug delivery systems is an established approach for improvement of cancer chemotherapy. For example, KT-1 (2P-EPI), the $2^{nd}$ generation HPMA polymer-epirubicin conjugate, showed much longer terminal half-life (33.22 h) than free drug EPI (9-20 min) [27]. In a preclinical evaluation, both EPI and KT-1 were administered at a dose of 5 mg/kg EPI equivalent to mice bearing A2780 human ovarian carcinoma xenografts (s.c model). KT-1 was substantially more active than EPI. In the EPI group, mice had to be sacrificed on day 20 as the tumor had reached 1772±840% of the baseline, whereas there were no observable tumor in mice treated with KT-1 even at day 100 [27]. Complete tumor regression and long-term inhibition of tumorigenesis are attributed to long circulation time and sufficient extravasation of the conjugates KT-1 at the tumor site through EPR effect. This result suggests that KT-1 conjugate (long-circulating EPI conjugate) may be able to arrest both tumor progenitor cells and differentiated cells [28].

Antibody and/or antibody Fab' fragment have been also incorporated into HPMA copolymers as targeting moieties to improve the therapeutic outcome and to reduce the toxicity of anticancer agents [29-32]. For example, a comparison of the efficacy between non-targeted and OV-TL16 mAb fragment-targeted HPMA copolymer-mesochlorin $e_6$ conjugates (P-Mce$_6$ vs P-Fab'-Mce$_6$) for treatment of OVCAR-3 xenografts in nude mice has been performed. Results clearly indicate the advantage of targeted treatment [30].

Impact of Conjugation Chemistry on Binding Affinity of Modified Antibody Conjugates.

A detailed study of coupling OV-TL16 antibody and its Fab' fragment to HPMA copolymer—drug (ADR, Mce$_6$) via different approaches on the binding affinity of the conjugates to OVCAR-3 cells was conducted [31]. Differences in Ka (affinity constant) suggest random modification of lysine residues via amide bond lead to conjugate heterogeneity and impaired antigen binding [32]; and site-specific modification results in superior property.

The use of such polymer-based platforms to create ADCs has recently been reported. For example, Fleximer, a polyacetal copolymer containing a modestly potent *Vinca* derivative and pendant thiol groups has been synthesized [33]. Trastuzumab was selected as the targeting moiety, and its amino groups from lysine residues were modified into maleimido groups using succinimidyl-4-(N-maleimidomethyl)cyclohexane-1-carboxylate (SMCC) with the average degree of substitution 5 to 6 per mAb. Fleximer was attached to Trastuzumab via lysine residue. This ADC with DAR of 20 was evaluated in preclinical models of human breast and gastric cancers [34]. Although the results indicate a robust strategy to expand the scope of drug selection for ADCs in clinical development, there were some drawbacks such as significant accelerated blood clearance, half loss of binding affinity and too high toxicity of the drug payload.

The antibody-polymer-drug design described herein has advantages including a simple structure, proven safety of the polymer, and utilization of a current effective drug and commercially available antibody. Also, the synthesis procedures disclosed herein are versatile; they provide a platform for the preparation of a large variation of antibody-polymer-drug conjugates with tailor-made properties, such as variable mAbs and drug composition.

The APDC design disclosed herein integrates two traditional approaches (antibody targeting and polymer therapeutics) into one 'hybrid' product. As a result, increased payload without changing the number of binding sites is achieved by controllable site-specific attachment of polymer-drug conjugates to an antibody. Common problems caused by high drug-coupling in ADCs (for example, increased aggregation, decreased stability, faster systemic clearance, loss of antibody's binding to tumor, etc.) can be minimized. These conjugates disclosed herein will possess advantages of both antibody-drug conjugates with high specificity and macromolecular therapeutics, as well as improved stability of the antibody and prolong the conjugate blood circulation. Moreover, a Fluorescence (Förster) Resonance Energy Transfer (FRET) imaging strategy can be applied to monitor independent fate of the antibody and drug at the body, tissue and cell levels. This will improve our understanding of in vivo behavior of APDCs and help design and generate efficient and less toxic therapeutics.

Development of Polymer-Based RTX-Epirubicin Conjugates (RTX-P-EPI).

Selection of an antigen target is important for a successful APDC that is safe and efficacious. RTX has been successfully used for the treatment of CD20 positive B-cell lymphomas for over two decades. Thus, both the antibody and the target have been extensively validated in clinical practice. The efficacy of RTX has been increased when used in combination with chemotherapy. EPI, an anthracycline antitumor drug, has been approved for the treatment of various human cancers. Its efficacy and dose-limiting toxicity are well documented. Long-circulating conjugate 2P-EPI enhances antitumor activity compared with free drug EPI [27]. As a drug carrier, HPMA copolymers have been applied on hundreds of patients (Phase I/II) since late 1990s, and no immunogenicity, nor toxicity was reported [35-37]. Moreover, clinical results indicate polymer-drug conjugates can be both a powerful anti-cancer agent and an inducer of anti-tumor immunity [38]. Both mAb Rituximab and drug Epirubicin are commercially available.

FIG. 17 shows semitelechelic (ST) HPMA copolymers terminated with maleimide group first prepared by RAFT copolymerization followed by two-step end modification. A typical polymerization process is briefly summarized as follows: HPMA and polymerizable derivative of epirubicin (EPI), N-methacryloylglycylphenylalanylleucylglycine-epirubicin (MA-GFLG-EPI), were added into an ampoule attached to Schlenk-line. 2-cyano-5-oxo-5-(2-thioxothiazolidin-3-yl)pental-2-yl benzodithioate (CTA-TT) was used as chain transfer agent (CTA) and V70 as initiator. The copolymerization proceeded at 40° C. in methanol/DMSO (2:1 v/v) for 20 h. The polymer was isolated by precipitation into ether/acetone. Dithiobenzoate group was removed by reaction with large excess of V70, and maleimide was incorporated by reaction of N-ethylamino maleimide with polymer chain end thiazolidine-2-thione (TT). The average molecular weight and the polydispersity of the conjugate were determined by size exclusion chromatography (SEC) on an AKTA FPLC system. The presence of maleimide group was confirmed by modified Ellman assay; EPI content was measured using UV-vis at 495 nm.

RTX (Genentech) was obtained at a stock concentration of 20 mg/mL. It was buffer exchanged to a concentration 1 mg/mL in 4 mL Tris-HCl (10 mM, 150 mM NaCl, 5 mM EDTA, pH 7.4). TCEP (tris(2-carboxyethyl) phosphine; 10× in $H_2O$) was added to the solution and incubated at 37° C. for 3 h, then purified with ultrafiltration (30,000 MWCO, Amicon®Ultra) to yield Ab-SH. ST-P-EPI was added to the Ab-SH solution and incubated at 37° C. for another 2 h. RTX-P-EPI was obtained after removal of unreacted polymer using SEC purification. Based on the ratio of RTX (BCA assay) and EPI, the DAR was calculated. By changing the feed ratio and reaction time, the substitution of antibody (DAR) can be adjusted.

RTX-EPI was synthesized as control and non-specific IgG-P-EPI was synthesized to ascertain the targeting effect. IgG-P-EPI was obtained by following a similar procedure to what was described above except that RTX was replaced with a human IgG. The characterization of conjugates is summarized in Table 4.

TABLE 4

Characterization of conjugates.

| | ST-P-EPI | | | | |
|---|---|---|---|---|---|
| | Mn | PDI | EPI/chain | P/mAb | DAR |
| RTX | | N/A | — | — | — |
| RTX-EPI | | N/A | — | — | 2.7 |
| RTX-P-EPI-3.1 | 38 kDa | 1.17 | 6.6 | 3.1 | 20.6 |
| RTX-P-EPI-6.5 | 38 kDa | 1.17 | 6.6 | 6.5 | 42 |
| IgG-P-EPI | 33 kDa | 1.11 | 4.7 | 3.6 | 17 |

To evaluate binding characteristics of various conjugates, Ramos cell line with high CD20 expression was selected as a target. Cells ($2 \times 10^5$ in 400 μL medium) were centrifuged at 2000 g for 5 min, the supernatant was removed. Conjugates with increasing concentration (0.04, 0.2 or 1 μg in 20 μL PBS) were added. IgG-P-EPI and RTX were used for comparison. Cells were incubated at 4° C. for 20 min, washed with medium twice to remove unbound conjugates, then stained with 100 μL secondary antibody (GAH-488, 1:200 diluted) and incubated at 4° C. for another 20 min. Flow cytometry was used to determine mean fluorescence intensity (MFI) of each conjugate sample. Higher MFI indicates more bound conjugates. The results show that IgG-P-EPI barely binds to Ramos cells; as expected, modification of Rituximab with P-EPI partially decreased the binding affinity, which is 'valency' dependent: the more the attachment of polymer-precursor, the more attenuated binding of conjugates.

Figure 7A:
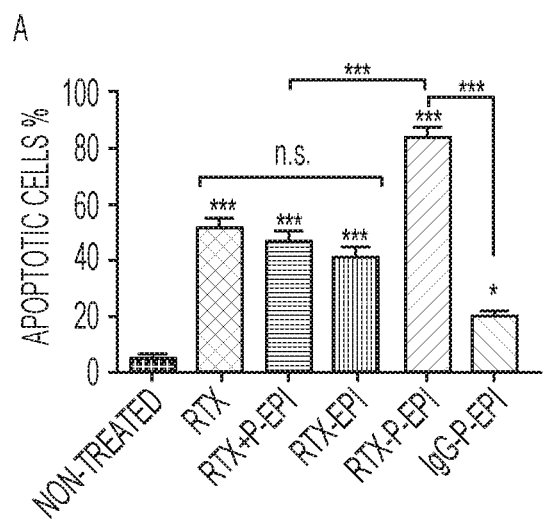
FIGS. 7A-B show in vitro cytotoxicities of conjugates toward Ramos cells (A) and Raji cells (B).

The cytotoxicity of different conjugates toward Ramos and Raji cells (both are CD20-positive Burkitt's lymphoma cell lines) was evaluated, respectively. Cells ($2 \times 10^5$/well) were incubated with RTX and corresponding conjugates at concentration of 0.2 μM RTX equivalent for 24 h (Raji) or 48 h (Ramos). Apoptosis induction of cells was analyzed using Annexin V/PI staining. For comparison, a mixture of RTX and P-EPI (RTX+P-EPI) was also evaluated, in which the concentration of EPI was equivalent to the EPI amount in RTX-P-EPI (in this study, [EPI]=4.12 μM). IgG-P-EPI had minimal cytotoxicity, while RTX-EPI or RTX+P-EPI had similar cytotoxicity as RTX alone. By contrast, RTX-P-EPI had markedly increased cytotoxicity compared with the latter 3 variables (FIG. 7A).

Figure 7B:
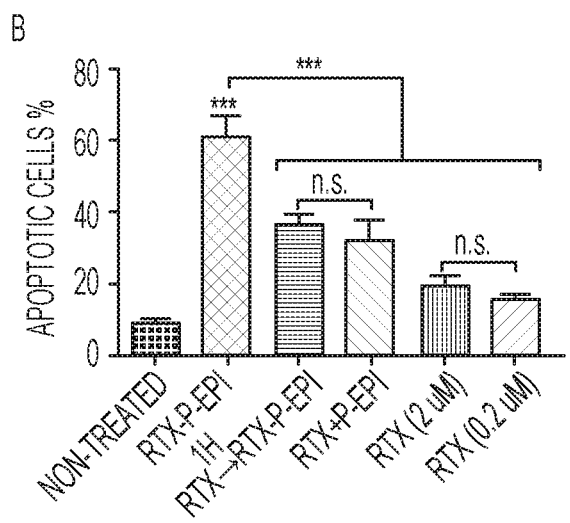

The percent of apoptotic Raji cells did not increase in the RTX group when antibody concentration was increased from 0.2 μM to 2 μM, suggesting that antibody binding to the cells had reached saturation (FIG. 7B). However, when cells were first treated with a high concentration of RTX (2 μM) followed 1 h later by exposure to 0.2 μM equivalent RTX-P-EPI, the percentage of apoptotic cells almost doubled. This suggests that RTX-P-EPI could be active against RTX-pretreated but resistant cells. This raises the likelihood that this system will be efficient in the treatment of RTX-resistant disease.

Figure 18:
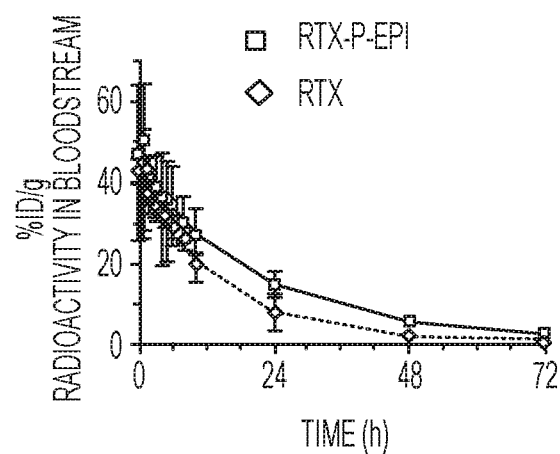
FIG. 18 shows the mean radioactivity expressed as a percentage of the injected dose per gram of blood from mice (n=3).

FIG. 18 shows the pharmacokinetic behavior of $^{125}I$-labeled RTX-P-EPI and of RTX. The blood radioactivity-time profiles demonstrate the following: a) conjugation of over 20 epirubicin molecules (via multiple linear polymer carriers) to RTX did not accelerate its clearance; and b) reduction of RTX for conjugation of polymer-precursor did not destabilize the RTX structure via binding to the important disulfide bonds when exposed to sheer stress in vivo. These results strongly suggest that the APDC design disclosed herein will not compromise the pharmacokinetic properties of the antibody.

The results show that the APDC design disclosed herein does not compromise the targeting ability or pharmacokinetic properties of the antibody. Furthermore, the in vitro and in vivo experiments show that the APDC design disclosed herein leads to highly efficacious anti-lymphoma activity. This APDC design constitutes a platform for the development of novel antibody-targeted therapies for other malignancies.

Synthesis of RTX-P-EPI Conjugates for Lead Optimization

In this system, the targeting effect and therapeutic potential of APDCs are associated with the primary structure of the conjugate, e.g., the Mw of the semitelechelic polymer precursor, the binding site/number, and the drug-to-Ab ratio (DAR). As described herein, when one RTX molecule was attached with >6 P-EPI, the binding ability of the conjugate decreased to ⅓ of native RTX. In some aspects, an average 4 of attachments per mAb will be generated. To reach adequate cytotoxicity (relates to epirubicin amount), three polymer precursors with varying structures will be synthesized.

Synthesis of Polymer Precursors ST-$P_m$-$EPI_n$.

ST-$P_{40}$-$EPI_6$, ST-$P_{40}$-$EPI_8$, and ST-$P_{60}$-$EPI_8$ will be synthesized for investigation of the drug content and molecular weight effect (m and n refer Mw of polymer precursor and EPI content per one HPMA macromolecule, respectively). RAFT polymerization strategy will be used so that the average molecular weight and drug content can be tuned by changing the initial polymerization parameters [40-42]. Importantly, polymer-EPI conjugates with narrow molecular weight distribution and bearing a reactive maleimide group at one chain end will be achieved. The process will minimize the heterogeneity of the conjugates.

Attachment of ST-P-EPI to Rituximab.

Conjugation will be accomplished via reaction of maleimido group at one polymer chain end with thiol groups generated by reduction of antibody disulfide bonds. Rituximab is an IgG1 isotype, which contains two heavy chains and two light chains. Complete reduction with TCEP will result in 8 thiols/antibody [43]. To balance potency with biocompatibility, the goal is to attach on average 4 polymer chains/antibody, as high substitution degree may impair binding affinity [18]. Fortunately, chemically controlled reduction of native disulfides between cysteine residues followed by thiol-ene reaction has been developed to generate site-selective or site-specific attachment with stoichiometry [44-48]. Reduction/reoxidation/reformation chemistries will be performed to control the location and number of substitution sites. Consequently, original activity of the antibody will be maximally retained.

In order to perform subcellular trafficking and PK/biodistribution studies, isotope ($^{125}$I)-labeled and fluorophore (Cy5)-labeled conjugates will be synthesized.

Figure 20:
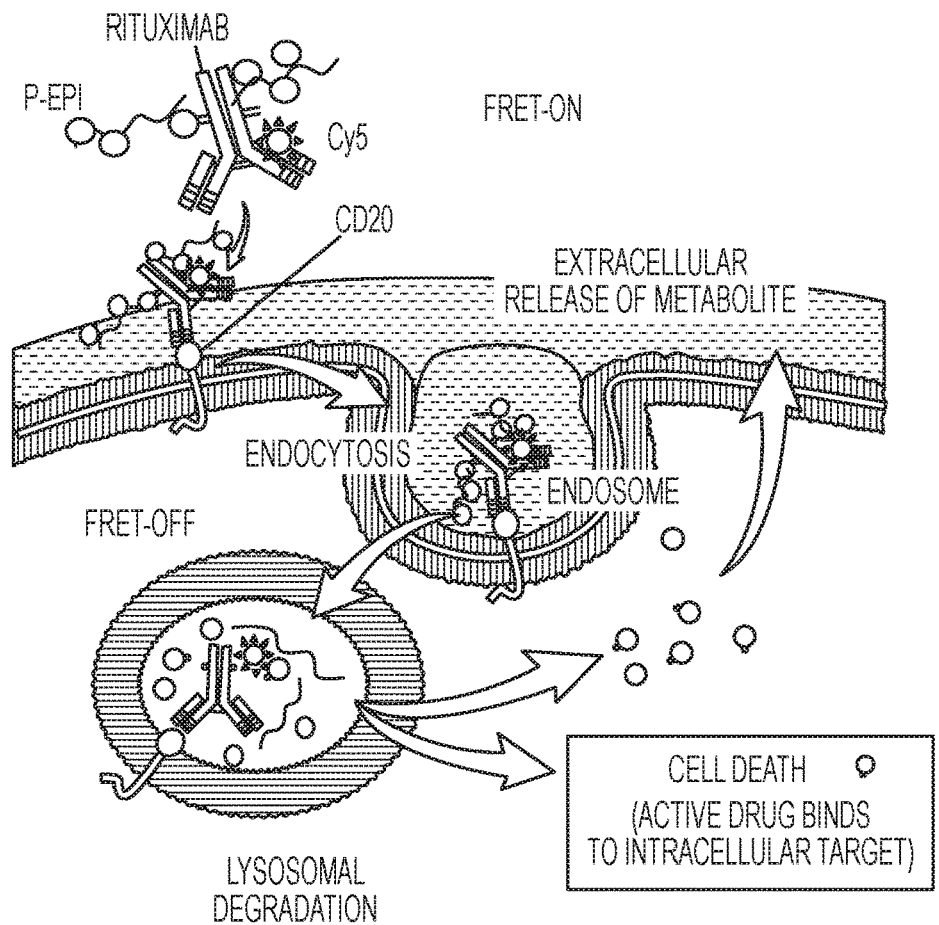
FIG. 20 is a schematic illustration of the fluorescence resonance energy transfer (FRET) that can be used as a tool to track APDC's internalization and subcellular fate

Similarly, human IgG will be used to synthesize non-targeting conjugates to serve as a control (Table 2, FIG. 20.)

Physicochemical Characterization of the Conjugates.

The conjugates will be characterized with Mw, drug content and the drug-to-antibody ratio (DAR) by SEC, HPLC, and UV-vis spectrophotometry, respectively.

Stability of the Conjugates in Buffer.

Conjugates will be incubated in phosphate buffers in physiological range of pH (pH 4-8) at 37° C. The media will be analyzed at different time intervals (initially 2, 4, 8, 12, 24 and 48 h) by HPLC. Free drugs and antibody will serve as controls.

Stability of the Conjugates in Plasma, in the Presence of Human Serum Albumin and in Glutathione.

Although some studies have shown in vivo superiority of non-cleavable thioether linker in reduced toxicity and anti-tumor activity compared to cleavable linker (disulfide or hydrazine linker) [49,50], it might transfer the cytotoxic drug to free sulfhydryls such as the cysteine on human serum albumin (HSA) or glutathione via a retro-Michael reaction [16, 51]. Therefore conjugates will be incubated with HSA/GSH and free EPI or P-EPI released will be determined via HPLC.

In Vitro Enzymatic Degradation.

Conjugates will be incubated with thiol proteinase cathepsin B at Mcilvaine's buffer (1 mM EDTA, 5 mM GSH at pH 5). At predetermined time intervals, small amounts of the incubation solution will be collected. The drug release will be determined by HPLC assay and conjugate degradation by SEC.

The experiments described herein will allow a correlation between the biological activity of the conjugates with their structure to be made.

Evaluation and Optimization of the Antibody Conjugates

The targeting efficiency and cytotoxicity of conjugates RTX-$P_m$-$EPI_n$ will be evaluated. Raji cells with high CD20 expression will be used for in vitro studies involving structural factor optimization. In addition, isotope-labeled and fluorophore-labeled conjugates will be used for pharmacokinetics/biodistribution studies and for monitoring internalization and subcellular fate in order to obtain information on Ab and payloads at the cellular, tissue and whole organism levels. These results will allow the identification of important structural factors and optimization of our design.

Furthermore, in order to determine the breadth of activity of the APDCs, the efficacy of the optimized conjugate RTX-P-EPI toward several different phenotypes of B cell lymphoma cell lines (including both RTX-sensitive and RTX-resistant cells) will be evaluated.

Binding and Cytotoxicity of Conjugates Toward Raji Cells.

First, experiments will be carried out to visualize the targeting effect and determine the binding affinity. To evaluate whether conjugation of various polymer-precursors interferes with antibody-mediated specific targeting effect, $1\times10^6$ Raji cells will be incubated with serial dilutions of the conjugates in ice-cold staining media for 30 min, then washed twice with ice-cold staining medium to remove unbound conjugates. Cells will be then incubated with Alexa Fluor-568 labeled secondary mAb goat anti-human IgG at 10 µg/mL on ice for 30 min and washed as described above. Labeled cells will be analyzed by flow cytometry. Background-corrected mean fluorescence intensity will be determined. Rituximab and IgG-P-EPI will serve as controls.

Cell Growth Inhibition and Apoptosis Analysis.

Raji cells will be incubated with increasing concentrations of each candidate conjugate. Cell viability will be determined at 1, 2, and 3 days of incubation using the MTT assay. The 50% growth inhibitory concentration ($IC_{50}$) of each conjugate will be derived from growth curves. Apoptosis induction by candidate conjugate will be determined using flow cytometry for analysis of Annexin V binding and propidium iodide exclusion. Flow cytometry will also be used with bromodeoxyuridine labeling for analysis of the effect of candidate ADC on the cell cycle.

Conjugates Internalization and Subcellular Trafficking.

Antibody-mediated internalization and trafficking to lysosomes are important to elicit efficient cytotoxicity of antigen-expressing cells [50, 54], especially for RTX-P-EPI conjugate that is targeted to CD20 and releases EPI in lysosome. It was reported that a Rituximab-liposomal DOX was not effective against CD20 positive cells, which was partially attributed to non/slow-internalization of CD20 [55]. However, Rituximab-bound auristatin that is 10 to 200 times more potent than DOX shown internalization and significant antitumor activity [56]. As described herein, the conjugate RTX-P-EPI induces apoptosis and is more efficient at inhibiting tumor-growth compared with Rituximab alone or RTX+P-EPI. Next, experiments were performed to test whether Rituximab-P-EPI would ameliorate (alter, decrease or increase) the endocytosis pathways, enhance internalization and result in more efficiently trafficking to the lysosomes. To elucidate the mechanism of RTX-P-EPI, the following experiments were designed Active Targeting Investigation.

To evaluate whether conjugation of polymer to RTX will enhance the internalization of the conjugate, the cell uptake of RTX-P-EPI, IgG-P-EPI and RTX-EPI will be conducted and compared in CD20 positive Raji cells and CD20 deficient cells using flow cytometry. To confirm the Rituximab-associated active targeting, a ligand inhibition competitive experiment will be performed in the presence of excess free RTX. To rule out energy-independent or nonspecific cell-penetrating endocytosis, cell internalization will also be conducted in the presence of $NaN_3$ or 4° C.

Endocytosis Pathway Investigation.

Potential endocytosis pathways of RTX-P-EPI internalization will be conducted and compared with IgG-P-EPI and RTX-EPI after pretreatment with various inhibitors, e.g., chlorpromazine (10 µg/mL, clathrin inhibitor), filipin (1 µg/mL, caveolae inhibitor), amiloride (0.3 mg/mL, macropinocytosis inhibitor). The degree of inhibition will be presented as the percentage of internalized cells not pretreated.

Confocal Microscopy for Trafficking and Cellular Localization of Rituximab and Rituximab-Drug Conjugates.

To evaluate subcellular trafficking and localization of conjugates, Raji cells will be incubated with RTX-P-EPI, P-EPI or RTX-EPI at different time intervals (0.5, 1, 2, 4, 8 h) at 37° C. Then, specific subcellular compartments such as caveolae-1, clathrin protein, golgi, mitochondria, early endosome, late endosome, lysosome and nuclear will be stained with a corresponding fluorochrome. The trafficking process and subcellular colocalization will be monitored and imaged in live cells using confocal microscopy.

Stimulus-Responsive Intracellular EPI Release Visualization.

To better understand the intracellular drug release from RTX-P-EPI, and taking advantage of the built-in fluorescence of EPI, a FRET conjugate—Cy5-RTX-P-EPI (FIG. 20) was designed. FRET is a process in which energy is transferred from a fluorophore in an electronic-excited state serving as a donor to another chromophore or acceptor by long-range dipole-dipole coupling. It generates fluorescence signals sensitive to molecular conformation, association, and separation in less than 10 nm distance. FRET imaging can be used to gain insight into the function-mechanism relationship, including the development of drug delivery systems.

A water-soluble polymer-epirubicin conjugate containing pendent Cy5 was synthesized. A fluorescence spectrometer and confocal microscopy will be used to follow FRET signal changes in cancer cell. In this system, EPI linked to the polymer precursor via tetrapeptide GFLG will serve as donor, while Cy5 will be used to label RTX and serve as acceptor. The relative position between donor EPI and acceptor Cy5 is important. Once the polymer precursor containing EPI is attached to Rituximab via thioether bond, the resultant Cy5-RTX-P-EPI will have the FRET property. In other words, when the conjugate is excited at 445 nm, a FRET spectrum will be released (an emission spectrum of the donor-acceptor (400-800 nm) showing an emission peak of Cy5 at 645 nm). Upon internalization, followed by catabolic degradation of antibodies and cleavage of GFLG linker that was exposed to lysosomal enzymes, EPI will be released, thereby leading to the separation of the fluorophore pair and the loss of FRET signal.

Determination of Pharmacokinetics (PK) and Biodistribution of the Conjugate $^{125}$I-RTX-P-EPI.

Figure 19:
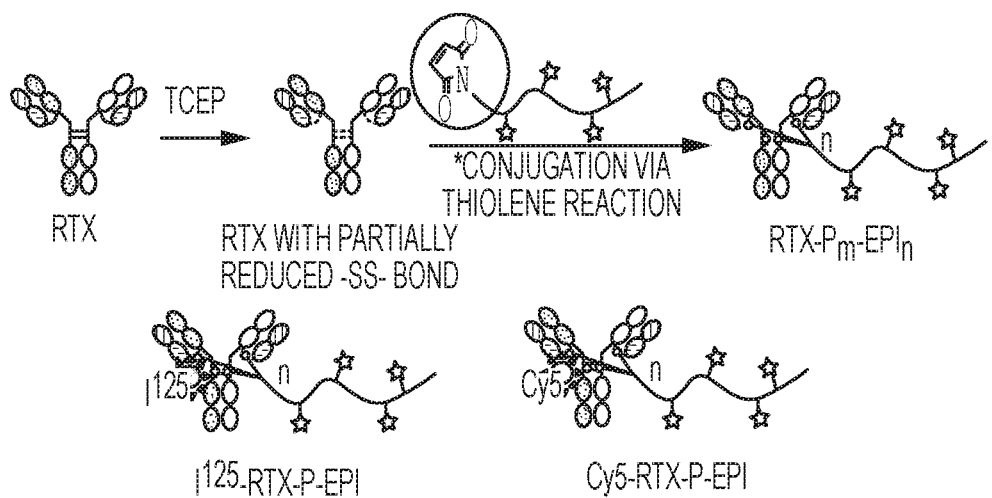
FIG. 19 shows the synthesis of isotope ($^{125}$I)-labeled and fluorophore (Cy5) labeled conjugates that can be used to carry out subcellular trafficking and PK/biodistribution studies.

These studies in conjunction with the in vitro and in vivo activities, will provide information regarding mechanism, efficacy, and toxicity, overall structure design and administration schedule. Different from non-target drug delivery system, one of the mechanisms of action of the APDCs described herein is the ability to recognize and bind to its specific antigen target, thus overall PK characteristics of an APDC including, for example, slow clearance, long half-life and limited tissue distribution can be driven by the antibody component. The PK/biodistribution experiments, and, in particular, the blood radioactivity-time profiles of RTX-P-EPI and RTX (FIG. 19), show that conjugation of 20 (or more) EPI (via linear polymer carriers) did not compromise the pharmacokinetic properties of the antibody RTX. The tumor model used is an aggressive lymophoma model and clinically relevant; while RTX treatment showed a marginal effect on efficacy, the RTX-P-EPI conjugate described herein is predicted to exhibit enhanced clinical activity.

The in vivo fate of $^{125}$I-labeled RTX-P-EPI will be investigated in SCID mice bearing subcutaneously Raji tumors. Three to four doses (related to RTX) will be administered to check PK-dose dependency, saturation dose effect and off-target binding/uptake.

Determination of Cytotoxicity Toward Raji Sensitive/Raji Resistant Cells.

Figure 21A:
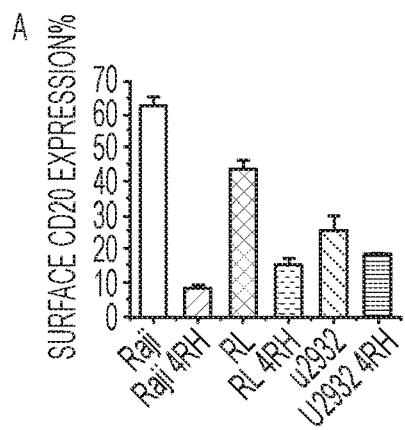
FIGS. 21A-B shows CD20 expression in different cell lines (A) and Raji cell growth arrest and apoptosis (B).

Several lymphoma cell lines, including RTX sensitive (RSCL) and RTX resistant (RRCL) will be used. The surface CD20 expression was determined in each cell line. The results are shown in Table 5 and FIG. 21A. Raji cell (Burkitt's lymphoma) showed the highest CD20 expression, and Raji 4RH showed the lowest level; however, for u2932 (diffuse large B-cell lymphoma cell lines) and u2932 4RH, there was no significant difference on CD20 expression, suggesting that there are some other reasons except CD20 level responsible to kill lymphoma. Rituximab resistance pathways remain uncertain. One of the mechanisms may be the frequently repeated dose and relatively high dosage. Another contributor for rituximab resistance is the altered signaling, resulting in anti-apoptotic proteins overexpression of the BCL-2 family and leading to resistance to apoptosis. EPI is reported to up-regulate Bax and Bak (the pro-apoptotic BCL-2 family proteins), so it may resensitize resistant cell lines to rituximab-mediated apoptosis. Next u2932 and u2932 4RH will be used to test the conjugates disclosed herein for their ability to overcome RTX-resistance and improve the therapeutic efficacy because using RTX-P-EPI will reduce the dose/dosage of RTX due to the cooperation of passive/active targeting and synergism between RTX and EPI; EPI may re-sensitize the cells from RRCL to RSCL; and RTX-P-EPI may bypass the preexisting resistance associated with altered internalization pathways.

TABLE 5

Conjugates and cells lines to be evaluated.

|   |   | Raji | Raji 4RH | RL | RL 4RH (FL) | U2932 | U2932 4RH (DLBCL) |
|---|---|---|---|---|---|---|---|
|   |   | Burkitt's |   |   |   |   |   |
| 1 | RTX-P-EPI | CD20+++ | CD20− | CD20++ | CD20± | CD20+ | CD20+ |
| 2 | IgG-P-EPI |   |   | Non-specific binding |   |   |   |
| 3 | 2P-EPI |   |   | No targeting moiety |   |   |   |
| 4 | RTX |   |   | Baseline |   |   |   |

Cell Growth Arrest and Apoptosis.

Figure 21B:
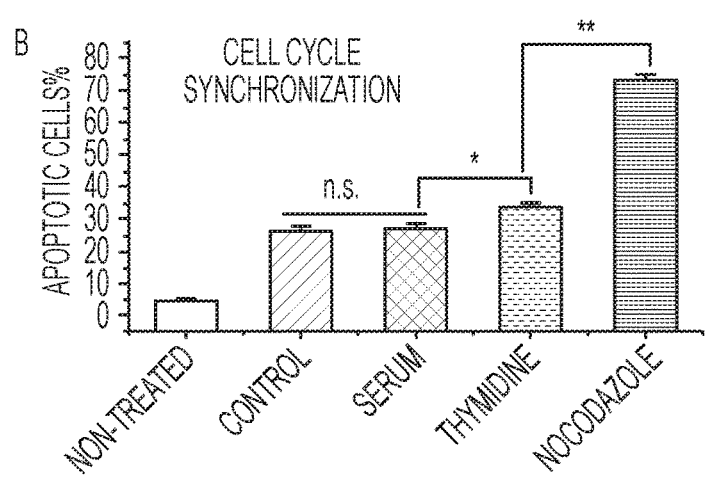
Figure 22A:
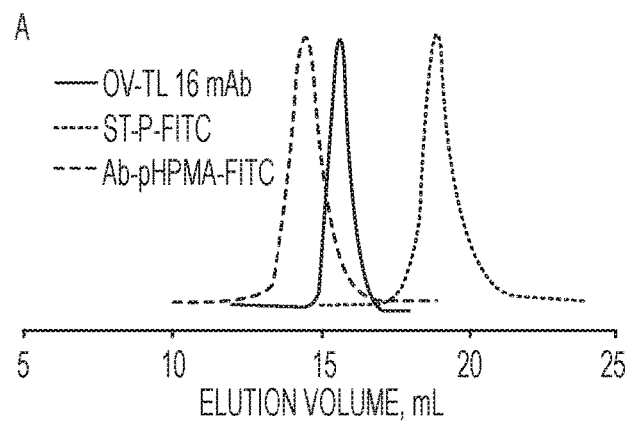
FIGS. 22A-D show the characterization of and evaluation of biological activity of OV-TL16 antibody-ST-HPMA copolymer-drug conjugates.
Figure 22B:
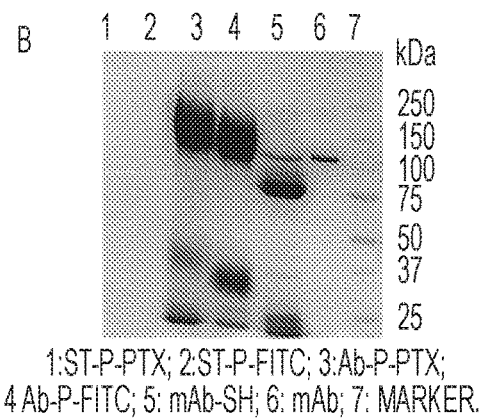
Figure 22C:
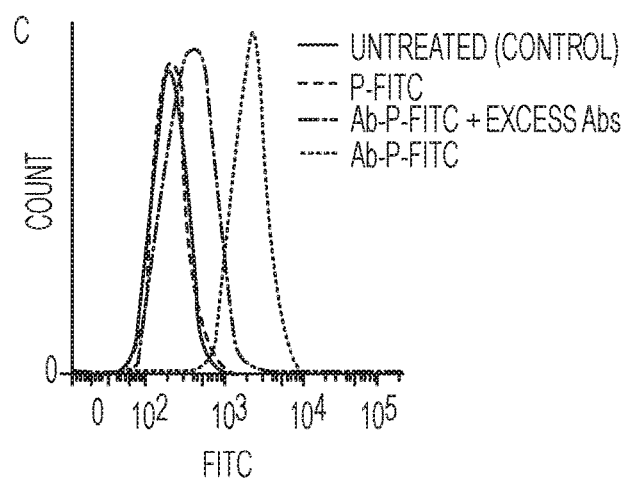
Figure 22D:
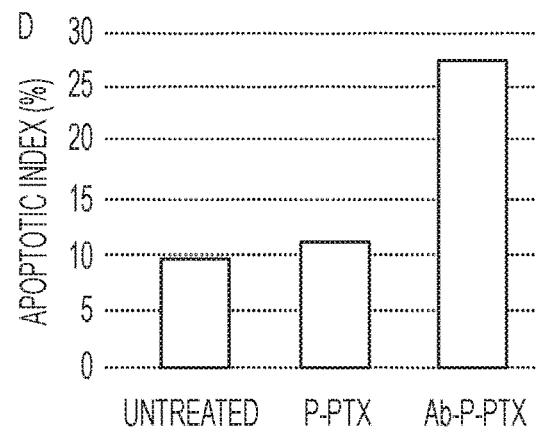

CD20 expression on cell surface may be different at different cell cycle phases, which can be synchronized. Therefore, the combination of chemotherapy that can arrest the cell growth may activate CD20 response to RTX. FIG. 21B showed cell cycle synchronization with serum, thymidine and nocodazole, respectively, and cell growth arrest and apoptosis were assessed by Annexin V binding to the cell surface and propidium iodide (PI) exclusion. The apoptosis level is related to the external CD20 expression (ranked according to the different phases: G2/M>S>G0/G1).

Data Analysis.

The Student's t test (assuming unpaired variables and unequal variance between samples) will be used to test differences in cellular binding and uptake, cytotoxicities, pharmacokinetic parameters, and toxicity among different conjugates. Comparison among groups will be performed using one-way ANOVA. The significance level will be set at 0.05.

The conjugates described herein, for example, RTX-P-EPI, are expected to improve the treatment of RTX. In some aspects, EPI can be replaced with a drug that promotes the stabilization of microtubules, for example, docetaxel (DTX). By changing one or more of the components of the APDC disclosed herein, additional mechanisms to induce apoptosis can be achieved. For example, DTX also suppresses the desmoplastic stroma growth, which leads to the dilation of blood vessels within tumors and decreases tumor interstitial fluid pressure. These additional actions may aid the penetration of RTX-P-DTX to reach its targeted cells. Moreover, DTX arrests cells in mitosis, a phase more fragile and vulnerable to apoptosis. In addition, DTX causes phosphorylation of the BCL-2 protein and subsequent caspase-3-dependent. Thus, DTX may also act in synergy with RTX in inhibiting BCL-2 level for apoptosis sensitization.

Evaluation of the Antibody-Polymer-Drug Conjugates to Treat Non-Hodgkin Lymphoma in Rodent Animal Models For in vivo evaluation, localized and disseminated xenograft models of human B-lymphoma will be used to address targeted uptake, the therapeutic effectiveness, and non-specific toxicity. Importantly, the effect of APDCs disclosed herein on human patient isolates of NHL of different phenotypes will also be studied. These studies will confirm the efficacy of the APDCs and provide signals of activity against different subtypes of B-cell malignancies.

Determination of Maximum Tolerated Dose (NTD) and Dose/Regime.

Before evaluating efficacy, the dose effect of RTX-P-EPI will be determined as well as the administration schedule. C57BL/6 mice will be used for toxicology studies. The mice will be intravenously administered with three different drug equivalent concentrations in a single escalating dose based on animal response. The mice will be sacrificed 14 days post injection and histopathological tissue analysis will be performed. Blood will be drawn from each animal for hematology analysis. Weight gain/loss over 14 days will be evaluated as a sign of general toxicity. The results will be correlated with in vitro cytotoxicity.

Evaluation of RTX-P-EPI in a Localized Model of Lymphoma.

To screen the conjugates for efficacy using different lymphoma cell lines, a solid tumor model will be generated by inoculating cells subcutaneously (suspended in Matrigel) at $5 \times 10^6$ cells/mouse to the posterior flank of 6- to 8-week-old SCID mice. Tumor volume will be determined by caliper measurement daily [39]. Once tumor volumes reach approximately 250 mm$^3$, mice will be assigned to three groups, control, RTX-P-EPI (30 mg/kg), or RTX (30 mg/kg). Conjugates will be intravenously administered via tail vein on days 0, 3, 7, and 10 following tumor engraftment. Tumor volume will be monitored by serial caliper measurement. Mice with a tumor exceeding 2 cm in largest diameter will be sacrificed. A tumor of >2 cm in diameter will be used as the survival endpoint in a Kaplan-Meier analysis. IgG-P-EPI will be used as isotype control.

Non-specific toxicity will be evaluated by harvesting organs (heart, lung, liver, spleen, kidney) immediately after sacrifice for histopathological examination. Treated and non-treated mice will be compared to evaluate the any non-specific toxicity of the conjugates.

Evaluation of RTX-P-EPI on Disseminated Model of Lymphoma.

Figure 23:
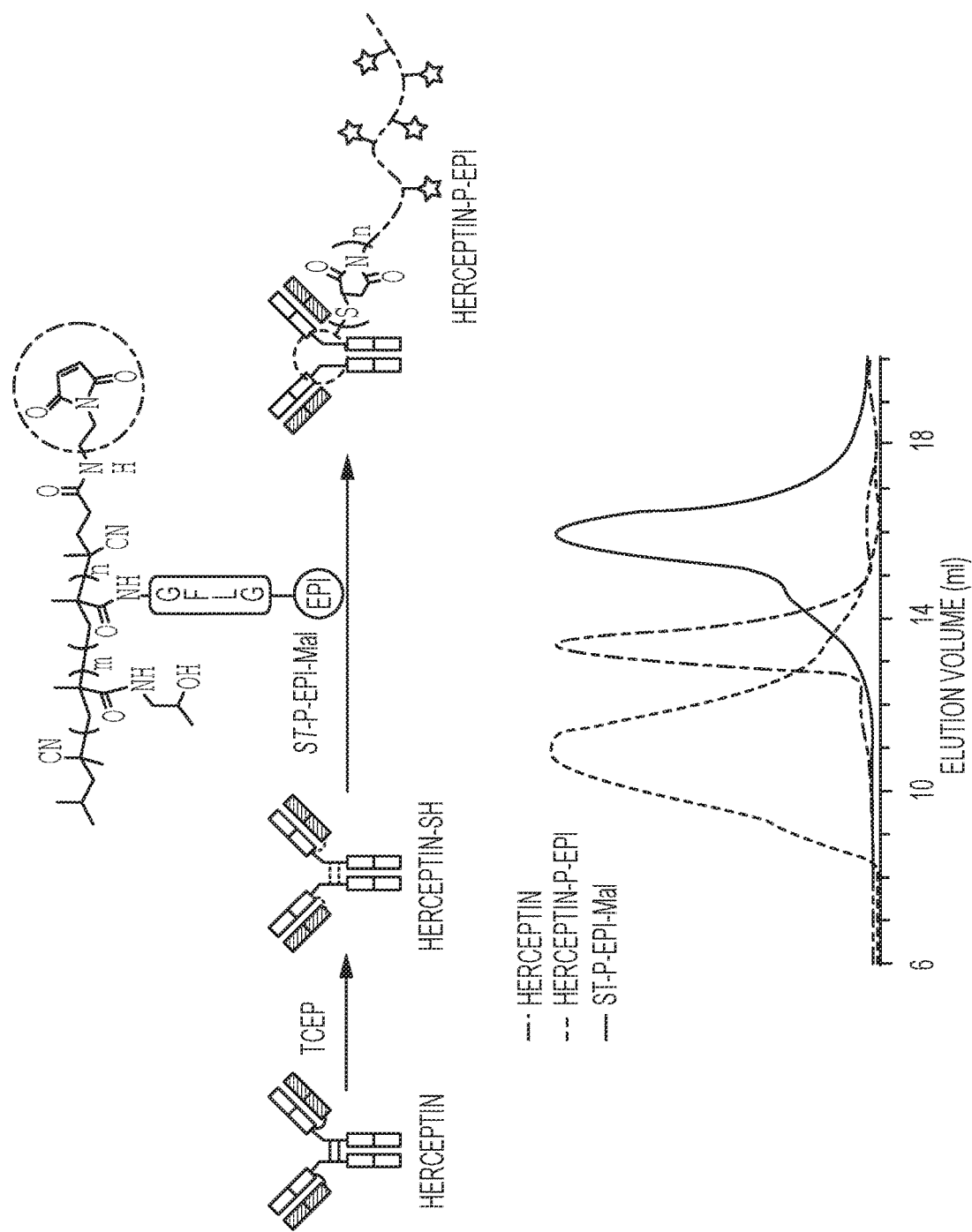
FIG. 23 shows the FPLC analysis of the Herceptin-P-EPI conjugate. GFLG corresponds to SEQ ID NO: 1.

A disseminated lymphoma model was used to evaluate the conjugates described herein by intravenous injection of $4 \times 10^6$ Raji or Luc+ Raji cells into immunodeficient CB17-SCID/beige mice (FIG. 23). Tumor cells seed distal locations, grow and eventually cause hind limb paralysis [57-59]. The mice that did not receive treatment developed hind-limb paralysis in about one month after cell injection. The paralysis is due to tumor growth in the bone marrow, which affects the spinal cord. Raji tumors also form in the spleen as well as in axillary and mesenteric lymph nodes. This model therefore reflects tumor cell growth in patients with B-cell malignancies.

In this study, we will evaluate the in vivo anti-NHL activity of conjugate RTX-P-EPI against RTX-sensitive and RTX-resistant models will also be evaluated. Six to 8-week-old SCID mice will be xenografted with intravenous injection of Luc+ Raji and Raji4RH (RTX-resistant) cells at $5 \times 10^6$ cells/mouse. One week after tumor cell injection, mice will be randomly divided into 5 groups: (i) PBS (control), (ii) isotype control (IgG-P-EPI), (iii) RTX-P-EPI (30 mg/kg), (iv) RTX (30 mg/kg)+P-EPI, and (v) RTX (30 mg/kg). Mice will be treated weekly for 8 weeks. Mice in the variables (ii) and (iv) will receive an equal dose of EPI as mice in variable (iii). Tumor regression and/or progression of xenografted mice will be monitored weekly using in vivo bioluminescent imaging and paralysis-free survival as an endpoint. Mice developing paralysis will be sacrificed. Otherwise, surviving mice will be observed up to 100 days after NHL cell inoculation.

Statistical Analysis.

For comparison of results between groups, the t test for unpaired variables and unequal variance between samples will be used. If distributions are excessively skewed, the rank-based Wilcoxon test will be used. Differences will be considered statistically significant for two-sided p values below 0.05. Sample size projection will be determined using normal power calculations. With 7 samples per group, there is 90% power to detect a difference of 2 standard deviations between groups using a two-sample t-test.

Expected Results.

Significant anti-NHL activity in Rituximab-sensitive models is expected. Different reactions between RTX-P-EPI and RTX alone for RTX-resistant models are also expected. The dosing schedule will be modified during therapeutic efficiency evaluation based on the results of the first set of experiments.

Evaluation of the Activity of Conjugates Disclosed Herein Against NHL Patient Isolates of Different Phenotypes.

CD20 is expressed by virtually all B-cell NHLs [5]. However, the activity of anti-CD20 antibodies (such as RTX) varies between different subtypes of NHL. This variability is due at least in part to different levels of CD20 expression by the different subtypes of B-cell malignancies. Cells from the four most common B-cell malignancies that express CD20 will be used, namely diffuse large B-cell lymphoma (DLBCL), mantle cell lymphoma, follicular lymphoma, and chronic lymphocytic leukemia (CLL) in order to study the effect of the APDCs described herein on these different types of NHL.

Cell sources will be either diagnostic bone marrows or lymph node biopsies from patients with the above-listed diseases. Cells will be treated with candidate APDCs at concentrations based on work described above [24]. Analyses will be conducted at 24, 48, and 72 h for cytotoxicity. Assays will include Trypan blue exclusion, Annexin V positivity, propidium iodide staining for cell cycle analysis (sub-G0 fraction) and activation of apoptosis pathway proteins (caspases 3, 7, 8, and 9, Bcl-2 family proteins). RTX will be used as a control. Responses for each disease will be compared between samples obtained at the time of initial diagnosis and cells obtained at the time of relapse. Also, the in vitro response to the APDCs will be correlated with prior CD20-directed therapy that the patient has received. For the subtypes of B-cell malignancy, responses will be correlated to establish clinical prognostic factors for each disease. In addition, responses will be correlated to the level of expression of CD20 as determined by the diagnostic flow cytometric analysis.

Statistical Analysis.

Assays will be conducted in triplicate. For comparison of results between groups, the t test for unpaired variables and unequal variance between samples will be used. If distributions are excessively skewed, the rank-based Wilcoxon test will be used. Differences will be considered statistically significant for two-sided p values below 0.05. Studies will be conducted on at least forty different samples from different histologies.

Expected Results.

Significant cytotoxic activity is expected in all samples. However, different subtypes of B-cell malignancies may respond differently. Also, within each subtype, there may be differences in responses between different prognostic groups, such as germinal center B-cell-like (GCB) and activated B-cell-like (ABC) for DLBCL. It is also possible that responses may be related to differences in CD20 expression by the different subtypes of NHL.

The studies disclosed herein seek to identify and generate an APDC, for example, RTX-P-EPI, that has potent activity against cancer, and more specifically, against B-cell malignancies. A clinical development program will be initiated, including a scale-up production and IND-enabling study (including animal toxicology) leading to a Phase I clinical trial program in patients with relapsed/refractory disease.

Example 8: OVTL-16 mAb-P-Paclitaxel Conjugate

OV-TL16 mAb recognizes the OA-3 antigen (CD47) expressed on the surface of OVCAR-3 cells and on 90% of human ovarian carcinomas. Recently the use of the anti-CD47 antibody emerged as a new anticancer approach. It was found that CD47 functions as a signal "don't eat me" for phagocytic cells and its overexpression in nearly all cancer cells results in the suppression of phagocytic innate immune surveillance and elimination. Blockade of CD47 may provide therapeutic benefits for cancers and other diseases including cardiovascular failure and inflammation. FIG. 22 shows the characterization of and evaluation of biological activity of OV-TL16 antibody-ST-HPMA copolymer-drug conjugates.

Synthesis of Semitelechelic HPMA Polymer—Paclitaxel Conjugate (ST-P-PTX) and Fluorescent Control ST-P-FITC.

276 mg HPMA and 37 mg N-methacryloyl aminopropyl fluorescein thiourea (MA-FITC) (or 45 mg N-methacry-loylglycylphenylalanylleucylglycine-PTX, MA-GFLG-PTX) were added into an ampoule attached to a Schlenk-line. 2-cyano-5-oxo-5-(2-thioxothiazolidin-3-yl)pental-2-yl benzodithioate (CTA-TT) was used as chain transfer agent (CTA) and V70 was added as initiator. The copolymerization was carried out at 40° C. in methanol/DMSO (2:1 v/v) for 5 h. The polymer was isolated by precipitation into ether/acetone. Dithiobenzoate group was removed by reaction with large excess of V70, and maleimide was incorporated by reaction of N-ethylamino maleimide with polymer chain end thiazolidine-2-thione (TT). The average molecular weight and the polydispersity of the conjugate were determined by size exclusion chromatography (SEC) on an AKTA FPLC system. The presence of a maleimide group was confirmed by modified Ellman assay; FITC content was measured using UV-vis at 495 nm in sodium borate buffer (pH 9.0); and PTX content was determined by HPLC after cleavage by papain.

Attachment of ST-P-PTX to OVTL-16 Antibody.

OV-TL16 antibody (Ab) was buffer exchanged to a final concentration of 1 mg/mL in 4 mL Tris.HCl (10 mM, 150 mM NaCl, 5 mM EDTA, pH 7.4). TCEP (10× in $H_2O$) was added to the solution and incubated at 37° C. for 3 h, then purified with ultrafiltration (30,000 MWCO, Amicon®Ultra) to yield Ab-SH. ST-P-PTX (or ST-P-FITC) (50× in $H_2O$) was added to the Ab-SH solution and incubated at 37° C. for another 2 h. Ab-P-PTX (or Ab-P-FITC) was obtained after removal of unreacted polymer with ultrafiltration (30,000 MWCO, Amicon®Ultra).

Targeting Effect.

The SKOV-3 cells were incubated with 10 μg/mL Ab-P-FITC at 37° C. for 1 h. Controls: pre-exposure of large excess (50-fold) Abs followed by Ab-P-FITC; ST-P-FITC; and untreated group. Flow cytometry was used to analyze binding activity.

Cytotoxicity.

The SKOV-3 cells were treated with Ab-P-PTX conjugate and ST-P-PTX (10 μM PTX equivalent for each) at 37° C. for 1 h. Then the drug was removed and the cells were cultured for another 20 h. The cells were stained with Annexin V-FITC and PI (propidium iodide), and analyzed using flow cytometry. The untreated cells served as a control.

Example 9: Trastuzumab-P-Epirubicin Conjugate

Trastuzumab (Herceptin) is a commercially available antibody that binds to the HER2-receptor, e.g., in HER2-positive breast cancer cells.

Synthesis of Semitelechelic Maleimide Functionalized HPMA Copolymer-Epirubicin Conjugate.

Semitelechelic (ST) HPMA copolymer-epirubicin conjugate terminated at one chain end with maleimide group was prepared by RAFT copolymerization followed by two-step end modification. An ampoule containing HPMA (139 mg, 0.97 mmol) and N-methacryloylglycylphenylalanyl-leucylglycine-epirubicin (MA-GFLG-EPI; 30 mg, 0.03 mmol) were attached to the Schlenk line. After three vacuum-nitrogen cycles to remove oxygen, 2-cyano-5-oxo-5-(2-thioxothiazolidin-3-yl)pental-2-yl benzodithioate (CTA-TT; 4 mg/mL×170 μL, in degassed MeOH/H+0.3% acetic acid) and 2,2'-azobis(4-methoxy-2,4-dimethylvale-ronitrile) (V70; 1 mg/mL×184 μL, in degassed MeOH/H+ 0.3% acetic acid) were added via syringe under magnetic stirring and bubbled with $N_2$ for 10 min in ice bath. The ampoule was sealed, and polymerization was performed at 30° C. for 22 h. The copolymer was obtained by precipitation into acetone/ethyl ether and purified by redissolving in methanol and precipitation in acetone/ethyl ether two more times. The copolymer was isolated as red powder and dried under vacuum. The average molecular weight (Mw) and the polydispersity (PDI) of the conjugates were determined using size-exclusion chromatography (SEC) on ÄKTA FPLC system equipped with a UV detector (GE Healthcare), mini DAWN TREOS, and OptilabrEX (refractive index) detector (Wyatt Technology) using a Superose 6 HR10/30 column with sodium acetate buffer containing 30% acetonitrile (pH 6.5) as mobile phase. The dithiobenzoate end group was removed by further reaction with 40-times excess of 2,2'-azobis(2,4-dimethylvaleronitrile) (V-65) in 0.3 mL MeOH/H+ at 55° C. for 2 h; the modified conjugate was isolated by precipitation into acetone/ethyl ether twice, resulting in ST-P-EPI-TT (70 mg, 41%). The content of EPI in the copolymer was determined spectrophotometrically ($\lambda$max=495 nm) by dissolving ST-P-EPI-TT in methanol (~2 mg/10 mL) and calculated according to EPI standard curve in methanol. The end-chain reactive maleimide (mal) group was incorporated by the reaction of TT (thiazolidine-2-thione) group with N-(2-aminoethyl)maleimide. For example, 18 mg ST-P-EPI-TT was dissolved in 500 µL DMSO, then the solution was added into 0.1 mL DMSO containing 10 µL DIPEA and 5 mg N-(2-aminoethyl)maleimide trifluoroacetate. After stirring at room temperature for 24 h, the polymer was isolated by precipitation in acetone/ether three times to yield 16.5 mg ST-P-EPI-Mal. The presence of maleimide group was confirmed by modified Ellman assay (FIG. 1).

Conjugation of ST-P-EPI-Mal to Herceptin.

Herceptin (18 mg) was buffer changed with Tris.HCl (20 mM, 150 mM NaCl and 5 mM EDTA, pH 7.4) buffer by ultrafitration (MWCO (molecular weight cut-off) 30,000) three times to final volume 4 mL, then 0.4 mL of TCEP (100 mM, in Tris.HCl buffer, pH 7.1) was added and incubated at 37° C. for 3 h. The excess TCEP was removed by ultrafiltration (MWCO 30,000) four times with Tris.HCl buffer to yield Herceptin-SH. Herceptin-SH (18 mg in 4 mL Tris.HCl buffer) was mixed with 1.5 mg ST-P-EPI-Mal in 2 mL Tris.HCl buffer and incubated at 37° C. for 6 h. After working up, the Herceptin-P-EPI conjugate was purified using SEC on ÄKTA FPLC system (GE Healthcare, Piscataway, N.J.) equipped with Sephacryl S-100 HR16/60 column eluted with PBS (pH 7.2) to remove free, unconjugated ST-P-EPI-Mal. FPLC analysis confirmed the successful synthesis of conjugates (FIG. 23). The protein concentration (Herceptin) in final solution was determined with BCA protein assay, whereas the polymer content was evaluated using UV-vis spectroscopy based on EPI content. Consequently, the drug-to-antibody ratio (DAR) was calculated. EPI/Herceptin=16.0.

Example 10: Conjugation of ST-P-EPI-Mal to IgG

To demonstrate the general applicability of conjugation technique described herein, non-specific IgG was used for the synthesis of IgG-P-EPI conjugate. IgG was reduced with TCEP as described above, excess of TCEP was removed by ultrafiltration four times with Tris.HCl buffer. ST-P-EPI was added to IgG-SH solution and incubated 6 h at 37° C. After working up, the IgG-P-EPI conjugate was purified using SEC on ÄKTA FPLC system (GE Healthcare, Piscataway, N.J.) equipped with Sephacryl S-100 HR16/60 column eluted with PBS (pH 7.2) to remove free, unconjugated ST-P-EPI. FPLC and SDS-PAGE analysis confirm the success synthesis of IgG-P-EPI conjugates. The protein concentration in final solution was determined with BCA protein assay, whereas the polymer content was evaluated using UV-vis spectrophotometry based on EPI content. Consequently, the drug-to-antibody ratio (DAR) was calculated. EPI/IgG was 16.9 for IgG-P-EPI.

Example 11: OV-TL16-P-Epirubicin Conjugate

OV-TL 16 mAb (anti-ovarian cancer antibody) was selected for binding with semitelechelic HPMA copolymer-epirubicin conjugate (P-EPI).

Figure 24:
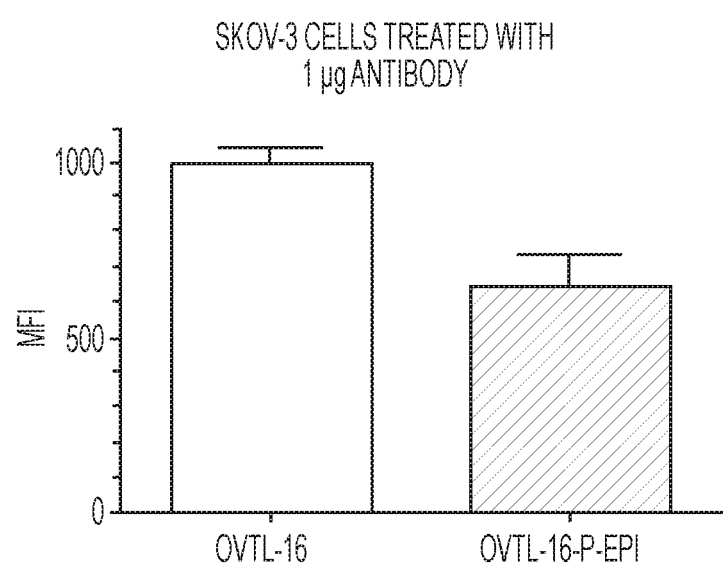
FIG. 24 shows the mean fluorescence intensity (MFI) of SKOV-3 cells following exposure to OVTL-16 alone or OVTL-16-P-EPI.

OV-TL16 mAb recognizes the OA-3 antigen (CD47) expressed on the surface of OVCAR-3 cells and on 90% of human ovarian carcinomas. Similar to the preparation of RTX-P-EPI, semitelechelic HPMA polymer-epirubicin conjugate (ST-P-EPI) was selectively attached to freshly reduced OV-TL16 Ab via thiol-maleimide reaction. The binding affinity of the antibody-drug conjugate (OVTL-16-P-EPI) was determined using flow cytometry and compared with the antibody alone. The result demonstrated >60% binding affinity retained after conjugation (FIG. 24).

SKOV-3 cells ($2\times10^5$) in 50 µl medium was mixed with different samples and incubated at 4° C. for 30 min. The cells were then washed with fresh medium twice to remove unbound antibody or antibody-drug conjugate. Secondary antibody GAM-488 (100 µL, 1:200 diluted) was then added and cells were incubated at 4° C. for another 30 min. After washing with PBS, the cells were analyzed by flow cytometry. All data in FIG. 24 are presented as mean±SD (n=3).

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An antibody-polymer-drug conjugate comprising:
a targeting antibody bonded to a polymer comprising:
a first monomer residue having a structure:

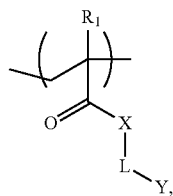

wherein $R_1$ is hydrogen or methyl, wherein X is oxygen or $NR_1'$, wherein $R_1'$ is hydrogen or an alkyl group, wherein L is an alkyl group or an aryl group, and wherein Y is a hydrophilic group;
and
a second monomer residue having a structure

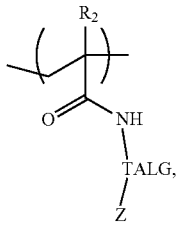

wherein $R_2$ is hydrogen or methyl, wherein Z is a therapeutic agent,
wherein TALG is an oligopeptide therapeutic agent linking group which is stable under physiologic conditions and cleaved in lysosomal compartment and
wherein the targeting antibody is bonded to the polymer via a linkage having the structure:

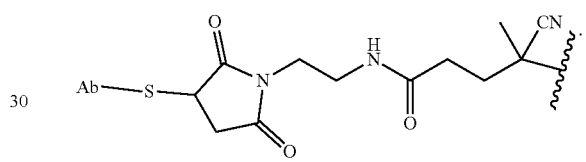

2. The conjugate of claim 1, wherein targeting antibody is abciximab, adalimumab, alemtuzumab, basiliximab, belimumab, bevacizumab, brentuximab, canakinumab, cetuximab, daclizumab, efalizumab, gemtuzumab, golimumab, ibritumomab, infliximab, ipilimumab, motavizumab, obinutuzumab, ofatumumab, omalizumab, OV-TL-16, palivizumab, pertuzumab, ranibizumab, raxibacumab, rituximab, tocilizumab, trastuzumab, or ustekinumab.

3. The conjugate of claim 1, wherein the targeting antibody is an anti-CD20 monoclonal antibody, an anti-OA-3 monoclonal antibody, or an anti-HER2 monoclonal antibody.

4. The conjugate of claim 1, wherein the therapeutic agent linking group is Gly-Gly, Gly-Phe-Gly, Gly-Phe-Phe, Gly-Leu-Gly, Gly-Val-Ala, Gly-Val-Leu, Gly-Val-Phe, Gly-Phe-Ala, Gly-Leu-Phe, Gly-Leu-Ala, Gly-Ile-Ala, Ala-Val-Ala, Ala-Val-Phe, Ala-Phe-Val, Gly-Phe-Leu-Gly (SEQ ID NO: 1), Gly-Phe-Phe-Leu (SEQ ID NO: 2), Gly-Leu-Leu-Gly (SEQ ID NO: 3), Gly-Phe-Tyr-Ala (SEQ ID NO: 4), Gly-Phe-Gly-Phe (SEQ ID NO: 5), Ala-Gly-Val-Phe (SEQ ID NO: 6), Gly-Phe-Phe-Gly (SEQ ID NO: 7), Gly-Phe-Leu-Gly-Phe (SEQ ID NO: 8), Gly-Gly-Phe-Leu-Gly-Phe (SEQ ID NO: 9), N-aminocaproyl-Val-Citruline, or a combination thereof.

5. The conjugate of claim 1, wherein the therapeutic agent is an anti-cancer agent.

6. The conjugate of claim 1, further comprising residues of a monomer selected from the group consisting of N-(2-hydroxypropyl) methacrylamide, 2-hydroxyethyl methacrylate, diethylene glycol monomethacrylate, triethylene glycol monomethacrylate, acrylonitrile, methacrylonitrile, acrylamide, methacrylamide, N-alkylmethacrylamide, N-alkylacrylamide, N,N-dialkylacrylamide, methacrylic acid, acrylic acid, esters of acrylic acid, esters of methacrylic acid, N,N-diethylaminoethyl methacrylate, N-vinylpyrrolidone, norbornene, and combinations thereof.

7. A pharmaceutical composition comprising the conjugate of claim 1 and a pharmaceutically acceptable carrier.

8. The conjugate of claim 1, wherein the targeting antibody is rituximab, Herceptin or OV-TL16, the first monomer residue is a residue of N-(2-hydroxypropyl) methacrylamide, and the therapeutic agent is epirubicin.

9. The conjugate of claim 1, wherein the therapeutic agent is selected from epirubicin, doxorubicin, daunorubicin, idarubicin, paclitaxel, 10-deacetylbaccatin III, baccatin III, paclitaxel C, and 7-epipaclitaxel.

10. The conjugate of claim 1, wherein the first monomer residue is a residue of HEMA or HPMA.

11. The antibody-polymer-drug conjugate of claim 1,
wherein the first monomer residue is a residue of HEMA or HPMA;
wherein the therapeutic agent linking group is Gly-Gly, Gly-Phe-Gly, Gly-Phe-Phe, Gly-Leu-Gly, Gly-Val-Ala, Gly-Val-Leu, Gly-Val-Phe, Gly-Phe-Ala, Gly-Leu-Phe, Gly-Leu-Ala, Gly-Ile-Ala, Ala-Val-Ala, Ala-Val-Phe, Ala-Phe-Val, Gly-Phe-Leu-Gly (SEQ ID NO: 1), Gly-Phe-Phe-Leu (SEQ ID NO: 2), Gly-Leu-Leu-Gly (SEQ ID NO: 3), Gly-Phe-Tyr-Ala (SEQ ID NO: 4), Gly-Phe-Gly-Phe (SEQ ID NO: 5), Ala-Gly-Val-Phe (SEQ ID NO: 6), Gly-Phe-Phe-Gly (SEQ ID NO: 7), Gly-Phe-Leu-Gly-Phe (SEQ ID NO: 8), Gly-Gly-Phe-Leu-Gly-Phe (SEQ ID NO: 9), N-aminocaproyl-Val-Citrulline, or a combination thereof;
wherein the therapeutic agent is selected from epirubicin, doxorubicin, daunorubicin, idarubicin, paclitaxel, 10-deacetylbaccatin III, baccatin III, paclitaxel C, and 7-epipaclitaxel;
wherein Ab is the targeting antibody; and
wherein the targeting antibody is abciximab, adalimumab, alemtuzumab, basiliximab, belimumab, bevacizumab, brentuximab, canakinumab, cetuximab, daclizumab, efalizumab, gemtuzumab, golimumab, ibritumomab, infliximab, ipilimumab, motavizumab, obinutuzumab, ofatumumab, omalizumab, OV-TL-16, palivizumab, pertuzumab, ranibizumab, raxibacumab, rituximab, tocilizumab, trastuzumab, or ustekinumab.

12. The conjugate of claim 1, wherein the second monomer residue has a structure:

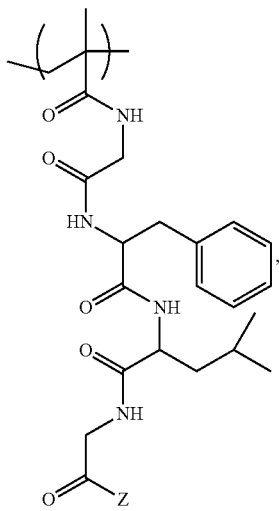

wherein the oligopeptide therapeutic agent linking group is Gly-Phe-Leu-Gly (SEQ ID NO: 1).

* * * * *